(12) United States Patent
Vink

(10) Patent No.: US 10,858,631 B2
(45) Date of Patent: Dec. 8, 2020

(54) METHODS FOR ADENO-ASSOCIATED VIRAL VECTOR PRODUCTION

(71) Applicant: GLAXOSMITHKLINE INTELLECTUAL PROPERTY DEVELOPMENT LIMITED, Brentford (GB)

(72) Inventor: Conrad Vink, Stevenage (GB)

(73) Assignee: GlaxoSmithKline Intellectual Property Development Limited, Brentford (GB)

( * ) Notice: Subject to any disclaimer, the term of this patent is extended or adjusted under 35 U.S.C. 154(b) by 0 days.

(21) Appl. No.: 15/955,992

(22) Filed: Apr. 18, 2018

(65) Prior Publication Data
US 2018/0327722 A1 Nov. 15, 2018

(30) Foreign Application Priority Data

Apr. 18, 2017 (GB) .................................... 1706090.6
Nov. 2, 2017 (GB) .................................... 1718179.3

(51) Int. Cl.
*C12P 21/06* (2006.01)
*C12N 15/00* (2006.01)
(Continued)

(52) U.S. Cl.
CPC ................ *C12N 7/00* (2013.01); *C12N 15/86* (2013.01); *C12N 2750/14121* (2013.01); *C12N 2750/14143* (2013.01); *C12N 2750/14152* (2013.01)

(58) Field of Classification Search
None
See application file for complete search history.

(56) References Cited

U.S. PATENT DOCUMENTS 6,037,177 A * 3/2000 Snyder ................... C12N 15/86
435/320.1
6,793,926 B1 9/2004 Rasty et al.
(Continued)

FOREIGN PATENT DOCUMENTS

WO    WO 98/46728 A1    10/1998
WO    WO 99/20778 A1    4/1999
(Continued)

OTHER PUBLICATIONS

Henrikssen et al., "Comparison of RNAi efficiency mediated by tetracycline-responsive H1 and U6 promoter variants in mammalian cell lines," Nucleic Acids Research, vol. 35, No. 9 (Year: 2007).*
(Continued)

*Primary Examiner* — M Franco G Salvoza
(74) *Attorney, Agent, or Firm* — Carly A. Shanahan; Fang Qian; Edward R. Gimmi

(57) ABSTRACT

The invention relates to an adeno-associated virus (AAV) producer cell comprising nucleic acid sequences encoding: rep/cap gene; helper virus genes; and the DNA genome of the AAV vector particle, wherein the nucleic acid sequences are all integrated together at a single locus within the AAV producer cell genome. The invention also relates to nucleic acid vectors comprising a non-mammalian origin of replication and the ability to hold at least 25 kilobases (kb) of DNA, characterized in that the nucleic acid vectors comprise nucleic acid sequences encoding: rep/cap gene, and helper virus genes. The invention also relates to uses and methods using the nucleic acid vectors in order to produce stable AAV packaging and producer cell lines.

32 Claims, 26 Drawing Sheets

Specification includes a Sequence Listing.

(51) Int. Cl.
*C12N 7/00* (2006.01)
*C12N 15/86* (2006.01)

(56) References Cited

U.S. PATENT DOCUMENTS

| | | | |
|---|---|---|---|
| 7,943,379 B2* | 5/2011 | Beall | C12N 7/00 435/235.1 |
| 2004/0209364 A1 | 10/2004 | Grimm et al. | |
| 2005/0130184 A1* | 6/2005 | Xu | C12N 15/111 435/6.16 |
| 2005/0233457 A1* | 10/2005 | Block | C12N 15/635 435/456 |
| 2006/0063231 A1* | 3/2006 | Li | A61K 48/00 435/69.1 |
| 2011/0247088 A1* | 10/2011 | Bujard | C12N 15/635 800/13 |
| 2014/0242671 A1* | 8/2014 | Grieger | C12N 7/00 435/239 |
| 2014/0256799 A1* | 9/2014 | Wong, Jr. | C12N 15/1131 514/44 R |
| 2015/0218586 A1 | 8/2015 | Schleef | |

FOREIGN PATENT DOCUMENTS

| | | |
|---|---|---|
| WO | WO 01/92551 A2 | 12/2001 |
| WO | WO 03/104413 A2 | 12/2003 |
| WO | WO 2007/084773 A2 | 7/2007 |
| WO | WO 2011/005793 A1 | 1/2011 |
| WO | WO2017/077275 A1 | 5/2017 |

OTHER PUBLICATIONS

Conway, et al., Recombinant adeno-associated virus type 2 replication and packaging is entirely supported by herpes simplex virus type 1 amplicon expressing rep and cap, Journal of Virology, 71(11):8780-8789 (1997).

Moriarity, et al., Modular assembly of transposon integratable multigene vectors using RecWay assembly, Nuc. Acids Research, 41(8):e92 (2013).

Yuan, et al., A versatile adeno associated virus vector producer cell line method for scalable vector production of different serotypes, Human Gene Ther., 22(5):613-624 (2011).

* cited by examiner

Figure 3

AAV cap2/5 shRNA:

AAV rep2 shRNA 5:

AAV rep2 shRNA 7:

Figure 3 (continued)

AAV rep2 shRNA 9:

```
Start (0)  NheI                                                                              XhoI   End (120)
5'  gctagcaaggtatattgctgtgacagtgagcgacgggaactcaaacgaccctttagtgaagcacagatgtaaaggtcgtgagttccgtcaatgcctactgcctcggactctgag  3'
3'  cgatcgttccatataacgacaactgtcactcgctgccttgagtttgctgggttgagttgctggaaatcacttcgtgtctacattccagcagcacctaaggtcagtttacggatgacggagcctgagagctc  5'                                                                                                                                                               120
```

AAV rep2 shRNA 11:

```
Start (0)  NheI                                                                              XhoI   End (120)
5'  gctagcaaggtatattgctgttgacagtgagcgagagcatcgtcgtactgcctcgtacttaagatgatgtatttgacgtgaattcatgctccatgctctcgactctgag  3'
3'  cgatcgttccatataacgacaactgtcactcgctctcgtagcagcatgacggagcatgaattctacttacataaactgcacttaagtacgagacgatactcgtagcagagctgagagctc  5'                                                                                                                                                               120
```

AAV rep2 shRNA 13:

```
Start (0)  NheI                                                                              XhoI   End (120)
5'  gctagcaaggtatattgctgttgacagtgagcgagcggatgttcaaattgacatccggtcctatgcctgctcgactctgag  3'
3'  cgatcgttccatataacgacaactgtcactcgctcgcctacaagtttaaactgtaggccaggatacggacgagctgagagctc  5'                                                                                                                                                               120
```

AAV rep2 shRNA 14:

```
Start (0)  NheI                                                                              XhoI   End (120)
5'  gctagcaaggtatattgctgttgacagtgagcgacaatgaagacagaactttccttcgaataagtgaagcacagatgtattgaaggaagttccttcgactctgag  3'
3'  cgatcgttccatataacgacaactgtcactcgctgttacttctgtcttgaaaggaagcttattcacttcgtgtctacataacttccttcaagaagctgagagctc  5'                                                                                                                                                               120
```

Cloning of first element:

Cloning of second element:

CONTINUED 1

*CONTINUED 2*

CONTINUED 1*

CONTINUED 2

*CONTINUED 3*

CONTINUED 4

CONTINUED 5

METHODS FOR ADENO-ASSOCIATED VIRAL VECTOR PRODUCTION

CROSS REFERENCE TO RELATED APPLICATION

This application claims the benefit of U.K. Provisional Application No. 1706090.6, filed on Apr. 18, 2017.

FIELD OF THE INVENTION

The invention relates to nucleic acid vectors comprising genes required for adeno-associated viral (AAV) vector production and uses thereof. Also provided are methods of making AAV packaging and producer cell lines comprising the nucleic acid vectors as described herein.

BACKGROUND TO THE INVENTION

In gene therapy, genetic material is delivered to endogenous cells in a subject in need of treatment. The genetic material may introduce novel genes to the subject, or introduce additional copies of pre-existing genes, or introduce the wild type variant of genes that are defective in the subject. Viral vector systems have been proposed as an effective gene delivery method for use in gene therapy (Verma and Somia (1997) *Nature* 389: 239-242).

Adeno-associated virus (AAV) was discovered in 1965, as a contaminant of adenovirus preparations. AAV has a linear single-stranded DNA (ssDNA) genome of approximately 4.7-kilobases (kb), with two 145 nucleotide-long inverted terminal repeats (ITR) at the termini. The ITRs flank the two viral genes—rep (replication) and cap (capsid), encoding non-structural and structural proteins, respectively and are essential for packaging of the AAV genome into the capsid and for initiating second strand DNA synthesis upon infection. AAV has been classified as a Dependoparvovirus (a genus in the Parvoviridae family) because it requires co-infection with helper viruses such as adenovirus, herpes simplex virus (HSV) or vaccinia virus for productive infection in cell culture (Atchison et al. (1965) *Science* 149:754; Buller et al. (1981) *J. Virol.* 40: 241).

AAV vectors have demonstrated transduction and long-term gene expression, and have the ability to infect both dividing and quiescent cells. Furthermore, AAV is not currently known to cause disease and therefore causes little to no toxicity and inflammation in vivo. These characteristics have led to AAV becoming a desirable vector for gene therapy applications.

Several methods of AAV vector production in cell lines are commonly used. One method utilises cell lines that stably harbour AAV rep/cap gene, as well as the gene of interest flanked by the AAV ITRs. The production of recombinant AAV particles is initiated by infection of the cells with wild type adenovirus. The adenovirus provides genes that are required to be expressed for AAV replication and virion production: E1A, E1B, E2A, E4 and the VA RNA. Although this method has been shown to be easily scaled up in cultures and produce AAV vectors with high titres, it is very challenging to completely remove the adenovirus from the AAV product. Contamination of wildtype adenovirus is highly undesirable in view of vector safety and specificity.

An alternative method of AAV vector production does not involve infection of the host cell with helper virus. Instead, host HEK293 cells are transiently co-transfected with 3 plasmids: (1) an AAV transfer vector carrying the gene of interest flanked by AAV ITRs; (2), a plasmid that carries the AAV rep/cap gene; and (3), a plasmid that provides the helper genes cloned from adenovirus. Although this transient transfection method generates high titres of AAV vectors that are free of adenovirus, the process is very labour-intensive and expensive.

All cell lines used in the manufacture of AAV vectors, such as AAV packaging and producer cell lines, must adhere to the quality requirements set out by the authoritative body (e.g. the European Medicines Agency (EMA) for Europe and the Food and Drug Administration (FDA) for the US). A key quality requirement for AAV packaging and producer cell lines is that they do not produce wild-type AAV or replication competent AAV (see "Reflection paper on quality, non-clinical and clinical issues related to the development of recombinant adeno-associated viral vectors", EMA, 24 Jun. 2010). A further key quality requirement is cell substrate stability. That is to say, for a given production to be prepared in the cell line, it is necessary to demonstrate that consistent production can be obtained with cells at the beginning and end of the intended span of use (see European Pharmacopoeia 7.0; section 5.2.3).

It is therefore an object of the present invention to provide a method of producing AAV vectors and making stable AAV packaging and producer cell lines which overcomes one or more of the disadvantages associated with existing methods.

SUMMARY OF THE INVENTION

The present inventors have developed a new way of making packaging and producer cell lines which involves the use of nucleic acid vectors comprising a non-mammalian origin of replication and the ability to hold at least 25 kilobases (kb) of DNA, such as bacterial artificial chromosomes, carrying all the adeno-associated virus (AAV) genes essential for AAV vector production. This allows integration of all the AAV genes required for production of recombinant AAV vector particles, and a selective antibiotic resistance gene, into the producer cell genome, ameliorating problems associated with transient transfection methods.

The use of a nucleic acid vector comprising a non-mammalian origin of replication and which has the ability to hold at least 25 kb of DNA (i.e. large-construct DNA) has several advantages. In the first instance, the vectors can first be manipulated in non-mammalian cells (e.g. microbial cells, such as bacterial cells) rather than mammalian host cells, making them much easier to work with (e.g. bacterial artificial chromosomes can first be manipulated in *E. coli*). Once the nucleic acid vector has been prepared, it can be introduced into a mammalian host cell and any cells into which the nucleic acid vector has integrated into one or several of the endogenous chromosomes can be selected for in order to isolate a stable cell line.

Introduction of the AAV construct into mammalian host cells also occurs in a single step, helping to reduce selection pressure and silencing timeframe. This allows for faster screening of potential packaging cells and reduces the cost of materials because only a single vector is used, rather than previous methods which use multiple plasmid vectors. In particular, use of this system reduces the cost of plasmid manufacture, reduces requirement for transfection reagents (e.g. Polyethylenimine [PEI]), reduces the amount of Benzonase™ treatment required (there is a reduced amount of DNA in the viral harvest, therefore less Benzonase™ is needed to remove the excess in downstream processing) and reduces costs of testing (there is no need to test for residual plasmid in the viral product).

Furthermore, because all the viral genes essential for AAV production (with or without the transfer vector containing the transgene to be packaged) are cloned contiguously within the same nucleic acid vector, when the vector is introduced into mammalian host cells, all of the genes incorporated in the vector will integrate at one locus within the endogenous mammalian host cell genome. This makes it easier to select for stable clones in which none of the required genes for AAV production have integrated into a region of the genome that can cause gene silencing. This might occur to one or more genes when the required AAV genes are provided on several plasmids which can integrate randomly at different loci within the host cell genome.

The use of nucleic acid vectors of the invention therefore provides advantages in the generation of AAV packaging and producer cell lines.

Therefore, according to a first aspect of the invention, there is provided an adeno-associated virus (AAV) producer cell comprising nucleic acid sequences encoding:

AAV rep/cap gene;
helper virus genes; and
a DNA genome of an AAV vector particle, wherein said nucleic acid sequences are all integrated together at a single locus within the AAV producer cell genome.

According to a further aspect of the invention, there is provided a nucleic acid vector comprising a non-mammalian origin of replication and the ability to hold at least 25 kilobases (kb) of DNA, characterized in that said nucleic acid vector comprises nucleic acid sequences encoding:

Adeno-associated virus (AAV) rep/cap gene, and
helper virus genes, wherein the nucleic acid sequences encoding the AAV rep/cap gene and each of the helper virus genes are arranged as individual expression cassettes within the nucleic acid vector.

According to a further aspect of the invention, there is provided a method of producing a stable AAV packaging cell line, comprising:

(a) introducing the nucleic acid vector as defined herein into a culture of mammalian host cells; and
(b) selecting within the culture for a mammalian host cell which has the nucleic acid sequences encoded on the vector integrated into an endogenous chromosome of the mammalian host cell.

According to a further aspect of the invention, there is provided an AAV packaging cell obtained by the method as defined herein.

According to a further aspect of the invention, there is provided a method of producing a replication defective AAV vector particle, comprising:

(a) introducing the nucleic acid vector as defined herein into a culture of mammalian host cells;
(b) selecting within the culture for a mammalian host cell which has the nucleic acid sequences encoded on the vector integrated into an endogenous chromosome of the mammalian host cell; and
(c) further culturing the selected mammalian host cell under conditions in which the replication defective AAV vector particle is produced.

According to a further aspect of the invention, there is provided a replication defective AAV vector particle obtained by the method as defined herein.

BRIEF DESCRIPTION OF THE FIGURES

FIG. 3: A schematic diagram showing the nucleic acid sequences of the shRNA designed to target rep mRNA molecules.

DETAILED DESCRIPTION OF THE INVENTION

Definitions

Figure 1:
FIG. 1: A general figure of an exemplary nucleic acid vector of the invention. The figure shows a bacterial artificial chromosome (BAC) construct containing the AAV viral genes (rep/cap) and helper virus genes (E2A, E4 and VA from Adenovirus 2 [Ad2]) separated by insulators (cHS4). The construct also contains an antibiotic resistance marker (ZeoR) and a translation initiation site (IRES).

Unless defined otherwise, all technical and scientific terms used herein have the same meaning as is commonly understood by one of skill in the art to which this invention belongs. All patents and publications referred to herein are incorporated by reference in their entirety.

The term "comprising" encompasses "including" or "consisting" e.g. a composition "comprising" X may consist exclusively of X or may include something additional e.g. X+Y.

The term "consisting essentially of" limits the scope of the feature to the specified materials or steps and those that do not materially affect the basic characteristic(s) of the claimed feature.

The term "consisting of" excludes the presence of any additional component(s).

The term "about" in relation to a numerical value x means, for example, x±10%, 5%, 2% or 1%.

The term "vector" or "nucleic acid vector" refers to a vehicle which is able to artificially carry foreign (i.e. exogenous) genetic material into another cell, where it can be replicated and/or expressed. Examples of vectors include non-mammalian nucleic acid vectors, such as bacterial artificial chromosomes (BACs), yeast artificial chromosomes (YACs), P1-derived artificial chromosomes (PACs), cosmids or fosmids.

The term "non-mammalian origin of replication" refers to a nucleic acid sequence where replication is initiated and which is derived from a non-mammalian source. This enables the nucleic acid vectors of the invention to stably replicate and segregate alongside endogenous chromosomes in a suitable host cell (e.g. a microbial cell, such as a bacterial or yeast cell) so that it is transmittable to host cell progeny, except when the host cell is a mammalian host cell. In mammalian host cells, nucleic acid vectors with non-mammalian origins of replication will either integrate into the endogenous chromosomes of the mammalian host cell or be lost upon mammalian host cell replication. For example, nucleic acid vectors with non-mammalian origins of replication such as bacterial artificial chromosomes (BAC), P1-derived artificial chromosome (PAC), cosmids or fosmids, are able to stably replicate and segregate alongside endogenous chromosomes in bacterial cells (such as E. coli), however if they are introduced into mammalian host cells, the BAC, PAC, cosmid or fosmid will either integrate or be lost upon mammalian host cell replication. Yeast artificial chromosomes (YAC) are able to stably replicate and segregate alongside endogenous chromosomes in yeast cells, however if they are introduced into mammalian host cells, the YAC will either integrate or be lost upon mammalian host cell replication. Therefore, in this context, the nucleic acid vectors of the invention act as reservoirs of DNA (i.e. for the genes essential for AAV vector production) which can be easily transferred into mammalian cells to generate stable cell lines for AAV vector production. Examples of non-mammalian origins of replication include bacterial origins of replications, such as oriC, oriV or oriS, or yeast origins of replication, also known as Autonomously Replicating Sequences (ARS elements).

The nucleic acid vectors of the present invention comprise a non-mammalian origin of replication and are able to hold at least 25 kilobases (kb) of DNA. In one embodiment, the nucleic acid vector has the ability to hold at least 30, 35, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340 or 350 kb of DNA. It will be understood that references to "ability to hold" has its usual meaning and implies that the upper limit for the size of insert for the nucleic acid vector is not less than the claimed size (i.e. not less than 25 kb of DNA).

The aim of the present invention is to include the genes essential for AAV packaging in a single construct (i.e. the nucleic acid vector). Therefore, the nucleic acid vectors of the invention, must be able to hold large inserts of DNA. For the avoidance of doubt, it will be understood that references to "nucleic acid vectors" or "artificial chromosomes" do not refer to natural bacterial plasmids (e.g. such as the plasmids currently used in transient transfection methods) because these are not able to hold at least 25 kb of DNA. The maximum size insert which a plasmid can contain is about 15 kb. Such nucleic acid vectors also do not refer to bacteriophages which generally only hold maximum inserts of 5-11 kb. Therefore, in one embodiment the nucleic acid vector of the invention is not a plasmid, bacteriophage or episome.

In one embodiment, the nucleic acid vector of the invention is not a bacteriophage.

The term "endogenous chromosomes" refers to genomic chromosomes found in the host cell prior to generation or introduction of an exogenous nucleic acid vector, such as a bacterial artificial chromosome.

The terms "transfection", "transformation" and "transduction" as used herein, may be used to describe the insertion of the non-mammalian or viral vector into a target cell. Insertion of a vector is usually called transformation for bacterial cells and transfection for eukaryotic cells, although insertion of a viral vector may also be called transduction. The skilled person will be aware of the different non-viral transfection methods commonly used, which include, but are not limited to, the use of physical methods (e.g. electroporation, cell squeezing, sonoporation, optical transfection, protoplast fusion, impalefection, magnetofection, gene gun or particle bombardment), chemical reagents (e.g. calcium phosphate, highly branched organic compounds or cationic polymers) or cationic lipids (e.g. lipofection). Many transfection methods require the contact of solutions of plasmid DNA to the cells, which are then grown and selected for a marker gene expression.

The term "promoter" refers to a sequence that drives gene expression. In order to drive a high level of expression, it may be beneficial to use a high efficiency promoter. Examples of suitable promoters may include a promoter such as the human cytomegalovirus (CMV) immediate early promoter, spleen focus-forming virus (SFFV) promoter, Rous sarcoma virus (RSV) promoter, or human elongation factor 1-alpha (pEF) promoter.

The term "selectable marker" refers to a gene that will help select cells actively expressing a nucleic acid sequence. Examples of suitable selection markers include, enzymes encoding resistance to an antibiotic (i.e. an antibiotic resistance gene), e.g., kanamycin, neomycin, puromycin, hygromycin, blasticidin, or zeocin. Another example of suitable selection markers are fluorescent proteins, for example green fluorescent protein (GFP), red fluorescent protein (RFP) or blue fluorescent protein (BFP).

"Gene amplification" refers to a process by which specific DNA sequences of the genome (i.e. genes) are disproportionately replicated in relation to the other sequences in the genome such that the amplified DNA sequences become present in a higher copy number than was initially present in the genome before such disproportionate replication. "Amplified" or "amplification" as used herein with reference to a gene or nucleic acid sequence refers to a gene or nucleic acid sequence present in two or more copies in a host cell line by virtue of gene amplification.

References to an "amplifiable selection marker gene" as used herein refers to a gene which permits the amplification of that gene under appropriate growth conditions. The amplifiable selection marker gene is capable of responding either to an inhibitor or lack of an essential metabolite by amplification to increase the expression product (i.e. the expression of the protein encoded by the amplifiable selection marker gene). In one embodiment, the amplifiable selection marker gene may be characterized as being able to complement an auxotrophic host.

The term "polyA signal" refers to a polyadenylation signal sequence, for example placed 3' of a transgene, which enables host factors to add a polyadenosine (polyA) tail to the end of the nascent mRNA during transcription. The polyA tail is a stretch of up to 300 adenosine ribonucleotides which protects mRNA from enzymatic degradation and also aids in translation. Accordingly, the nucleic acid vectors of the present invention may include a polyA signal sequence such as the human beta globin or rabbit beta globin polyA signals, the simian virus 40 (SV40) early or late polyA signals, the human insulin polyA signal, or the bovine growth hormone polyA signal. In one embodiment, the polyA signal sequence is the human beta globin polyA signal.

The term "intron sequence" refers to a nucleotide sequence which is removed from the final gene product by RNA splicing. The use of an intron downstream of the enhancer/promoter region and upstream of the cDNA insert has been shown to increase the level of gene expression. The increase in expression depends on the particular cDNA insert. Accordingly, the nucleic acid vector of the present invention may include introns such as human beta globin intron, rabbit beta globin intron II or a chimeric human beta globin-immunoglobulin intron. In one embodiment, the intron is a human beta globin intron and/or a rabbit beta globin intron II.

The term "packaging cell line" refers to a cell line with stably inserted AAV packaging genes, i.e. the rep and cap genes, and the required helper virus genes. Alternatively, the term "producer cell line" refers to a packaging cell line with a stably inserted AAV genome, e.g. containing a transgene of interest flanked by the two AAV inverted terminal repeats (ITRs). It will be understood by a person skilled in the art that the nucleic acid vectors described herein may be used to generate packaging cell lines (i.e. when at least the rep, cap and helper virus genes are present on the nucleic acid vector and incorporated into a host cell) or producer cell lines (i.e. when the nucleic acid vector additionally comprises the AAV genome to be incorporated into a host cell along with the rep and cap genes). It will further be understood that the packaging and/or producer cells described herein do not refer to cells in which the natural AAV provirus has been integrated.

The term "expression construct" or "expression cassette" as used herein refers to a functional expression unit, capable of driving the expression of one or more incorporated polynucleotides. Such cassettes usually include the polynucleotide and the components necessary for the transcription and translation of the polynucleotide. For example, the cassette may include a nucleic acid sequence (i.e. recombinant DNA) including a promoter, a translational initiation signal, a transcriptional terminator (e.g. a polyA sequence) and/or a self-cleaving peptide sequence (e.g. P2A sequence). In one embodiment, the individual expression cassette comprises a promoter and/or a transcriptional terminator. In one embodiment, the individual expression cassette comprises two genes separated by an IRES that are both transcribed from a single promoter. For the avoidance of doubt, references to such cassettes includes the rep/cap gene which produces several transcripts from 3 different promoters that are then spliced into 7 different proteins but cannot be separated from each other due to the compact nature of the AAV genome. Therefore, expression cassettes may comprise more than one promoter.

In one embodiment, all the expressions cassettes in the nucleic acid vector are arranged so that they transcribe in the same direction. This has previously been shown to improve overall expression of the expression cassettes in a construct (Throm et al., (2009) Blood 113: 5104-5110).

The term "stably transfected" refers to cell lines which are able to pass introduced AAV genes to their progeny (i.e. daughter cells), either because the transfected DNA has been incorporated into the endogenous chromosomes or via stable inheritance of exogenous chromosomes.

Nucleic Acid Vectors

According to one aspect of the invention, there is provided a nucleic acid vector comprising a non-mammalian origin of replication and the ability to hold at least 25 kilobases (kb) of DNA, characterized in that said nucleic acid vector comprises nucleic acid sequences encoding:
  Adeno-associated virus (AAV) rep/cap gene; and
  helper virus genes,
  wherein the nucleic acid sequences encoding the AAV rep/cap gene and each of the helper virus genes are arranged as individual expression cassettes within the nucleic acid vector.

Current methods for generating AAV vectors involve transient transfection of the viral genes into a host cell. However, many disadvantages have been associated with this method because it is costly and laborious. One solution would be to engineer a packaging cell line that stably incorporates the AAV packaging genes to avoid the problems associated with transient transfection.

By including all of the genes required for AAV vector production in the nucleic acid vector, all the required genes for AAV packaging can be inserted into the endogenous chromosomes of a mammalian host cell in one single step. Therefore, the use of a nucleic acid vector, as proposed herein, would reduce selection pressure, reduce the silencing timeframe and allow for faster screening of potential packaging cells. Furthermore, the genes required for AAV vector production included on the nucleic acid vector would all be integrated into the endogenous chromosomes of the mammalian host cell at a single locus. This would reduce the risk of individual viral genes becoming silenced and ensure that all the viral genes are evenly expressed.

It will be understood that the nucleic acid vector construct may integrate more than once in the host cell genome at multiple different locations on different chromosomes (albeit with all of the encoded nucleic acid sequences present in a single locus). This may be beneficial for increasing expression levels of the transgenes and could potentially improve AAV titres.

In one embodiment, the nucleic acid vector additionally comprises nucleic acid sequences which encode the DNA genome of the AAV vector particle. When this nucleic acid sequence is transcribed, it will become encapsidated within the AAV vector particle produced by the cell and therefore act as the AAV vector particle's "genome". It will be understood that the DNA genome of the AAV vector particle is usually included on the "transfer plasmid" used in transient transfection methods. The transfer plasmid generally contains a promoter (such as CMV) operably linked to the transgene (and optionally a polyadenylation [polyA] signal), between the two AAV ITRs. Therefore, reference to the "DNA genome of the AAV vector particle" as used herein refers to a nucleic acid sequence (usually encoding the transgene of interest) flanked by AAV ITRs. Thus, in one embodiment, the DNA genome of the AAV vector particle comprises one or more transgenes encoded between two AAV ITRs.

In one embodiment, multiple copies of the DNA genome of the AAV vector particle (i.e. the transfer plasmid) are included in the nucleic acid vector. Multiple copies of the transfer plasmid are expected to result in higher viral vector titre. For example, the nucleic acid vector may include two or more, such as three, four, five, six, seven, eight, nine or ten or more copies of the DNA genome of the AAV vector particle (i.e. the transfer plasmid).

In one embodiment, the nucleic acid vector contains one or a plurality of recombination site(s). This allows for target sequences to be integrated into the endogenous chromosomes of the mammalian host cell in a site-specific manner in the presence of a recombinase enzyme. The recombinase enzyme catalyses the recombination reaction between two recombination sites.

Many types of site-specific recombination systems are known in the art, and any suitable recombination system may be used in the present invention. For example, in one embodiment the recombination site(s) are selected or derived from the int/att system of lambda phage, the Cre/lox system of bacteriophage P1, the FLP/FRT system of yeast, the Gin/gix recombinase system of phage Mu, the Cin recombinase system, the Pin recombinase system of E. coli and the R/RS system of the pSR1 plasmid, or any combination thereof. In a further embodiment, the recombination site is an att site (e.g. from lambda phage), wherein the att site permits site-directed integration in the presence of a lambda integrase. It will be understood that the reference to "lambda integrase" includes references to mutant integrases which are still compatible with the int/att system, for example the modified lambda integrases described in WO 2002/097059.

In one embodiment, the nucleic acid vector is selected from: a bacterial artificial chromosome (BAC), a yeast artificial chromosome (YAC), a P1-derived artificial chromosome (PAC), fosmid or a cosmid. In a further embodiment, the nucleic acid vector is a bacterial artificial chromosome (BAC).

Bacterial Artificial Chromosomes

The term "bacterial artificial chromosome" or "BAC" refers to a DNA construct derived from bacterial plasmids which is able to hold a large insert of exogenous DNA. They can usually hold a maximum DNA insert of approximately 350 kb. BACs were developed from the well characterised bacterial functional fertility plasmid (F-plasmid) which contains partition genes that promote the even distribution of plasmids after bacterial cell division. This allows the BACs to be stably replicated and segregated alongside endogenous bacterial genomes (such as E. coli). The BAC usually contains at least one copy of an origin of replication (such as the oriS or oriV gene), the repE gene (for plasmid replication and regulation of copy number) and partitioning genes (such as sopA, sopB, parA, parB and/or parC) which ensures stable maintenance of the BAC in bacterial cells. BACs are naturally circular and supercoiled which makes them easier to recover than linear artificial chromosomes, such as YACs. They can also be introduced into bacterial host cells relatively easily, using simple methods such as electroporation.

In one embodiment, the bacterial artificial chromosome comprises an oriS gene. In one embodiment, the bacterial artificial chromosome comprises a repE gene. In one embodiment, the bacterial artificial chromosome comprises partitioning genes. In a further embodiment, the partitioning genes are selected from sopA, sopB, parA, parB and/or parC. In a yet further embodiment, the bacterial artificial chromosome comprises a sopA and sopB gene.

BAC for use in the present invention may be obtained from commercial sources, for example the pSMART BAC from LUCIGEN™ (see Genome Accession No. EU101022.1 for the full back bone sequence). This BAC contains the L-arabinose "copy-up" system which also contains the oriV medium-copy origin of replication, which is active only in the presence of the TrfA replication protein. The gene for TrfA may be incorporated into the genome of bacterial host cells under control of the L-arabinose inducible promoter araC-P$_{BAD}$ (see Wild et al. (2002) *Genome Res.* 12(9): 1434-1444). Addition of L-arabinose induces expression of TrfA, which activates oriV, causing the plasmid to replicate to up to 50 copies per cell.

Yeast Artificial Chromosomes

The term "yeast artificial chromosome" or "YAC" refers to chromosomes in which yeast DNA is incorporated into bacterial plasmids. They contain an autonomous replication sequence (ARS) (i.e. an origin of replication), a centromere and telomeres. Unlike BACs, the YAC is linear and therefore contains yeast telomeres at each end of the chromosome to protect the ends from degradation as it is passed onto host cell progeny. YACs can hold a range of DNA insert sizes; anything from 100-2000 kb.

P1-Derived Artificial Chromosomes

The term "P1-derived artificial chromosome" or "PAC" refers to DNA constructs derived from the DNA of the P1-bacteriophage and bacterial F-plasmid. They can usually hold a maximum DNA insert of approximately 100-300 kb and are used as cloning vectors in E. coli. PACs have similar advantages as BACs, such as being easy to purify and introduce into bacterial host cells.

Cosmids and Fosmids

The term "cosmid" refers to DNA constructs derived from bacterial plasmids which additionally contain cos sites derived from bacteriophage lambda. Cosmids generally contain a bacterial origin of replication (such as oriV), a selection marker, a cloning site and at least one cos site. Cosmids can usually accept a maximum DNA insert of 40-45 kb. Cosmids have been shown to be more efficient at infecting E. coli cells than standard bacterial plasmids. The term "fosmids" refers to non-mammalian nucleic acid vectors which are similar to cosmids, except that they are based on the bacterial F-plasmid. In particular, they use the F-plasmid origin of replication and partitioning mechanisms to allow cloning of large DNA fragments. Fosmids can usually accept a maximum DNA insert of 40 kb.

It will be understood that the nucleic acid sequences encoding the replication defective AAV vector particle may be the same as, or derived from, the wild-type genes, i.e. the sequences may be genetically or otherwise altered versions of sequences contained in the wild-type virus. Therefore, the viral genes incorporated into the nucleic acid vectors or host cell genomes, may also refer to codon-optimised versions of the wild-type genes.

Adeno-Associated Virus

Adeno-associated viruses (AAV) is part of the genus Dependoparvovirus, which belongs to the family Parvoviridae. AAV is a small, non-enveloped, icosahedral virus with single-stranded DNA (ssDNA) genome of approximately 4.7 kilobases (kb) to 6 kb in length. Several serotypes have been discovered, with AAV serotype 2 (AAV2) as the most extensively examined serotype so far.

The AAV genome consists of two open reading frames, rep and cap, flanked by two 145 base inverted terminal repeats (ITRs). These ITRs base pair to allow for synthesis of the complementary DNA strand. The rep and cap genes (which may also be collectively referred to as the rep/cap gene) are translated to produce multiple distinct proteins: the rep gene encodes the proteins Rep78, Rep68, Rep52, Rep40 which are required for the AAV life cycle; the cap gene encodes VP1, VP2, VP3 which are the capsid proteins. When constructing an AAV transfer plasmid, the transgene is placed between the two ITRs, and rep and cap are supplied in trans. This is to ensure that the AAV produced by the host cell is replication defective.

The AAV rep coding sequences encode at least those replication proteins that are necessary for viral genome replication and packaging into new virions. The rep gene will generally encode at least one large rep protein (i.e. Rep78/68) and one small rep protein (i.e. Rep52/40), however in the embodiments described herein, the rep gene does not need to encode all of the AAV rep proteins. Therefore, in one embodiment, the rep proteins comprise the Rep78 protein and the Rep52 and/or Rep40 proteins. In an alternative embodiment, the rep proteins comprise the Rep68 and the Rep52 and/or Rep40 proteins. In a further embodiment, the rep proteins comprise the Rep68 and Rep52 proteins, Rep68 and Rep40 proteins, Rep78 and Rep52 proteins, or Rep78 and Rep40 proteins. In a yet further embodiment, the rep proteins comprise the Rep78, Rep68, Rep52 and Rep40 proteins.

The AAV cap coding sequences encode the structural proteins that form a functional AAV capsid (i.e. can package DNA and infect target cells). Typically, the cap coding sequences will encode all of the AAV capsid subunits, but less than all of the capsid subunits may be encoded as long as a functional capsid is produced. In one embodiment, the cap proteins comprise VP1, VP2 and/or VP3.

The AAV ITR sequences comprise 145 bases each and are the only cis-acting elements necessary for AAV genome replication and packaging into the capsid. Typically, the ITRs will be at the 5' and 3' ends of the vector genome and flank the heterologous nucleic acid (transgene), but need not be contiguous thereto. The ITRs can be the same or different from each other.

An AAV ITR may be from any AAV, including but not limited to serotypes 1, 2, 3a, 3b, 4, 5, 6, 7, 8, 9, 10, 11, or 13, snake AAV, avian AAV, bovine AAV, canine AAV, equine AAV, ovine AAV, goat AAV, shrimp AAV, or any other AAV now known or later discovered. An AAV ITR need not have the native terminal repeat sequence (e.g. a native AAV ITR sequence may be altered by insertion, deletion, truncation and/or missense mutations), as long as the terminal repeat mediates the desired functions, e.g., replication, virus packaging, and/or integration, and the like.

References to AAV as used herein, includes, but is not limited to, AAV serotype 1 (AAV1), AAV serotype 2 (AAV2), AAV serotype 3 (including serotypes 3A and 3B) (AAV3), AAV serotype 4 (AAV4), AAV serotype 5 (AAV5), AAV serotype 6 (AAV6), AAV serotype 7 (AAV7), AAV serotype 8 (AAV8), AAV serotype 9 (AAV9), AAV serotype 10 (AAV10), AAV serotype 11 (AAV11), AAV serotype 12 (AAV12), AAV serotype 13 (AAV13), snake AAV, avian AAV, bovine AAV, canine AAV, equine AAV, ovine AAV, goat AAV, shrimp AAV, and any other AAV now known or later discovered. See, e.g. Fields et al. Virology, volume 2, chapter 69 (4th ed., Lippincott-Raven Publishers).

References to AAV may include artificial AAV serotypes which include, without limitation, AAV with a non-naturally occurring capsid protein. Such an artificial capsid may be generated by any suitable technique, using one AAV serotype sequence (e.g. a fragment of a VP1 capsid protein) in combination with heterologous sequences which may be obtained from another AAV serotype (known or novel), non-contiguous portions of the same AAV serotype, from a non-AAV viral source, or from a non-viral source. An artificial AAV serotype may be, without limitation, a chimeric AAV capsid, a recombinant AAV capsid, or a "humanized" AAV capsid.

In one embodiment, the nucleic acid sequences encoding the rep/cap gene and/or the DNA genome of the AAV vector particle (i.e. the AAV nucleic acid sequences) are derived from AAV1, AAV2, AAV3, AAV4, AAV5, AAV6, AAV7, AAV8, AAV9, AAV10, AAV11, AAV12, AAV13 or combinations thereof. In a further embodiment, the nucleic acid sequences encoding the rep/cap gene and/or the DNA genome of the AAV vector particle are derived from AAV2, AAV5 and/or AAV9.

Alternatively, in one embodiment the rep sequences are from an AAV serotype which differs from that which is providing the cap sequences. Therefore, in one embodiment, the rep sequences are fused in frame to cap sequences of a different AAV serotype to form a chimeric AAV vector. For example, in one embodiment, the rep gene is derived from AAV2 and the cap gene is derived from AAV2 or AAV5 to produce AAV2-like and AAV5-like particles, respectively. These may be named rep2cap2 and rep2cap5.

The genomic sequences of various serotypes of AAV, as well as the sequences of the native ITRs, rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, AY631966, AX753250, EU285562, NC_001358, NC_001540, AF513851, AF513852 and AY530579; the disclosures of which are incorporated by reference herein for teaching AAV nucleic acid and amino acid sequences.

Tissue specificity is thought to be determined by the capsid serotype and therefore pseudotyping of AAV vectors can be used to alter their tropism range. This makes AAV a useful system for preferentially transducing specific cell types. Table 1 summaries the optimal serotypes for transduction of specific tissues:

TABLE 1

Optimal AAV serotype(s) for transduction of a given organ

| Tissue | Optimal Serotype |
| --- | --- |
| CNS | AAV1, AAV2, AAV4, AAV5, AAV8, AAV9 |
| Heart | AAV1, AAV8, AAV9 |
| Kidney | AAV2 |
| Liver | AAV2, AAV3, AAV5, AAV7, AAV8, AAV9, AAV10 |
| Lung | AAV4, AAV5, AAV6, AAV9 |
| Pancreas | AAV8 |
| Photoreceptor Cells | AAV2, AAV5, AAV8 |
| RPE (Retinal Pigment Epithelium) | AAV1, AAV2, AAV4, AAV5, AAV8 |
| Skeletal Muscle | AAV1, AAV6, AAV7, AAV8, AAV9 |
| Brain | AAV4, AAV9, AAV10 |

References to "pseudotyping" refer to the mixing of a capsid and genome from different viral serotypes. These serotypes are denoted using a slash, for example, AAV2/5 indicates a virus containing the genome of AAV serotype 2 packaged in the capsid from AAV serotype 5. Use of these pseudotyped viruses can improve transduction efficiency, as well as alter tropism. For example, AAV2/5 targets neurons that are not efficiently transduced by AAV2/2, and is distributed more widely in the brain, indicating improved transduction efficiency. Many of these hybrid viruses have been well characterized in the art.

The terms AAV vector, AAV particle, AAV vector particle, recombinant AAV particle, recombinant AAV vector particle and rAAV are used interchangeably and as used herein refer to the AAV capsid, with or without a DNA genome comprising ITRs as produced by a producer cell or packaging cell, respectively.

Helper Virus Genes

In addition to rep and cap proteins, AAV requires a helper virus or plasmid containing genes necessary for AAV replication because AAV does not have the ability to replicate on its own. In the absence of helper viruses, AAVs may incorporate into the host cell genome, particularly at a specific site of chromosome 19. Helper virus sequences necessary for AAV replication are known in the art, for example see Cell & Gene Therapy Insights, "Gene Therapy And Viral Vectors: Advances and Challenges". Typically, these sequences will be provided by a helper adenovirus or herpesvirus vector. The helper virus genes encode proteins and non-coding RNA.

In one embodiment, the helper virus genes are derived from adenovirus. In a further embodiment, the adenovirus is selected from adenovirus 2 and adenovirus 5.

In one embodiment, the helper virus genes comprise all or part of E4, E2a and VA genes derived from adenovirus, in particular adenovirus 2. It has been found that not all of the native adenovirus genes are required for AAV replication, for example only the E4 34 kD protein encoded by open reading frame 6 (ORF 6) of the E4 gene is required for AAV replication. Therefore, in a further embodiment, the helper virus genes comprise an E4 ORF6 coding region, an adenovirus E2a 72 kD coding region (coding for the E2a 72 kD DNA-binding protein) and a VA gene. In a yet further embodiment, the helper virus genes additionally comprise adenovirus E1a and E1b genes.

In an alternative embodiment, the helper virus genes are derived from herpesvirus. In a further embodiment, the herpesvirus is selected from: herpes simplex virus (HSV), Epstein-Barr Virus (EBV), cytomegalovirus (CMV) and pseudorabies virus (PRV).

Each of the helper virus genes may be controlled by the respective original promoter or by heterologous promoters.

By integrating the helper virus genes required for AAV vector production into the nucleic acid vector/host cell, it will be understood that this method may be considered a helper virus-free method because it does not require co-infection with a wild-type helper virus. This therefore avoids contamination of wild-type helper virus (e.g. adenovirus) which is highly undesirable in view of vector safety and specificity.

Additional Components

The nucleic acid vectors of the invention may comprise further additional components. These additional features may be used, for example, to help stabilize transcripts for translation, increase the level of gene expression, and turn on/off gene transcription.

The AAV vector particles produced by the invention may be used in methods of gene therapy. Therefore, in one embodiment, the nucleic acid vector additionally comprises one or more transgenes (which may also be referred to as the heterologous nucleic acid). This transgene may be a therapeutically active gene which encodes a gene product which may be used to treat or ameliorate a target disease. This may include, for example, when a target gene is not expressed correctly in the host cell, therefore a corrected version of the target gene is introduced as the transgene. Therefore, the transgene may be a gene of potential therapeutic interest. The transgene may have been obtained from another cell type, or another species, or prepared synthetically. Alternatively, the transgene may have been obtained from the host cell, but operably linked to regulatory regions which are different to those present in the native gene. Alternatively, the transgene may be a different allele or variant of a gene present in the host cell.

The transgene may encode, for example, an antisense RNA, a ribozyme, a protein (for example a tumour suppressor protein), a toxin, an antigen (which may be used to induce antibodies or helper T-cells or cytotoxic T-cells) or an antibody (such as a single chain antibody). Any gene that is flanked by the ITRs can effectively be packaged into an AAV capsid as long as the genome is smaller than 5 kilobases (kb) in size. Therefore, in one embodiment the transgene is less than 5 kb long, such as less than 4.5, 4, 3.5, 3, 2.5, 2, 1.5 or 1 kb long.

Multiple copies of the transfer plasmid containing the transgene are expected to result in higher transgene production, therefore in one embodiment, the nucleic acid vector comprises multiple copies of the transgene, such as two or more, in particular three or more, copies of the transgene.

In some cases, more than one gene product is required to treat a disease, therefore in a further embodiment, the nucleic acid vector additionally comprises two or more, such as three or more, or four or more, different transgenes.

The aim of gene therapy is to modify the genetic material of living cells for therapeutic purposes, and it involves the insertion of a functional gene into a cell to achieve a therapeutic effect. The AAV vector produced using the nucleic acid vectors and host cells described herein can be used to transduce target cells and induce the expression of the gene of potential therapeutic interest. The AAV vector can therefore be used for treatment of a mammalian subject, such as a human subject, suffering from a condition including but not limited to, inherited disorders, cancer, and certain viral infections.

The transgene can encode any polypeptide or RNA that is desirably produced in a cell in vitro, ex vivo, or in vivo. For example, the AAV vectors may be introduced into cultured cells and the expressed gene product isolated therefrom.

It will be understood by those skilled in the art that the nucleic acid sequences can be operably associated with appropriate control sequences. For example, the nucleic acid sequences can be operably associated with expression control elements, such as transcription/translation control signals, origins of replication, polyadenylation signals, internal ribosome entry sites (IRES), promoters, and/or enhancers, and the like.

In one embodiment, the nucleic acid vector additionally comprises a transcription regulation element. For example, any of the elements described herein may be operably linked to a promoter so that expression can be controlled. In one embodiment, the promoter is a viral promoter. In one embodiment, the promoter is a high efficiency promoter, such as a CMV promoter. This promoter has the advantage of promoting a high level of expression of the elements encoded on the non-mammalian nucleic acid vector. In a further embodiment, the CMV promoter comprises a sequence derived from the human cytomegalovirus strain AD169. This sequence is available at Genome Accession No. X17403, for example from base pairs 173731 to 174404. In an alternative embodiment, the promoter is a SV40 late promoter from simian virus 40. Promoters referred to herein may include known promoters, in whole or in part, which may be constitutively acting or inducible, e.g. in the presence of a regulatory protein.

Inducible expression control elements are typically advantageous in those applications in which it is desirable to provide regulation over expression of the nucleic acid sequence(s). Inducible promoter/enhancer elements for gene delivery can be tissue-specific, such as muscle specific (including cardiac, skeletal and/or smooth muscle specific), neural tissue specific (including brain-specific), eye specific (including retina-specific and cornea-specific), liver specific, bone marrow specific, pancreatic specific, spleen specific or preferred and lung specific promoter/enhancer elements. Other inducible promoter/enhancer elements include hormone-inducible and metal-inducible elements. Exemplary inducible promoter/enhancer elements include, but are not limited to, a Tet on/off element, a RU486-inducible promoter, an ecdysone-inducible promoter, a rapamycin-inducible promoter, and a metallothionein promoter.

In one embodiment, the promoter additionally comprises at least one Tet operon. A Tet operon (Tetracycline-Controlled Transcriptional Activation) may be used in a method of inducible gene expression, wherein transcription is reversibly turned on or off in the presence of the antibiotic tetracycline or one of its derivatives (e.g. doxycycline). In nature, the Ptet promoter expresses TetR, the repressor, and TetA, the protein that pumps tetracycline antibiotic out of the cell. In the present invention, the Tet operon may be present or absent, for example, in one embodiment the Tet operon may be present in the promoter.

The Tet operon system may be used to control expression of the viral sequences contained within the nucleic acid vector. Briefly, the Tet repressor protein blocks expression by binding to the Tet operon site which is introduced into the promoter. Therefore, when the Tet repressor is bound to the Tet operon, there is no gene expression. On addition of tetracycline or doxycyclin, the Tet repressor is sequestered allowing promoter activity, therefore gene expression is switched on. Tet operon systems are widely available, such as the Tet operon used in the pcDNA™4/TO mammalian expression vector available from Invitrogen.

In one embodiment, the nucleic acid vector additionally comprises a tetracycline resistance operon repressor protein ("Tet repressor" or "TetR"). In a further embodiment, the Tet repressor is codon optimised.

In one embodiment, the nucleic acid vector additionally comprises an insulator, such as a chromatin insulator. The term "insulator" refers to a genetic sequence which blocks the interaction between promoters and enhancers. In a further embodiment, the insulator (such as a chromatin insulator) is present between each of the viral nucleic acid sequences (i.e. between the nucleic acid sequences encoding: (i) AAV rep/cap gene; (ii) helper virus genes; and (iii) the DNA genome of the AAV vector particle). In a further embodiment, an insulator may be present between each of the helper virus genes (e.g. E1A, E1B, E2A, E4 and/or VA). This helps to prevent promoter interference (i.e. where the promoter from one transcription unit impairs expression of an adjacent transcription unit) between adjacent viral nucleic acid sequences. This is also thought to help minimise the risk of recombination between viral sequences to generate replication-competent virus. Furthermore, it is also thought to help reduce silencing of nearby expression cassettes when they are stably integrated into the cells genome (Moriarity et al., (2013) Nucleic Acids Res. 41: e92; Yahata et al., (2007) *J. Mol. Biol.* 374: 580-590).

It will be understood that if the insulators are present in the nucleic acid vector between each of the nucleic acid sequences, then these may be arranged as individual expression cassettes within the nucleic acid vector. For example, each nucleic acid sequence (i.e. encoding the AAV vector particle) has its own promoter and/or an intron and/or polyA signal.

In one embodiment, the chromatin insulator has at least 90% sequence identity, for example at least 95% sequence identity, to the chicken (*Gallus gallus*) HS4 (cHS4) insulator sequence (for example see Genome Accession No. U78775.2, base pairs 1 to 1205). In a further embodiment, the insulator comprises two tandem cHS4 insulator sequences (approximately 2.4 kilobases), i.e. 2×cHS4.

In one embodiment, the nucleic acid vector comprises nucleic acid sequences encoding shRNA, which targets the rep transcripts (rep mRNA molecule). In this way, it is possible to control the expression of Rep proteins. Expression of the shRNA itself may be under the control of an inducible promoter. The advantage of controlling expression of Rep proteins at a transcript level is that it is possible to maintain all of the native promoters of the rep and cap genes (P5, P19 and P40) in order to maintain the correct stoichiometry of the various rep and cap transcripts required for efficient AAV vector production. It also means that the integrity of the rep and cap genes are not affected as they are not required to be modified.

In a further embodiment, the nucleic acid vector comprises nucleic acid sequences encoding shRNA, which targets the E1A transcripts. The shRNA targeting E1A transcripts provide an additional level of control of Rep expression, acting indirectly through control of E1A expression. This is particularly advantageous in cell lines that constitutively express the adenovirus E1A helper virus gene. The adenovirus E1A helper gene product activates the promoters of other adenovirus helper genes such as E1B, E2 and E4, as well as binding to the host protein YY1 to enable activation of the AAV P5 promoter which is used to express the Rep proteins (Qiao et al. (2002) J. Virol. 76:1904).

A further advantage to controlling the expression of E1A is the indirect control of E4 expression, which is known to be toxic to the host cell as a results of its ability to induce apoptosis (Lavoie et al. (1998) JCB 140:637; Shtrichman and Kleinberger (1998) J. Virol. 72:2975). During AAV vector particle production, expression of the anti-E1A shRNA can be blocked, enabling expression of both E1A and E4 it regulates, activating the helper functions that are required for efficient AAV vector production.

In one embodiment, the nucleic acid sequence encoding the shRNA targeting the AAV rep mRNA molecule or the E1A mRNA molecule is micro-RNA adapted, for example, to enable transcription by RNA polymerase II. By micro-RNA adapted, it is meant that micro-RNA sequences are added upstream of the sense strand and/or downstream of the guide strand of the shRNA.

In one embodiment, the shRNA targeting the AAV rep mRNA binds to one or more of the AAV rep mRNA molecules encoding Rep78, Rep68, Rep52 and Rep40 proteins. In one embodiment, the shRNA targeting the AAV rep mRNA binds to the AAV rep mRNA molecules encoding Rep78 and Rep68, proteins. In a further embodiment, the shRNA binds to all of the rep mRNA molecules encoding Rep78, Rep68, Rep52 and Rep40 proteins.

In one embodiment, the nucleic acid sequence encoding the shRNA targeting the AAV rep mRNA molecule comprises 5'-TTTGACGTAGAATTCATGCTC-3' (SEQ ID NO: 7). This sequence is the targeting strand (also known as the guide strand) sequence. The skilled person will know that an shRNA, being a hairpin, also requires the complementary sense strand sequence and a loop sequence between them. The targeting strand is 3' to the sense strand in order to ensure that the targeting strand is the one loaded into the RISC.

A region of the AAV2 rep gene (nucleotides 190-540 of wild-type AAV2) was identified as a cis-acting Rep-dependent element (CARE). CARE was shown to augment replication and encapsidation of the AAV DNA genome when present in cis. This may be by producing more DNA copies of rep and cap genes. CARE was also shown to be involved in the amplification of integrated sequences in the presence of adenovirus and Rep proteins (Nony et al. (2001) J. Virol. 75:9991; Tessier et al. (2001) J. Virol. 75:375). CARE is bound by Rep protein and has been shown to be the site of initiation of the amplification of the AAV genome during viral replication and packaging. Double-stranded extrachromosomal copies of the AAV genome are produced, amplifying the genome around 100× in experimental models. Placing this element next to the rep-targeting shRNA (or microRNA-adapted shRNA) will mean that this element will also be amplified along with the AAV genome. Therefore, when Rep is expressed, extra copies of the DNA sequence encoding the shRNA that targets AAV rep mRNA molecules will also be produced, thereby creating a self-regulating feedback loop of Rep repression.

Therefore, in one embodiment, the nucleic acid sequence encoding the shRNA targeting the AAV rep mRNA molecule and/or the E1A mRNA molecule is located adjacent to or in close proximity to a nucleic acid sequence encoding a cis-acting Rep-dependent Element (CARE) (i.e. nucleotides 190-540 of wild-type AAV2). By close proximity, it is meant sufficiently close to cause amplification of the nucleic acid sequence encoding the shRNA. In a further embodiment, the nucleic acid sequence encoding CARE is located 3' to the nucleic acid sequence encoding the shRNA in reverse orientation. By adding the CARE sequence 3' to the nucleic acid sequence encoding the shRNA, it is possible to ensure that of the stretch of nucleic acid sequence encoding shRNA amplified by the CARE, only those sequences comprising the full-length shRNA and promoter will be transcribed. This will help prevent overloading of the endogenous Drosha proteins with partial shRNA sequences.

The skilled person will be aware of methods available in the art for designing effective shRNAs against a specific target sequences, such as the mRNA molecules encoded by the AAV rep and cap genes. For example, criteria for effective shRNA design is outlined in Dow et al. (Dow et al. (2012) Nat. Protoc. 7:374). Furthermore, an online tool that finds and ranks shRNA target sequences that conform to the criteria for effective shRNA as outlined in Dow et al. is available as referenced in Adams et al. (Adams et al. (2017), Biomaterials 139:102).

Once the shRNA plasmid has been prepared and introduced into the cells, effective knockdown of the Rep proteins may be confirmed using methods well known in the art, for example by quantitative PCR analysis or Western blotting as described in Moore et al. (2010).

In one embodiment, expression of shRNA targeting rep transcripts and/or shRNA targeting E1A transcripts is under the control of a Ptet promoter. For example, a "tet-off" system may be used to express the genes required for AAV vector production. The tet-responsive transactivator protein, tTA, would be constitutively expressed from the construct. Under normal cell culture conditions, the tTA protein would bind the tet-operon containing promoter and activate the transcription of the rep-targeting shRNA, knocking down expression of Rep in the cells. When the cells reach the correct density for AAV vector particle production to proceed, addition of doxycycline (DOX) to the cells would de-stabilise the tTA transactivator protein such that the transcription of the shRNA targeting rep transcripts would cease, allowing Rep to be expressed by the cells.

A Ptet promoter with low background expression when in the "off" state, while retaining high transcriptional activation levels in the "on" state is Ptet-T6 described by Loew et al. (Loew et al., (2010) BMC Biotechnology 10: 81). Like the original tet-responsive promoter, Ptet-1, and its improved commercially available derivative, Ptet-14 (also known as Ptight), Ptet-T6 contains 7 tet operon binding sequences in tandem upstream of a minimal CMV immediate early promoter and a modified 5' untranslated sequence from turnip yellow mosaic virus. In one embodiment, the Ptet promoter is Ptet-T6.

In one embodiment, the nucleic acid vector additionally comprises a selectable marker. This allows the cells which have incorporated the nucleic acid sequences encoding a replication defective AAV vector particle to be selected. In a further embodiment, the selectable marker is a drug resistance gene, such as an antibiotic resistance gene, e.g. a zeocin, kanamycin or puromycin resistance gene, in particular a zeocin (ZeoR) resistance gene. In a yet further embodiment, the zeocin resistance gene is derived from the *Streptoalloteichus hindustans ble* gene, for example see Genome Accession No. X52869.1 from base pairs 3 to 377.

The natural phenomenon of gene amplification has been exploited in the biopharmaceutical industry as a way of increasing the titre of a recombinant product produced by a cell line. Where a recombinant gene has been integrated into the host cell's genome, the copy number of the recombinant gene and concomitantly the amount of recombinant protein expressed can be increased by selecting for cell lines in which the recombinant gene has been amplified after integration into the host cell genome. Therefore, in one embodiment, the selectable marker is an amplifiable selection marker.

Gene amplification may be induced by stably transfecting a host cell with an amplifiable selection marker gene. The stably transfected host cells are subjected to increasing concentrations of a toxic drug, which is known to inhibit the amplifiable selection marker. For example, the transfected cells may be cultured in a medium which contains the toxic drug at a concentration to achieve killing of greater than 98% of the cells within 3 to 5 days after plating the parent cells (i.e. non-transfected cells) in medium containing the toxic drug. Through such inhibition, populations of cells can be selected that have increased expression levels of the amplifiable selection marker and, consequently, resistance to the drug at the concentration employed.

The nucleic acid vector of the present invention allows all of the expression cassettes contained therein (i.e. nucleic acid vector DNA) to be integrated together at a single locus within the host cell genome. As the process of gene amplification causes amplification of the amplifiable selection marker gene and surrounding DNA sequences, the remaining DNA sequences in the integrated nucleic acid vector DNA will also be amplified. In this way, by using the nucleic acid vector of the invention, it is possible to provide a process for gene amplification of viral vector genes stably integrated into a host cell genome.

Each amplifiable selection marker has an associated selection agent (i.e. a toxic drug), which is added to the cell culture media during amplification and selection regimes. Suitable amplifiable selection marker/selection agent combinations include adenosine deaminase/deoxycoformycin, aspartate transcarbamylase/N (phosphoacetyl)-L-aspartate, dihydrofolate reductase/methotrexate, glutamine synthetase/ methionine sulphoximine, metallthionein-1/heavy metal.

In one embodiment, the amplifiable selection marker gene and/or the selectable marker is provided in an expression cassette.

In one embodiment, the amplifiable selection marker is dihydrofolate reductase (DHFR). The DHFR selection method involves incorporating the dhfr gene (amplifiable selection marker gene) to the nucleic acid vector thereby inducing a DHFR selection pressure to the other expression cassettes within the nucleic acid vector. The host cell is transfected with the nucleic acid vector and grown in the presence of increasing concentrations of DHFR inhibitor, methotrexate (MTX), to select for cells which have amplified the dhfr gene integrated into the host genome and concomitantly, the remaining integrated nucleic acid vector DNA.

In one embodiment, the dhfr gene comprises at least 60% sequence identity, such as at least 70%, 80%, 90% or 100% sequence identity to Genome Accession No. NM_010049.3

In another embodiment, the amplifiable selection marker is glutamine synthetase (GS). The GS selection method involves incorporating the gs gene to the nucleic acid vector, thereby inducing a GS selection pressure to the other expression cassettes within the nucleic acid vector. The host cell is transfected with the nucleic acid vector and grown in the presence of increasing concentrations of GS inhibitor methionine sulfoximine (MSX) to select for cells which have amplified the gs gene integrated into the host genome and concomitantly, the remaining integrated nucleic acid vector DNA.

The expression construct comprising nucleic acid sequences of the gs gene may contain nucleic acid sequences of expression constructs encoding gs gene known in the art (e.g. WO874462, which the sequences contained therein are incorporated herein by reference).

By using the amplifiable selection marker and associated selection agent in this way, followed by a culture period to allow the selection of cells that grow in the new (increased) concentration of the associated agent, the area of the genome harbouring the selection pressure can amplify, thereby increasing the copy number of the amplifiable selection marker. Consequently, when the expression cassettes of the nucleic acid vector comprising the viral genes are integrated into the host genome at a single locus together with an expression cassette comprising the amplifiable selection marker gene, these expression cassettes are also amplified. Therefore, the cell lines that grow through such rounds of amplification and selection are then screened on titre/yield and the best clone is selected for subsequent production of the AAV viral vector particle.

In a preferred embodiment, the host cell is negative for the amplifiable selection marker. That is to say, that the endogenous chromosome of the host cell does not comprise an endogenous amplifiable selection marker gene. For example, when using DHFR as the amplifiable selection marker, it is preferable to employ DHFR-negative host strains, such as CHO DG44 or CHO DUX-B11.

However, the invention is not limited by the choice of a particular host cell line. Any cell line which has a rapid rate of growth (i.e., a doubling time of 12 hours or less) and which is capable of amplifying the amplifiable selection marker gene at a reasonable rate without amplification of the endogenous amplifiable selection marker gene at a similar or higher rate may be used in the methods of the present invention.

Cell lines transduced with the dominant marker (i.e. exogenous amplifiable selection marker) are identified by determining that the ability of the cell to grow in increasing concentrations of the selection agent correlates with an increase in the copy number of the amplifiable selection marker (this may be measured directly by demonstrating an increase in the copy number of the amplifiable marker by Southern blotting or indirectly by demonstrating an increase in the amount of mRNA produced from the amplifiable marker by Northern blotting, or qPCR).

Where a host cell comprises an endogenous amplifiable selection marker gene, the nucleic acid vector may further comprise a nucleic acid sequence encoding a selectable marker in addition to the amplifiable selection marker. This circumvents the problem of amplification of the endogenous amplifiable selection marker gene during selection with the associated selection agent. The host cells are transfected with a nucleic acid vector comprising an amplifiable selection marker as well as a selectable marker. The transfected host cells are first selected for the ability to grow in the antibiotic of the selectable marker, such as zeocin or hygromycin p. The cells are then selected for the ability to grown in increasing concentrations of the selection agent, such as MTX.

In one embodiment, the nucleic acid vector additionally comprises a polyA signal. The use of a polyA signal has the advantage of protecting mRNA from enzymatic degradation and aiding in translation. In a further embodiment, the polyA signal is obtained from or derived from SV40, Bovine Growth Hormone and/or Human Beta Globin. In one embodiment, the polyA signal is derived from the SV40 early polyA signal (for example, see Genome Accession No. EF579804.1, base pairs 2668 to 2538 from the minus strand). In one embodiment, the polyA signal is derived from the Human Beta Globin polyA signal (for example, see Genome Accession No. GU324922.1, base pairs 3394 to 4162).

In one embodiment, the nucleic acid vector additionally comprises an intron sequence. The use of an intron downstream of the enhancer/promoter region and upstream of the cDNA insert (i.e. the transgene) is known to increase the level of expression of the insert. In a further embodiment, the intron sequence is a Human Beta Globin Intron or the Rabbit Beta Globin Intron II sequence. In one embodiment, the Human Beta Globin Intron is derived from the sequence available at Genome Accession No. KM504957.1 (for example from base pairs 476 to 1393). In one embodiment, the Rabbit Beta Globin Intron II is derived from the sequence available at Genome Accession No. V00882.1 (for example, from base pairs 718 to 1290).

In one embodiment, the nucleic acid vector comprises an intron inserted in the adenovirus rep/cap gene. In a preferred embodiment, the intron is a β-globin intron padded with a fragment of lambda phage DNA.

When an AAV ITR-flanked transgene (i.e. the recombinant DNA genome) is present in cells that are expressing AAV Rep and Cap, the Rep protein binds the ITRs flanking the transgene, initiating replication and producing single stranded copies of the ITR-flanked transgene. Rep then guides the packaging of this ssDNA into assembling AAV capsids in the cell nucleus.

In one embodiment, the nucleic acid vector comprises nucleic acid sequences encoding a single strand binding (SSB) protein. In one embodiment, the SSB protein is an *E. coli* SSB protein.

Although there is no overlapping sequence between the ITR-flanked gene therapy transgene and the AAV rep/cap gene, there is still the probability of generating wild-type replication competent AAV in which rep and cap have become inserted between the ITRs by non-homologous recombination (Allen et al., (1997) Journal of Virology 71: 6816-6822). Accordingly, production of rAAV vector particles may also result in the production of wild-type AAV vector particles that are impossible to separate from the gene therapy vector particle. Although AAV has not been associated with any diseases in humans and has low immunogenicity, this still poses a safety concern.

Several ways to try and prevent the recombination of rep/cap with the ITRs have been tested in the literature such as splitting rep and cap into separate plasmids or removing the distal 10 nucleotides in the D-sequences of the AAV ITRs and using Adenovirus helper genes lacking any ITRs. However, these methods generally result in a decrease in rAAV packaging efficiency and therefore a reduction in vector yield. Cao et al. (Cao et al., (2000) Journal of Virology 74: 11456-11463) tested a method of blocking the production of replication competent AAV by inserting a large padded intron into the rep gene in the rep/cap plasmid. This additional intron was spliced out during mRNA processing so that the Rep proteins could still be produced but it also increased the length of the AAV genes to a size that, if they were to recombine with the ITRs flanking the transgene, could no longer be effectively packaged into the AAV capsid. The intron they used was the 850 bp human β-globin intron which was inserted downstream of the P5 promoter in rep at a position 333 bp downstream from the Rep78/68 start codon. In experiments to test this rep/cap plasmid with additional intron, they saw no difference in GFP transgene-carrying rAAV yield compared to when rep/cap without the additional intron was used, as shown by average number of GFP positive cells per field when cells were transduced with the vector. In order to further expand the β-globin intron, they created plasmids in which the intron was padded by inserting various pieces of EcoRI+ HindIII digested lambda phage genome into the MfeI site of the intron. When rAAV produced using these plasmids with padded introns was used to transduce recipient cells, no replication competent AAV could be detected in the cells by PCR 36 hours post-transfection. Additionally, they found that the rep/cap plasmid containing a β-globin intron padded with a 1.5 kb fragment of lambda phage DNA, resulting in a 2.35 kb intron, increased yield of rAAV by 5-10 fold when compared to vector produced using the rep/cap plasmid without any additional intron. Western blotting of producer cell lysates probed with an anti-Rep antibody showed an increase in the ratio of Rep52 and Rep40 variants when this 2.35 kb intron plasmid was used. This alteration in the stoichiometry of Rep variants may have a positive impact on the packaging of the recombinant GFP transgene. Since this padded intron was shown to both significantly decrease the likelihood of producing replication competent AAV and increase recombinant vector yields.

In one embodiment, the nucleic acid vector additionally comprises a woodchuck hepatitis virus post-transcriptional regulatory element (WPRE). The presence of WPRE has been shown to enhance expression and as such is likely to be beneficial in attaining high levels of expression. In a further embodiment, the WPRE is derived from the sequence available at Genome Accession No. J04514.1 (for example, from base pairs 1093 to 1684).

In one embodiment, the nucleic acid vector additionally comprises an internal ribosome entry site (IRES). An IRES allows for translation initiation in an end-independent manner. An IRES is a structured RNA element that is usually found in the 5'-untranslated region (UTR) of viruses downstream of the 5'-cap (which is required for the assembly of the initiation complex). The IRES is recognized by translation initiation factors, and allows for cap-independent translation. In a further embodiment, the IRES is derived from the Encephalomyocarditis virus (EMCV) genome (for example, see Genome Accession No. KF836387.1, base pairs 151 to 724).

In one embodiment, the nucleic acid vector additionally comprises a Multiple Cloning Site (MCS). An MCS is a short segment of DNA within the nucleic acid vector which contains multiple restriction sites (for example, 10, 15 or 20 sites). These sites usually occur only once within the nucleic acid vector to ensure that the endonuclease only cuts at one site. This allows for the viral genes to be easily inserted using the appropriate endonucleases (i.e. restriction enzymes).

It will be understood by a person skilled in the art that the cassettes may be arranged in any order within the nucleic acid vector. In an exemplary embodiment, the nucleic acid vector comprises the following insert: a nucleic acid sequence encoding the helper virus genes (such as adenovirus), a nucleic acid sequence encoding the AAV rep/cap gene, a tetracycline resistance operon repressor protein (TetR), an internal ribosome entry site, and a selectable marker (such as a zeocin resistance selection marker) (i.e., Rep-Cap-Helper virus-TetRepressor-IRES-Antibiotic Resistance marker-remaining BAC sequence ("BAC bone", e.g. pSMARTBAC)). The nucleic acid vector may further comprise the DNA genome of the AAV vector particle, e.g. the transgene encoded between the two AAV ITRs, optionally including a promoter and/or a polyA signal. This may be inserted after the selectable marker (i.e., Rep-Cap-Helper virus-TetRepressor-IRES-Antibiotic Resistance marker-AAV genome-remaining BAC sequence ("BAC bone", e.g. pSMARTBAC))

In a further embodiment, an insulator (such as a chromatin insulator) is present between the nucleic acid sequences encoding: (i) the AAV rep/cap gene; (ii) the helper virus genes; and (iii) the DNA genome of the AAV vector particle (e.g. the transgene between two AAV ITRs). In a further embodiment, a promoter is present before the nucleic acid sequences encoding: (i) the AAV rep/cap gene; (ii) the helper virus genes; and (iii) the DNA genome of the AAV vector particle.

In one embodiment, the nucleic acid vector comprises the following insert: an adenovirus helper gene E2A operably linked to a promoter, an insulator (such as a chromatin insulator), an adenovirus helper gene E4 operably linked to a promoter, an insulator (such as a chromatin insulator), an adenovirus helper gene VA operably linked to a promoter, an insulator (such as a chromatin insulator), a nucleic acid sequence encoding the AAV rep/cap gene, an insulator (such as a chromatin insulator), a selectable marker (such as a zeocin resistance selection marker), an insulator (such as a chromatin insulator), a nucleic acid sequence comprising a transgene operably linker to a promoter between two AAV ITRs and a multiple cloning site.

Figure 2:
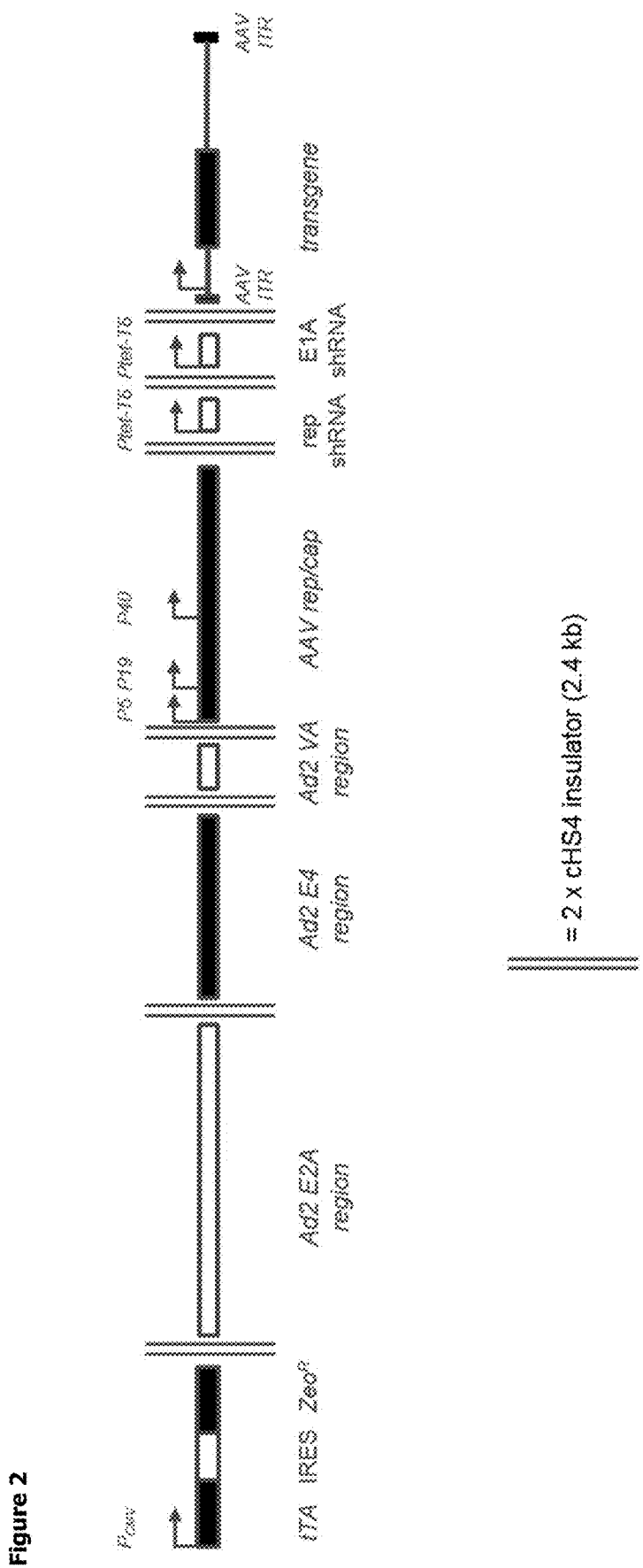
FIG. 2: A schematic diagram of an exemplary nucleic acid vector of the invention. The figure shows a linear bacterial artificial chromosome (BAC) construct containing the AAV viral genes (rep/cap), helper virus genes (E2A, E4 and VA from Adenovirus 2 [Ad2]), rep shRNA, E1A shRNA and ITR flanked transgene, all separated from each other by insulators (cHS4). The construct also contains an antibiotic resistance marker (ZeoR) and a translation initiation site (IRES).

In a further embodiment, represented as a schematic diagram in FIG. 2, the nucleic acid vector comprises the following insert: tTA gene operably linked to a selection marker comprising IRES, an insulator (such as a chromatin insulator), an adenovirus helper gene E2A operably linked to a promoter, an insulator (such as a chromatin insulator), an adenovirus helper gene E4 operably linked to a promoter, an insulator (such as a chromatin insulator), an adenovirus helper gene VA operably linked to a promoter, an insulator (such as a chromatin insulator), a nucleic acid sequence encoding the AAV rep and cap genes, an insulator (such as a chromatin insulator), a nucleic acid sequence encoding shRNA targeting an AAV rep mRNA molecule encoded by the AAV rep gene operably linked to a promoter, an insulator (such as a chromatin insulator), a nucleic acid sequence encoding shRNA targeting an adenovirus E1A mRNA molecule encoded by the adenovirus E1A gene operably linked to a promoter, an insulator (such as a chromatin insulator), a nucleic acid sequence comprising a transgene operably linker to a promoter between two AAV ITRs and a multiple cloning site.

The nucleic acid sequences may be introduced into the nucleic acid vector sequentially. This allows for selection after each integration to ensure that all of the required nucleic acid sequences are successfully integrated into the nucleic acid vector. Alternatively, at least two or more of the nucleic acid sequences are introduced into the nucleic acid vector simultaneously.

It will be understood that the additional genes described herein may be introduced into the nucleic acid vector by standard molecular cloning techniques known in the art, for example using restriction endonucleases and ligation techniques. Furthermore, the nucleic acid vector, in particular BACs, PACs, fosmids and/or cosmids, may be introduced into bacterial host cells (such as *E. coli* cells, in particular the *E. coli* strain DH10B) by standard techniques, such as electroporation.

Uses

According to a further aspect of the invention, there is provided the nucleic acid vector as defined herein for use in producing an AAV packaging or producer cell line.

The nucleic acid vectors described herein may be used to create an AAV packaging cell line which would greatly simplify AAV vector production. It will be understood that if a transgene is included on the nucleic acid vector, then this would be used to create a producer cell line.

As described herein, it would be useful to develop a stable AAV packaging (or producer) cell line in order to overcome the difficulties associated with transient transfection. The nucleic acid vectors described herein can be used to prepare said packaging cell lines because they are able to hold large DNA inserts containing the essential genes required for AAV packaging which can then be integrated into the endogenous genome of mammalian host cells in one step.

Host Cells

According to a further aspect of the invention, there is provided an AAV packaging cell for producing AAV vector particles comprising nucleic acid sequences encoding:
  AAV rep/cap gene; and
  helper virus genes;
  wherein said nucleic acid sequences are all integrated together at a single locus within the AAV packaging cell genome. It will be understood that these nucleic acid sequences are present as individual expression cassettes which prevents any risk of recombination to form replication competent virus.

The advantage of including all of the necessary viral genes for AAV vector production on a large nucleic acid vector is that they can be prepared in microbial cells (such as bacterial or yeast cells) first, which are much easier to handle and manipulate, before being integrated into mammalian cells in a single step. This relieves selection pressure and reduces the silencing timeframe once the viral genes have been integrated into a mammalian host cell. The characteristic feature of this method is that all of the genes required to create an AAV packaging cell line are present in a single locus in the endogenous genome, rather than randomly scattered throughout the endogenous genome. This has the advantage of producing an AAV packaging cell which expresses all of the viral genes at the same level because they are located at the same locus, as compared to previous methods where the viral genes are integrated randomly throughout the endogenous genome which may cause uneven levels of expression.

It will be understood that the nucleic acid vector construct may integrate more than once in the host cell genome at multiple different locations on different chromosomes (albeit with all of the encoded nucleic acid sequences present in a single locus). Therefore, reference to a "single locus" does not exclude the possibility that the nucleic acid sequences are all located together at multiple loci within the AAV packaging cell genome. This may be beneficial for increasing expression levels of the transgenes and could potentially improve AAV titres. It is possible to compare the copy number of construct insertions between cell populations derived from individual clones by qPCR.

In one embodiment, the AAV packaging cell additionally comprises nucleic acid sequences which encode the DNA genome of the AAV vector particle. This may also be located at the single locus with the nucleic acid sequences encoding the AAV rep/cap gene and the helper virus genes. When the DNA of the AAV vector particle is present in the host cell, it will be understood that this cell may be referred to as an AAV producer cell.

Therefore, according to a further aspect of the invention, there is provided an AAV producer cell for producing AAV vector particles comprising nucleic acid sequences encoding:
  AAV rep/cap gene;
  helper virus genes; and
  the DNA genome of the AAV vector particle,
  wherein said nucleic acid sequences are all integrated together at a single locus within the AAV producer cell genome (i.e. as individual expression cassettes).

In one embodiment, the AAV packaging cell is a mammalian cell. In a further embodiment, the mammalian cell is selected from a HEK 293 cell, CHO cell, Jurkat cell, KS62 cell, PerC6 cell, HeLa cell or a derivative or functional equivalent thereof. In a yet further embodiment, the mammalian host cell is a HEK 293 cell, or derived from a HEK 293 cell. Such cells could be adherent cell lines (i.e. they grow in a single layer attached to a surface) or suspension adapted/non-adherent cell lines (i.e. they grow in suspension in a culture medium). In a yet further embodiment, the HEK 293 cell is a HEK 293T cell. The term "HEK 293 cell" refers to the Human Embryonic Kidney 293 cell line which is commonly used in biotechnology. In particular, HEK 293 cells are commonly used for the production of AAV vectors because they already contain the E1A and E1B helper virus genes, so only the E2A, E4ORF6 and VA helper factors need to be provided. Other examples of suitable commercially available cell lines include T-REX™ (Life Technologies) cell lines.

In one embodiment the host cell overexpresses single strand binding (SSB) proteins as compared with a wild-type strain of the same species of the host cell. In one embodiment, the host cell comprises an exogenous nucleic acid sequence encoding a single strand binding (SSB) protein.

It will be understood that all of the embodiments described hereinbefore for the nucleic acid vector, may also be applied to the AAV packaging/producer cells of the invention.

Methods

According to a further aspect of the invention, there is provided a method of producing a stable AAV packaging cell line, comprising:

(a) introducing the nucleic acid vector as described herein into a culture of mammalian host cells; and (b) selecting within the culture for a mammalian host cell which has the nucleic acid sequences encoded on the vector integrated into an endogenous chromosome of the mammalian host cell.

It will be understood that the methods defined herein are suitable for the production of all serotypes and chimeras of AAV, e.g., AAV1, AAV2, AAV3, AAV4, AAV5, AAV6, AAV7, AAV8, AAV9, AAV10, AAV11, AAV12, AAV13, and any chimeras thereof.

In one embodiment, the mammalian cell is selected from a HEK 293 cell, HEK 6E cell, CHO cell, Jurkat cell, KS62 cell, PerC6 cell, HeLa cell or a derivative or functional equivalent thereof. In a further embodiment, the mammalian host cell is a HEK 293 cell, or derived from a HEK 293 cell. Such cells could be adherent cell lines (i.e. they grow in a single layer attached to a surface) or suspension adapted/non-adherent cell lines (i.e. they grow in suspension in a culture medium). In a yet further embodiment, the HEK 293 cell is a HEK 293T cell or HEK 6E cell. Other examples of suitable commercially available cell lines include T-REX™ (Life Technologies) cell lines.

The skilled person will be aware that introducing the nucleic acid vector into the host cell may be performed using suitable methods known in the art, for example, lipid-mediated transfection, microinjection, cell (such as microcell) fusion, electroporation or microprojectile bombardment. In one embodiment, the nucleic acid vector is introduced into the host cell by electroporation. It will be understood that the choice of method to use for introducing the nucleic acid vector can be chosen depending upon the type of mammalian host cell used.

Once inside the mammalian host cell, the nucleic acid vector will randomly integrate into the endogenous genome of the mammalian host cell. Therefore, the method additionally comprises selecting for the mammalian host cell in which the nucleic acids encoded on the nucleic acid vector have integrated (for example, using an antibiotic resistance selection marker, such as a zeocin resistance marker).

The skilled person will be aware of methods to encourage integration of the nucleic acid vector, for example, linearising the nucleic acid vector if it is naturally circular (for example, BACs, PACs, cosmids or fosmids). The nucleic acid vector may additionally comprise areas of shared homology with the endogenous chromosomes of the mammalian host cell to guide integration to a selected site within the endogenous genome. Furthermore, if recombination sites are present on the nucleic acid vector then these can be used for targeted recombination. For example, the nucleic acid vector may contain a loxP site which allows for targeted integration when combined with Cre recombinase (i.e. using the Cre/lox system derived from P1 bacteriophage). Alternatively (or additionally), the recombination site is an att site (e.g. from lambda phage), wherein the att site permits site-directed integration in the presence of a lambda integrase. This would allow the viral genes to be targeted to a locus within the endogenous genome which allows for high and/or stable expression.

Other methods of targeted integration are well known in the art. For example, methods of inducing targeted cleavage of genomic DNA can be used to encourage targeted recombination at a selected chromosomal locus. These methods often involve the use of engineered cleavage systems to induce a double strand break (DSB) or a nick in the endogenous genome to induce repair of the break by natural processes such as non-homologous end joining (NHEJ) or repair using a repair template (i.e., homology directed repair or HDR).

Cleavage can occur through the use of specific nucleases such as engineered zinc finger nucleases (ZFN), transcription-activator like effector nucleases (TALENs), using the CRISPR/Cas9 system with an engineered crRNA/tracr RNA ('single guide RNA') to guide specific cleavage, and/or using nucleases based on the Argonaute system (e.g., from *T. thermophilus*, known as 'TtAgo', see Swarts et al. (2014) *Nature* 507(7491): 258-261). Targeted cleavage using one of these nuclease systems can be exploited to insert a nucleic acid into a specific target location using either HDR or NHEJ-mediated processes. Therefore, in one embodiment, the method additionally comprises integrating the nucleic acid sequences encoded on the nucleic acid vector into the genome (i.e. an endogenous chromosome) of the mammalian host cell using at least one nuclease, wherein the at least one nuclease cleaves the genome of the mammalian host cell such that the nucleic acid sequences are integrated into the genome of the cell. In a further embodiment, the nuclease is selected from the group consisting of a zinc finger nuclease (ZFN), a TALE nuclease (TALEN), a CRISPR/Cas nuclease system and combinations thereof.

According to a further aspect of the invention, there is provided an AAV packaging or producer cell obtained by the method defined herein.

The cell line obtained using the methods defined herein may be used to produce a high titre of AAV vector. Viral titre may be measured by quantitative PCR (qPCR), which provides the genome copy number of AAV particles, and by ELISA which provides the TCID50 measure of infectious virus titre. By comparing the two measurements, the efficiency of transduction with the AAV batch can be determined.

References herein to the term "high titre" refer to an effective amount of AAV vector particles which is capable of transducing a target cell, such as a patient cell. In one embodiment, a high titre is in excess of $10^6$ TU/ml without concentration (TU=transducing units).

In one embodiment, the methods defined herein scalable, so they can be carried out in any desired volume of culture medium, e.g., from 10 ml (e.g., in shaker flasks) to 10 L, 50 L, 100 L, or more (e.g. in bioreactors such as wave bioreactor systems and stirred tanks).

According to a further aspect of the invention, there is provided a method of producing a replication defective AAV vector particle, comprising:

(a) introducing the nucleic acid vector as defined herein into a culture of mammalian host cells;

(b) selecting within the culture for a mammalian host cell which has the nucleic acid sequences encoded on the vector integrated into an endogenous chromosome of the mammalian host cell; and (c) further culturing the selected mammalian host cell under conditions in which the replication defective AAV vector particle is produced.

As described hereinbefore, in one embodiment, the mammalian host cell is selected from a HEK 293 cell, CHO cell, Jurkat cell, KS62 cell, PerC6 cell, HeLa cell or a derivative or functional equivalent thereof. In a further embodiment, the mammalian host cell is a HEK 293 cell, or derived from a HEK 293 cell. Such cells could be adherent cell lines (i.e. they grow in a single layer attached to a surface) or suspension adapted/non-adherent cell lines (i.e. they grow in suspension in a culture medium). In a yet further embodiment, the HEK 293 cell is a HEK 293T cell. Other examples of suitable commercially available cell lines include T REX™ (Life Technologies) cell lines.

It will be understood by the skilled person that the conditions used in the method described herein will be dependent upon the host cell used. Typical conditions, for example the culture medium or temperature to be used, are well known in the art. In one embodiment, culturing is performed by incubating the mammalian host cell under humidified conditions. In a further embodiment, the humidified conditions comprise incubating the transfected cells at 37° C. at 5% $CO_2$. In one embodiment, culturing is performed using a culture medium selected from: Dulbecco's modified Eagle's medium (DMEM) containing 10% (vol/vol) fetal bovine serum (FBS), serum-free UltraCULTURE™ medium (Lonza, Cat. No. 12-725F), or FreeStyle™ Expression medium (Thermo Fisher, Cat. No. 12338-018).

Appropriate culturing methods are well known to a person skilled in the art. For example, the cell may be cultured in suspension and/or in animal component-free conditions. In one embodiment, the cell is suitable for culturing in any volume of culture medium, from 10 ml (e.g. in shaker flasks) to 10 L, 50 L, 100 L, or more (e.g. in bioreactors).

As described herein, use of the claimed invention reduces the cost of plasmid manufacture, reduces requirement for transfection reagents (e.g. Polyethylenimine [PEI]), reduces the amount of Benzonase® endonuclease treatment required (there is a reduced amount of DNA in the viral harvest, therefore less Benzonase® endonuclease is needed to remove the excess in downstream processing) and reduces costs of testing (there is no need to test for residual plasmid in the viral product). All of these advantages may be considered as aspects of the invention.

In one embodiment, the method additionally comprises isolating the replication defective AAV vector particle. For example, in one embodiment the isolating is performed by using a filter. In a further embodiment, the filter is a low-protein binding membrane (e.g. a 0.22 μm low-protein binding membrane or a 0.45 μm low-protein binding membrane), such as polyvinylidene fluoride (PVDF) or polyethersulfone (PES) artificial membranes.

Once inside the mammalian host cell, the nucleic acid sequences present on the nucleic acid vector may integrate into a random, single locus (or multiple times and therefore at more than one loci) within the endogenous genome. The integration step may be encouraged as described hereinbefore, for example using linearisation and/or areas of shared homology. Recombination sites may also be used for targeted recombination.

If the target genes are integrated into the endogenous chromosomes with a selective marker, such as an antibiotic resistance gene, then the method may additionally comprise selecting for the mammalian host cells in which the viral nucleic acids have successfully integrated.

Once isolated, the AAV vector particles may be concentrated for in vivo applications. Concentration methods include, for example, ultracentrifugation, precipitation or anion exchange chromatography. Ultracentrifugation is useful as a rapid method for AAV vector concentration at a small scale. Alternatively, anion exchange chromatography (for example using Mustang Q anion exchange membrane cartridges) or precipitation (for example using PEG 6000) are particularly useful for processing large volumes of AAV vector supernatants.

According to a further aspect of the invention, there is provided a replication defective AAV vector particle obtained by the method defined herein.

The invention will now be described in further detail with reference to the following, non-limiting Examples.

EXAMPLES

Example 1: Design of AAV Bacterial Artificial Chromosome

Nucleic acid vectors of the invention may be designed using methods known in the art. A detailed, exemplary method is provided herein:

Gibson cloning primers are designed to amplify the tetracycline-controlled transactivator (tTA) gene in a construct including a $P^{CMV}$ promoter, an IRES, and a Zeocin resistance gene in the order $P^{CMV}$-intron-tTA-ZeoR-polyA. The primers allow cloning into the pSMART BAC backbone (Lucigen Corp.) by Gibson assembly. A restriction site for PI-PspI for sequential iBrick cloning (Liu et al. (2014) *PLoS One* 9(10):e110852, incorporated herein by reference) is included between the polyA and the plasmid.

Two chicken HS4 (cHS4) insulators in tandem are cloned 3' of the ZeoR polyA into the PI-PspI site as follows. The 2×cHS4 fragment from pMA-BACmod-GSKCOTR-IR-Zeo is amplified using I-SceI forward and PI-PspI reverse primers. Between the I-SceI site and the 2×cHS4 insulators are restriction sites for MluI and NheI. This fragment is subcloned into pCR-Blunt II TOPO (Thermo Fisher). This is used as a BAC donor vector.

The 2×cHS4 fragment in pCR-Blunt II TOPO is digested with I-SceI and PI-PspI. The pSMART BAC is digested with PI-PspI and dephosphorylated. The I-SceI and PI-PspI digested 2×cHS4 is then cloned into the PI-PspI site. This will abrogate the 5' PI-PspI site and leave an intact PI-PspI site downstream of 2×cHS4.

All other cassettes to be inserted into pSMART BAC by iBrick cloning are cloned into the MluI and NheI sites upstream of 2×cHS4 in the BAC donor vector. These can then be digested out with I-SceI and PI-PspI and include the 2×cHS4 at the 3' end every time. Using MluI forward and XbaI reverse primers or including these sites in gene synthesis will abrogate the NheI upstream of 2×cHS4 in all but the very first cHS4 that is inserted downstream of ZeoR. Gene cassettes that are exceptions to this method are E2A, which contains MluI sites and is therefore inserted into the BAC using iBrick cloning separate to 2×cHS4; and VA, which contains NheI and XbaI sites and therefore the reverse primer should include an AvrII mismatch site (compatible ends with NheI in the donor plasmid).

The AAV rep/cap gene is cloned upstream of 2×cHS4 insulators in the BAC donor vector. This is then iBrick cloned into the BAC.

Next, each of the Adenovirus helper genes are cloned into the BAC donor vector upstream of the 2×cHS4 insulators. These are iBrick cloned into the BAC too.

The full BAC construct is stably transfected into host cells to make a stable cell line. Cell lines are then tested for AAV titres.

Example 2: Design and Synthesis of AAV BAC with Additional Components

A BAC was created containing every genetic element (i.e. expression cassettes) required for rAAV particle production cloned into it: the AAV rep/cap gene; the helper virus genes and a recombinant DNA genome of an AAV vector particle. Furthermore, additional components were also included as outlined below.

In order to control the level of AAV Rep expressed in the transfected mammalian cell, it was decided to include shRNA targeting Rep and E1A in the construct under the control of a conditional promoter (Ptet-T6).

The BAC also includes the tetracyclin-sensitive transcriptional activator, tTA. Under normal growth conditions, suspension adapted HEK293 cells in which the construct is stably integrated into the genome would express the shRNA and Rep and E1A expression would be knocked down. When the cells reached a density suitable for rAAV particle production, doxycycline (DOX) could be added to the growth medium. This would destabilise the tTA transactivator and switch off the transcription of the shRNA, allowing Rep and E1A to be produced and rAAV particle production to proceed.

A padded intron was also inserted into the rep gene in order to reduce the likelihood of replication competent AAV (rcAAV) forming and have the extra benefit of increasing yields of rAAV particles in producer cells (Cao et al., (2000) Journal of Virology 74: 11456-11463).

2.1: Design and Synthesis of Padded Human β-Globin Intron Sequence

Cao et al. (Cao et al., (2000) Journal of Virology 74: 11456-11463) had created a padded intron by amplifying the human β-globin intron B by PCR and cloned the fragment into a plasmid. Lambda phage DNA was digested with EcoRI+HindIII and a 1.5 kb fragment was cloned into the MfeI site of the β-globin gene.

To recreate this work in silico, the *Homo sapiens* β-globin gene (accession number AH001475) and the Enterobacteria phage lambda complete genome sequence (accession number J02459) were imported into SnapGene software (GSL Biotech LLC) from GenBank. The β-globin intron B was annotated in the GenBank sequence as the 850 bp between nucleotides 2057-2906. A simulated agarose gel of the lambda phage genome sequence digested with EcoRI+HindIII revealed 1.375 and 1.709 kb fragment instead of the expected 1.5 kb fragment. The 1.375 kb EcoRI/HindIII fragment contained an EcoRI site at the 5' end and a HindIII site at the 3' end. This sequence was copied and pasted into the MfeI site at nucleotide position 174 of the β-globin intron B sequence. The resulting padded intron sequence was 2225 bp long. In order to amplify this fragment with primers that contain sequence homology to the region of the rep2 gene in which it is to be inserted, sequences were added to the 5' (TGGACGTTTCCTGAGTCAG; SEQ ID NO: 1) and 3' (ATTCGCGAAAAACTGATTCAG; SEQ ID NO:2) end of the sequence, homologous to the sequence flanking the insertion site in rep2. The sequence was then synthesised and ligated into pG.AAV2.R2C2 and pG.AAV2.R2C5 to form pG.AAV2.R2C2-intron and pG.AAV2.R2C5-intron, respectively.

2.2: Design and Synthesis of shRNAs Targeting AAV Rep mRNA Molecules shRNAs targeting AAV2 rep gene transcripts downstream of the P19 promoter were designed. By targeting only sequences downstream of P19 excluding sequences present in the rep intron means all 4 rep mRNA variants are targeted for knock down.

21-nucleotide shRNA sequences were designed with homology to regions of rep and cap genes from AAV2 and cap from AAV5 that conformed to the criteria for effective shRNA as outlined in Dow et al. (Dow et al., (2012) Nature Protocols 7: 347-393). These criteria are as follows:

A or T at position 1
40-80% A/T content
>50% A/T content in positions 1-14
(A/T % positions 1-14)/(A/T % positions 15-21)=>1
No A at position 20
An A or T at position 13 OR a T at position 14
No 'AAAAAA', 'TTTTT', 'CCCC' or 'GGGG'

These criteria were applied to the reverse complement strand of AAV 2 rep gene. A region of homology between AAV 2 cap gene and AAV 5 cap gene (nucleotides 3086-3106 of AAV2 GenBank sequence AF043303) was found to match these criteria. An shRNA targeting this sequence could potentially be used to knock down both Rep and Cap expression in AAV2 and AAV5. In addition to manually searching through the sequence looking for sequences that match the criteria, the sequence of AAV 2 rep gene downstream of the P19 promoter was copy pasted into the custom sequence box of the micro-RNA adapted shRNA design tool as referenced in Adams et al. (Adams et al. (2017), Biomaterials 139:102), an online tool that finds and ranks shRNA target sequences that conform to the criteria for effective shRNA.

The tool applied these criteria to 21 nucleotide long sequences in the reverse strand and provided the sequence of the target in the sense strand. With the miRNA score set to >10, the website found many possible shRNA targets. The website ranked several targets as having the highest miRNA score, denoting their likelihood to be expressed well from a RNA Polymerase II promoter. These included two target sequences in the AAV2 rep intron and these sequences would, therefore, not be effective against rep68 or rep40 transcripts. However, the 3 highest ranked targets out-with the intron were used, rep2 shRNA 11 (16.4), shRNA 13 (14.4) and shRNA 14 (13.7). The reverse complement of these sequences was derived. These targeting strands (also known as guide strands) would form the 3' end of the short hairpin loop in the micro-RNA adapted shRNAs. The reverse complement sequences are shown in the table below:

| shRNA Name | Targeting Strand |
|---|---|
| AAV cap2/5 shRNA | TGTTGATGAGTCTTTGCCAGT (SEQ ID NO: 3) |
| AAV rep2 shRNA 5 | TCTTTCCCGCATTGTCCAAGG (SEQ ID NO: 4) |
| AAV rep2 shRNA 7 | TTTATAAATCCGATTGCTGGA (SEQ ID NO: 5) |
| AAV rep2 shRNA 9 | AAGGTCGTTGAGTTCCCGTCA (SEQ ID NO: 6) |
| AAV rep2 shRNA 11 | TTTGACGTAGAATTCATGCTC (SEQ ID NO: 7) |
| AAV rep2 shRNA 13 | TCAAATTTGAACATCCGGTCT (SEQ ID NO: 8) |
| AAV rep2 shRNA 14 | TTGAAGGGAAAGTTCTCATTG (SEQ ID NO: 9) |

As outlined in FIG. 2 of Dow et al. (Dow et al., (2012) Nature Protocols 7: 347-393) a C nucleotide was added to the 5' end of those sense strand sequences that started with an A or T and an A nucleotide was added to the 5' end of those sense strand sequences that started with a G or C.

The miR-30a loop sequence was then added to the 3' end of each sense strand sequence (5'-TAGTGAAGCCACAGATGTA-3' (SEQ ID NO: 10)).

To form the hairpin, the targeting strand sequence was added 3' of the loop. At the 3' end of this sequence, also known as the guide strand, an A or C nucleotide was added if a C or A was added 5' of the sense strand respectively.

Figure 3:
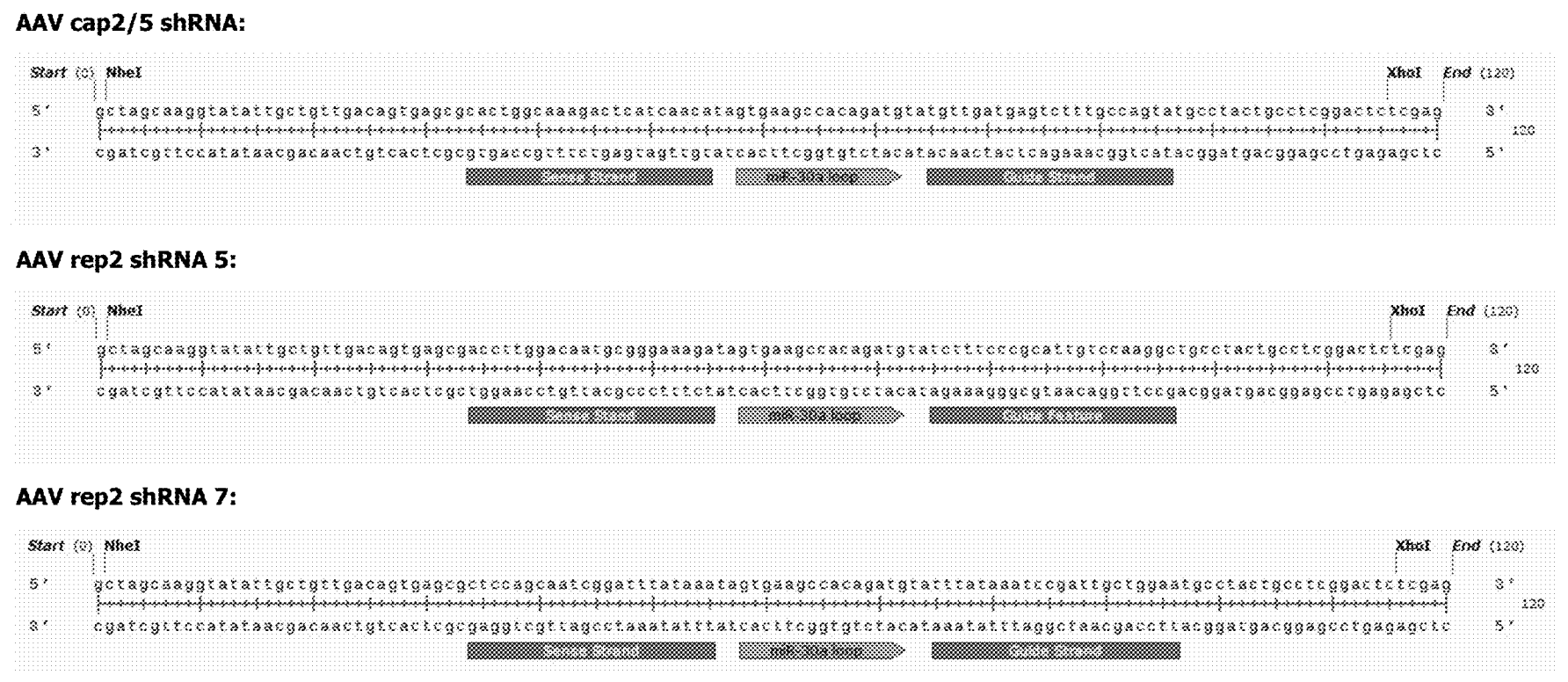

In order to express the shRNA sequences from a plasmid with an RNA polymerase II promoter (Paw), the shRNA sequences were micro-RNA adapted. This meant adding the micro-RNA sequences 5'-AAGGTATATTGCTGTTGACA-GTGAGCG-3' (SEQ ID NO: 11) upstream of the sense strand and 5'-TGCCTACTGCCTCGGACT-3' (SEQ ID NO: 12) downstream of the guide strand. In order to clone the micro-RNA adapted shRNAs into the multiple cloning site of the plasmid pG3, restriction sites for NheI and XhoI were added to the 5' and 3' ends, respectively. The sequences of micro-RNA adapted shRNAs are shown in FIG. 3.

2.3: Design and Synthesis of shRNAs Targeting E1A mRNA Molecules

The sense strand of the Ad5 E1A gene (nucleotides 560-1545 of GenBank accession number AC_000008) was copy pasted into the custom sequence box of the micro-RNA adapted shRNA design tool referenced in Adams et al., as in 2.2.

With the miRNA score set to >10, the website found 5 possible shRNA targets with scores ranging from 10.1 to 10.9. The reverse complement of these sequences were derived. These targeting strands formed the 3' end of the short hairpin loop in the micro-RNA adapted shRNAs. The reverse complement sequences are shown in the table below:

| shRNA Name | Targeting Strand |
|---|---|
| E1A shRNA 1 | TGGCAGGTAAGATCGATCACC (SEQ ID NO: 13) |
| E1A shRNA 2 | TTACTGTAGACAAACATGCCA (SEQ ID NO: 14) |
| E1A shRNA 3 | TCTAAATCATACAGTTCGTGA (SEQ ID NO: 15) |
| E1A shRNA 4 | TCCGTACTACTATTGCATTCT (SEQ ID NO: 16) |
| E1A shRNA 5 | TCTAACACAAACTCCTCACCC (SEQ ID NO: 17) |

As was done in 2.2, a C nucleotide, or an A nucleotide was added to the 5' end of the sense strand sequences as appropriate and then the miR-30a loop sequence was then added to the 3' end of each sense strand sequence. To form the hairpin, the targeting strand sequence added to the 3' of the loop and an A or C nucleotide added as appropriate as was done in 2.2.

In order to express the shRNA sequences from a plasmid with an RNA polymerase II promoter (Ptet-T6), the sequences were micro-RNA adapted as was done in 2.2. In order to clone the micro-RNA adapted shRNAs between a Ptet-T6 promoter and polyA sequence, restriction sites for XbaI and XhoI were added to the 5' and 3' ends, respectively.

2.4: Design and Synthesis of the Tet-Operon Containing, RNA Pol II Promoter, Ptet-T6

The sequence of the Ptet-T6 promoter with 7 tet-operon tandem sequences was taken from Loew et al. (Loew et al., (2010) BMC Biotechnology 10: 81). At the 5' end, a 20 bp sequence homologous to the 3' end of the poly-A from pMA-BACmod.GSKCOTR-IR-ZeoR was added and downstream of Ptet-T6 was added a 20 bp sequence homologous to the 5' end of the EGFP gene in pG3_cPPT.PGK-EGFP.WPRE. The full sequence was synthesised.

2.5: Design and Synthesis of AAV Donor Plasmids

Donor plasmids were constructed that would act as intermediates before expression cassettes are cloned into a BAC by iBrick cloning (as outlined in Liu et al. (2014) PLoS One 9: e110852). The donor plasmid, pDonor, contains MluI and NheI restriction sites for directional cloning of expression cassettes upstream of two tandem copies of the cHS4 element from the chicken β-like globin gene cluster (2×cHS4). The 2×cHS4 act as insulators that alleviate promoter interference between expression cassettes cloned in proximity in large constructs, such as the nucleic acid vector of the invention, and also helps to maintain an open chromatin state. pDonor also contains an I-SceI site upstream of the MluI site and a PI-PspI site downstream of the 2×cHS4. These meganuclease sites allow any fragment cloned into pDonor to be digested out with these 2 enzymes and directionally cloned into a single PI-PspI site in a large genetic construct such as the BAC, along with 2×cHS4 at the 3' end. This means that every expression cassette cloned into pDonor, then transferred to the BAC will be padded at the 3' end by 2×cHS4.

Figure 4:
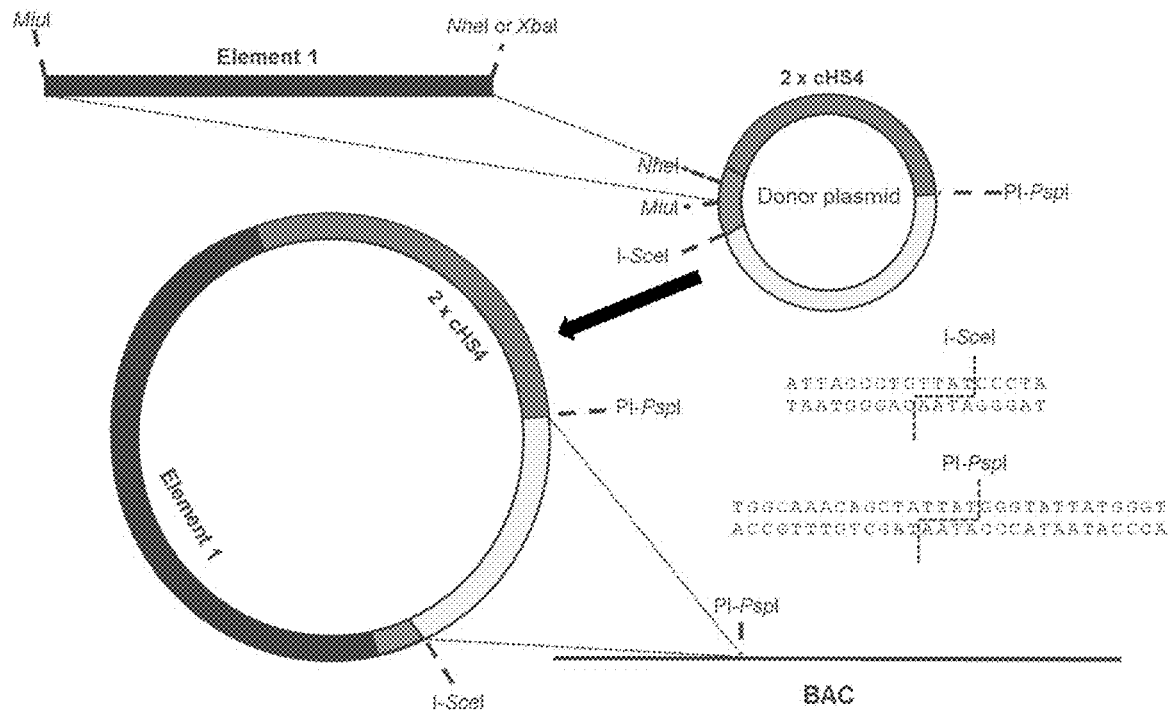
FIG. 4: A schematic diagram showing a method of cloning each expression cassette into the donor plasmid containing 2×cHS4 and then cloning both the expression cassette and 2×cHS4 into a BAC.
Figure 4:
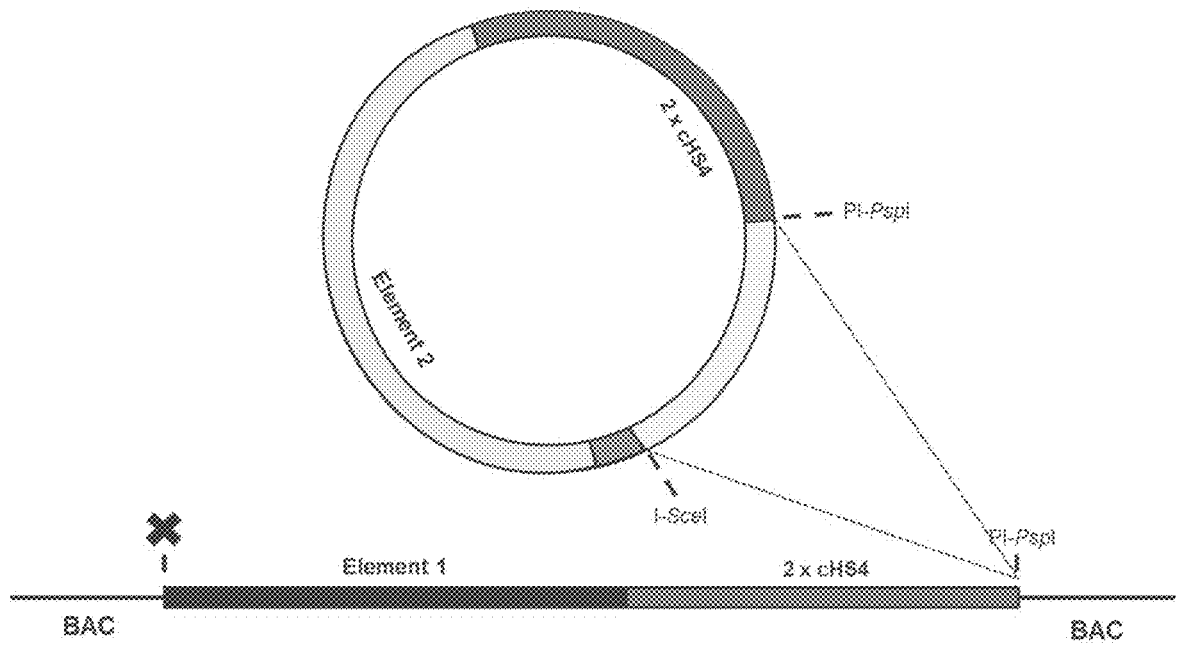

The method of cloning each expression cassette into the donor plasmid containing 2×cHS4 and then cloning both the expression cassette and 2×cHS4 into a BAC is shown schematically in FIG. 4. In the figure, "element" denotes an expression cassette.

2.5.1: Preparation of 2×cHS4 Donor Plasmid

To prepare the donor plasmid a PCR was set up to amplify the 2×cHS4 from pMA.BACmod.GSKCOTR-IR-ZeoR with an I-SceI site at the 5' end and a PI-PspI at the 3' end. The PCR (total volume of 25 μl contained the following components):

| Component | Volume | Final Concentration |
|---|---|---|
| 5x NEB Q5 Polymerase Reaction Buffer | 5 μl | 1x |
| 10 mM dNTPs | 0.5 μl | 200 μM |
| 10 μM Forward Primer | 1.25 μl | 0.5 μM |
| 10 μM Reverse Primer | 1.25 μl | 0.5 μM |
| Template DNA (0.5 ng/μl) | 1 μl | 0.5 ng |
| NEB Q5 DNA Polymerase | 0.25 μl | 0.02 U/μl |
| Nuclease-Free Water | 15.75 μl | — |

Primer Sequences

| Name | Sequence |
|---|---|
| 2xcHS4 donor I-SceI F | ATTACCCTGTTATCCCTATTATACGAAGTTATATTACGCG (SEQ ID NO: 18) |
| 2xcHS4 donor PI-PspI R | ACCCATAATACCCATAATAGCTGTTTGCCATAACTAGTCAA TAATCAATGTC (SEQ ID NO: 19) |

The primers were obtained from ThermoFisher Scientific. Underlined nucleotides denote a 5' overhang included in the primer to insert a restriction site for either I-SceI or PI-PspI.

The PCR thermal cycling was performed using a Bio-Rad C1000 Touch thermal cycler. The conditions for the reactions were as follows using pMA.BACmod.GSKCOTR-IR-ZeoR as template:

| | | |
|---|---|---|
| 98° C. | 30 sec | 1 cycle |
| 98° C. | 15 sec | ⎫ |
| 56° C. | 15 sec | ⎬ 4 x |
| 72° C. | 2:00 min | ⎭ |
| 98° C. | 15 sec | ⎫ |
| 59° C. | 15 sec | ⎬ 31 x |
| 72° C. | 2:00 min | ⎭ |
| 72° C. | 5:00 min | |
| 4° C. | Hold | |

Following thermal cycling, the PCR reaction was subjected to gel electrophoresis on a 1% agarose gel containing 1×TAE and 1×SYBR Safe at 80 V for 1 hour. The PCR product was excised from the gel and the DNA purified using Qiaquick Gel Extraction kit (Qiagen, Cat No. 28706).

A ligation was set up containing 0.5 µl pCR-Blunt II-TOPO (Thermo Fisher, Cat. No. 1(280002), 1 µl of salt solution and 4.5 µl of gel purified PCR product. The ligation was incubated at room temperature for 5 minutes and then 2 µl of the ligation was used to transform a vial of OneShot TOP10 chemically competent *E. coli* (Thermo Fisher, Cat. No. C404003). The transformed cells were spread on an LB agar plate containing 50 µg/ml Kanamycin and incubated at 37° C. overnight.

Colonies were picked from the transformation plate and subcultured on LB agar plates containing 50 µg/ml Kanamycin. The subcultured colonies were grown in 3 ml LB broth cultures containing 50 µg/ml Kanamycin at 37° C. overnight with gentle agitation. The following day the plasmid DNA was extracted from the broth cultures using a QiaPrep Spin Miniprep kit (Qiagen, Cat. No. 27106). The concentration of DNA in each of the minipreps was calculated using a Nanodrop and 1 ug of each of the plasmid preps was digested with EcoRI to release the cloned 2×cHS4. The digests were incubated at 37° C. for 2 hours and then subjected to gel electrophoresis on a 0.8% agarose gel containing 1×TAE and 1×SYBR Safe at 80 V for 1 hour. The minipreps were Sanger sequenced using the M13 forward and reverse primers. The sequencing alignments showed that the 2×cHS4 PCR fragment with a 5' I-SceI and 3' PI-PspI site had been cloned into pCR-Blunt II-TOPO.

2.5.2: Cloning of Expression Cassettes into the 2×cHS4 Donor Plasmid
Primer Sequences

| Name | Sequence |
|---|---|
| E4 MluI F | GTCGCACGCGTTTTAGGGCGGAGTAAC<br>(SEQ ID NO: 20) |
| E4 XbaI R | AACATTCTAGAACTAGTGAATCCAC<br>(SEQ ID NO: 21) |
| VA MluI F | ATGAGACGCGTGATATCCGTAGATGTACC<br>(SEQ ID NO: 22) |
| VA AvrII R | GATTCCCTAGGCCGCGGATGTTGCCCCTC<br>(SEQ ID NO: 23) |
| rep2 MluI F | CCTCGCGAATGCAACGCGTGGAGGGGTGGAGTCGTG<br>(SEQ ID NO: 24) |
| cap XbaI R | GATTATCTAGACATGCTACTTATCTACGTAGCC<br>(SEQ ID NO: 25) |

2.5.2.1: PCR of Adenovirus 2 E4 and VA
PCRs was set up to amplify the Adenovirus 2 E4 and VA regions from pG3.Ad2 Helper GSK with an MluI site at the 5' end and an enzyme with compatible end with NheI at the 3' end. The reverse primer used to amplify E4 contained an XbaI site while VA contains internal restriction sites for NheI and XbaI so the VA reverse primer contained an AvrII site, which is also compatible with NheI. The PCR reaction contained the same components as that in 2.5.1 above.

The PCR thermal cycling was performed using a Bio-Rad C1000 Touch thermal cycler. The conditions for the reactions were as follows using pMA.BACmod.GSKCOTR-IR-ZeoR as template:

| | | |
|---|---|---|
| 98° C. | 30 sec | 1 cycle |
| 98° C. | 15 sec | ⎤ |
| 59° C. | 15 sec | ⎥ 35 x |
| 72° C. | 3:45 min | ⎦ |
| 72° C. | 5:00 min | 1 cycle |
| 4° C. | Hold | |

The PCR reactions were subjected to gel electrophoresis as in 2.5.1. The gel confirmed that the correct 3.21 kb E4 and 0.76 kb VA fragments had been amplified. The PCR products were DNA purified using a Qiaquick Gel Extraction kit.

2.5.2.2: PCR of AAV Rep2/Cap2 and Rep2/Caps with Padded Introns in Rep2

PCRs was set up to amplify the AAV rep/cap from pG.AAV2.R2C2-intron and pG2.AAV5.R2C5-intron with an MluI site at the 5' end and a XbaI site at the 3' end. The PCRs utilised Q5 DNA polymerase 2× Master mix in a total volume of 25 µl. The thermal cycling conditions were the same as those used in 2.5.2.1.

Following thermal cycling, the PCR reactions were subjected to gel electrophoresis as before. The gel confirmed that the correct 6.62 kb R2C2-intron and 6.59 kb R2C5-intron fragments had been amplified. The PCR products were DNA purified.

2.5.2.3: Cloning of PCR Fragments into PCR-Blunt II-TOPO

Ligations were set up containing 0.5 µl pCR-Blunt II-TOPO, 1 µl of salt solution and 4.5 µl of each gel purified PCR product (E4, VA, R2C2-intron, and R2C5-intron). The ligations were incubated at room temperature for 5 minutes and then 2 µl of each ligation was used to transform vials of OneShot TOP10 chemically competent *E. coli*. The transformed cells were spread on an LB agar plate containing 50 µg/ml Kanamycin and incubated at 37° C. overnight.

Colonies were subcultured on LB agar plates and then grown overnight as was done in 2.5.1. The plasmid DNA was extracted from the broth cultures, concentration of DNA calculated as was done in 2.5.1. 1 ug of each of the E4, R2C2-intron and R2C5-intron in pCR-Blunt plasmid preps was digested with MluI+XbaI whereas the VA in pCR-Blunt plasmid preps were digested with MluI+AvrII. The digests were incubated at 37° C. for 2 hours and then subjected to gel electrophoresis.

The pCR-Blunt backbone is approximately 3.47 kb in length. The gels confirmed that the correct 3.2 kb E4, 0.74 kb VA, 6.60 kb R2C2-intron and 6.57 kb R2C5-intron fragments had been digested out of pCR-Blunt. The PCR products were excised from the gel using a scalpel and the DNA purified using a Qiaquick Gel Extraction kit.

The pCR-Blunt.E4 and pCR-Blunt.VA were Sanger sequenced with the M13 F and M13 R primers and confirmed to be correct.

2.5.2.4: Cloning of Subcloned PCR Fragments into pDonor

The pDonor plasmid was digested with MluI+NheI and subjected to agarose gel electrophoresis on a 0.8% agarose gel containing 1×TAE and 1×SYBR Safe at 80 V for 1 hour The 6.05 kb fragment was excised from the gel using a scalpel and the DNA purified using a Qiaquick Gel Extraction kit. The gel purified fragment was then dephosphorylated by adding 1 µl of FastAP dephosphorylase (Thermo Fisher, Cat. No. EF0651) to the digest and incubating it at 37° C. for 10 minutes followed by 75° C. for 5 minutes. Ligation reactions were then set up containing 2 µl digested pDonor, 6 µl of the gel purified E4, VA, R2C2-intron and R2C5-intron digests, 1 µl ligation buffer and 1 µl T4 DNA ligase. The reactions were incubated at 16° C. overnight in a thermal cycler.

A volume of 2 µl of each ligation was used to transform vials of Stb13 chemically competent E. coli (Thermo Fisher, Cat. No. C737303). The transformed cells were spread on an LB agar plate containing 50 µg/ml Kanamycin and incubated at 37° C. overnight.

Colonies were subcultured on LB agar plates, the subcultured colonies were grown in broth cultures and the plasmid DNA was extracted as in 2.5.1. The concentration of DNA in each of the minipreps was calculated using a Nanodrop and 1 ug of each of the plasmid preps was digested. The pDonor.E4 clones were digested with KpnI, the pDonor.VA clones with XbaI, and pDonor.R2C2-intron and pDonor.R2C5-intron with SpeI. The digests were incubated at 37° C. for 2 hours and then subjected to gel electrophoresis as 2.5.1.

These gels showed that pDonor.E4, pDonor.VA, pDonor.R2C2-intron and pDonor.R2C5-intron clones had the correct restriction profile. pDonor.R2C2-intron and pDonor.R2C5-intron were Sanger sequenced. The sequencing showed that the correct R2C2-intron and R2C5-intron fragments had been cloned into pDonor.

2.6 Cloning of Rep2 shRNA into pG3.Ptet-T6-MCS-polyA

Rep2 shRNA was cloned downstream of the Ptet-T6 promoter.

The plasmids pG3.AAV rep2 shRNA11 and pG3.Ptet-T6-MCS-polyA were digested with NheI+XhoI and subjected to agarose gel electrophoresis on 0.8% agarose gels containing 1×TAE and 1×SYBR Safe at 80 V for 70 minutes.

The 114 bp rep2 shRNA 11 fragment and 2.31 kb pG3.Ptet-T6-MCS-polyA fragment were excised from the gel and the DNA purified using a Qiaquick Gel Extraction kit. A ligation reaction was then set up containing 2 µl of the gel purified pG3.Ptet-T6-MCS-polyA, 6 µl of the gel purified rep2 shRNA 11, 1 µl ligation buffer and 1 µl T4 DNA ligase. The reaction was incubated at 16° C. overnight in a thermal cycler.

A volume of 2 µl of the ligation was used to transform a vial of Stb13 chemically competent E. coli. The transformed cells were spread on an LB agar plate containing 50 µg/ml Kanamycin and incubated at 37° C. overnight.

Colonies were subcultured, grown and DNA extracted as in 2.5.1 and then digested with MluI+XbaI. The digests were incubated at 37° C. for 2 hours and then subjected to gel electrophoresis.

The gel showed that digests released the correct sized 639 bp fragment. This plasmid was given the name pG3.Ptet-T6-rep2 shRNA 11. The DNA fragment was excised from the gel using a scalpel and the DNA purified. A ligation reaction was then set up containing 2 µl MluI+NheI digested pDonor, 6 µl of the gel purified Ptet-T6-rep2 shRNA 11 fragment, 1 µl ligation buffer and 1 µl T4 DNA ligase. The reaction was incubated at 16° C. overnight in a thermal cycler.

A volume of 2 µl of the ligation was used to transform a vial of Stb13 chemically competent E. coli. The transformed cells were spread on an LB agar plate containing 50 µg/ml Kanamycin and incubated at 37° C. overnight. The following day, the plates were inspected and many colonies had grown on the plate.

Colonies were subcultures, grown and DNA extracted as in 2.5.1, and then digested with XhoI. The digests were incubated at 37° C. for 2 hours and then subjected to gel electrophoresis on a 0.8% agarose gel containing 1×TAE and 1×SYBR Safe at 80 V for 70 minutes. The gel showed that all clones had the correct restriction pattern of 4.03 kb and 2.67 kb fragments. This plasmid was given the name pDonor.Ptet-T6-rep2 shRNA 11.

2.7 Sequential Cloning of the Expression Cassettes from pDonor into BAC

As with each sequential cloning step the BAC construct would become larger, use of standard restriction enzymes to cut and clone each additional expression cassette would soon become difficult due to multiple cut sites for each enzyme in the construct. Further, the inclusion of 2×cHS4 insulators between each expression cassette would mean that the construct would contain many repeats, making Gibson assembly prohibitive. For these reasons, each expression cassette was cloned using iBrick cloning (Liu et al., (2014) PLoS One 9: e110852). This method of cloning utilises the meganuclease restriction sites PI-PspI and I-SceI, which recognise sites long enough not to appear in any of the expression cassettes intended to be cloned into the BAC. The cut sites of these enzymes are also asymmetrical and produce compatible overhangs. This means that each expression cassette in the donor plasmid (pDonor) upstream of 2×cHS4 can be digested out of this plasmid with I-SceI located at the 5' end and PI-PspI located downstream of the 2×cHS4 at the 3' end. This fragment is then directionally cloned into a single PI-PspI site in the BAC which would abrogate the PI-PspI site at the 5' end of the fragment and create a new PI-PspI site downstream of the expression cassette allowing for the cloning of the next expression cassette into this site.

Primer Sequences

| Name | Sequence |
|---|---|
| pSMARTBAC Gib F A | GTGGATCGGTGGGCAGTTTAC (SEQ ID NO: 26) |
| pSMARTBAC-tTA Gib R A | ACTAGTCAATAATCAATGTCTCTATAGTGTCACCTAAATA C (SEQ ID NO: 27) |
| pSMARTBAC-tTA Gib F B | TGGCAAACAGCTATTATGGGTATTATGGGTACTGACCCTA TAGTGAGTCG (SEQ ID NO: 28) |
| pSMARTBAC Gib R B | GGCTCTGCACCGTATTGAAAC (SEQ ID NO: 29) |
| tTA-pSMARTBAC Gib F C | TATTTAGGTGACACTATAGAGACATTGATTATTGACTAGT (SEQ ID NO: 30) |
| tTA-pSMARTBAC Gib R C | ACCCATAATACCCATAATAGCTGTTTGCCATAAGATACAT TGATGAGTTTGG (SEQ ID NO: 31) |
| E2A I-SceI F | ATTACCCTGTTATCCCTAGCCCGGGCGACCGCACCCTGTG (SEQ ID NO: 32) |
| E2A PI-PspI R | ACCCATAATACCCATAATAGCTGTTTGCCAGTACCCAACT CCATGCTTAACAGTCC (SEQ ID NO: 33) |

All primers were obtained from ThermoFisher Scientific. Underlined nucleotides denote a 5' overhang included in the primer to provide a region of overlap in the PCR product with the sequence that it was to be assembled adjacent to in the Gibson cloning reaction.

2.7.1: PCR of pSMARTBAC2 and GSKCOtTA-IR-Zeo$^R$ for Gibson Assembly

The commercially available BAC, pSMART BAC 2 was chosen to be the backbone of the stable rAAV construct. This BAC confers resistance to chloramphenicol to E. coli and is maintained at 1 copy per cell until its origin of replication (OriV) is bound by TrfA, which is inducible by arabinose in BAC-Optimised Replicator cells. The first expression cassette to be cloned into the backbone was GSKCOtTA-IR-Zeo$^R$. It was cloned into pSMARTBAC2 by Gibson assembly. Overlapping primers were designed to amplify pSMARTBAC2 as 2 separate fragments lacking the multiple cloning site containing cut sites for several standard restriction enzymes (Fragments 1: pSMARTBAC Gib F A & pSMARTBAC-tTA Gib R A and 2: pSMARTBAC-tTA Gib F B & pSMARTBAC Gib R B) and GSKCOtTA-IR-ZeoR as a single fragment (Fragment 3: tTA-pSMARTBAC Gib F C & tTA-pSMARTBAC Gib R C). The overlap in the primers between the 3' end of GSKCOtTA-IR-Zeo$^R$ and pSMARTBAC2 contained the recognition sequence for PI-PspI so that each subsequent genetic element could be cloned into this site by iBrick cloning.

Each PCR reaction had a total volume of 25 μl and the components set out in 2.5.1.

The PCR thermal cycling was performed using a Bio-Rad C1000 Touch thermal cycler. The conditions for all 3 reactions were as follows:

| | | |
|---|---|---|
| 98° C. | 30 sec | 1 cycle |
| 98° C. | 15 sec | ] 4 x |
| 55° C. | 15 sec | |
| 72° C. | 3:30 min | |
| 98° C. | 15 sec | ] 32 x |
| 62° C. | 15 sec | |
| 72° C. | 3:30 min | |
| 72° C. | 5:00 min | 1 cycle |
| 4° C. | Hold | |

The PCR reactions were then subjected to gel electrophoresis. The gel confirmed that the correct sized fragments had been amplified in each reaction. The fragments were excised and the DNA purified.

Equal volumes of 3.3 μl of each of the three purified PCR fragments were combined in 0.2 ml PCR tubes and 10 μl of NEBuilder HiFi DNA Assembly Mastermix (NEB, Cat. No. E2621) was added and mixed by pipetting up and down. The tubes were incubated in the Thermal Cycler at 50° C. for 1 hour.

Following the assembly reaction, a volume of 2 μl of each reaction was used to transform vials of 10-beta competent E. coli. The transformed cells were spread on LB agar plates containing 34 μg/ml Chloramphenicol and incubated at 37° C. overnight.

Colonies were picked from the plate and subcultured on LB agar plates containing 34 μg/ml Chloramphenicol. The subcultured colonies were grown in 3 ml LB broth cultures containing 12.5 μg/ml Chloramphenicol overnight with gentle agitation. The plasmid DNA was extracted from the broth cultures using a QiaPrep Spin Miniprep kit. The concentration of DNA in each of the minipreps was calculated using a Nanodrop. The BAC preps were digested with NdeI, creating fragments of 6977 bp and 3732 bp. The digests were incubated at 37° C. for 2 hours and then subjected to gel electrophoresis, which confirmed that the correct restriction patterns.

2.7.2: Cloning of 2×cHS4 and Adenovirus 2 E2A

Next 2×cHS4 was cloned downstream of GSKCOtTA-IR-Zeo$^R$ and then the adenovirus E2A region. Since it contains an internal restriction site for MluI, E2A could not be subcloned into pDonor upstream of 2×cHS4. As a result, E2A needed to be cloned individually, rather than as a combined fragment with 2×cHS4 at the 3' end.

The Adenovirus 2 E2A region was PCR amplified from pG3.Ad2 Helper GSK using the primers E2A I-SceI F and E2A PI-PspI R and Q5 DNA polymerase (NEB, Cat. No. M0491S). The conditions used on the Bio-Rad C1000 Touch thermal cycler were as below.

| | | |
|---|---|---|
| 98° C. | 30 sec | 1 cycle |
| 98° C. | 15 sec | ] 35 x |
| 59° C. | 15 sec | |
| 72° C. | 3:45 min | |
| 72° C. | 2:00 min | 1 cycle |
| 4° C. | Hold | |

The E2A PCR, which contains an I-SceI site at the 5' end, and a PI-PspI site at the 3' end was subjected to gel electrophoresis. The correct sized 5.39 kb fragment was present and was excised from the gel and the DNA purified using a Qiaquick Gel Extraction kit. The purified DNA was ligated into pCR-Blunt II TOPO and this ligation used to transform a vial of OneShot TOP10 chemically competent E. coli which were spread on an LB agar plate containing 50 μg/ml Kanamycin and incubated overnight at 37° C. The colonies were subcultured overnight and the subcultured colonies were grown as in 2.5.1. The following day, the plasmid DNA was extracted from the broth cultures using a QiaPrep Spin Miniprep kit. The concentration of DNA was calculated and 1 μg of each plasmid was digested with I-SceI in a volume of 30 μl at 37° C. for 2 hours. As PI-PspI does not work in any compatible buffer with other enzymes, the volume was increased by adding 22.4 μl additional sterile H$_2$O and then 6 μl of the buffer, 0.6 μl 100×BSA solution and 1 μl PI-PspI was added so the volume of the digests was now 60 μl. Additionally, in order to obtain a 2×cHS4 fragment with I-SceI and PI-PspI at the 5' and 3' end respectively, pDonor was digested with these enzymes in the same way. These digests were incubated at 65° C. for 2 hours and then subjected to gel electrophoresis.

The gel confirmed that the correct 5.36 kb fragment was released from the digests of pCR-Blunt.E2A clones and the correct 2.76 kb fragment was released from pDonor. These fragments were excised from the gel and the DNA purified. The pCR-Blunt colonies were Sanger sequenced with the M13 F and M13 R. The sequencing confirmed that the E2A has been cloned.

The miniprep of pSMARTBAC.GSKCOtTA-IR-ZeoR clone 1 was diluted in sterile distilled water and used to transform electrocompetent BAC replicator cells that were then grown overnight on a LB agar plate containing 34 μg/ml Chloramphenicol. A colony from this plate was used to infect an LB broth culture containing 12.5 μg/ml Chloramphenicol and 1×Arabinose induction solution and grown overnight at 37° C. with gentle agitation. The following day, plasmid DNA was extracted from the broth culture using a QiaPrep Spin Miniprep kit. The concentration of DNA in the miniprep was calculated using a Nanodrop and 1 μg of DNA was digested with PI-PspI in a volume of 30 µl at 65° C. for 2 hours in a thermal cycler. Following this, the reaction was cooled to room temperature and 1 unit of FastAP dephosphorylase was added. The reaction was then incubated at 37° C. for 10 minutes and then 75° C. for 5 minutes to deactivate the FastAP Thermosensitive Alkaline Phosphatase (Fast AP) (Thermo Fisher, Cat. No. EF0651).

A ligation reaction was then set up containing 2 µl digested pSMARTBAC2.GSKCOtTA-IR-ZeoR, 6 µl purified 2×cHS4 digest, 1 µl ligation buffer and 1 µl T4 DNA ligase and the reaction was incubated at 16° C. overnight in a thermal cycler.

A volume of 0.6 µl of the ligation reaction was used to transform electrocompetent BAC replicator cells, colonies grown in a culture and DNA extracted as above. 1 µg of each plasmid was digested with SwaI and MluI in NEB buffer 3.1 at 37° C. for 2 hours and then subjected to gel electrophoresis.

The gel confirmed that the correct restriction pattern of a 10,690 bp and 2784 bp fragment was present in all the clones. A permanent glycerol stock was made of clone 1 and the construct was given the shortened name BAC2.

In order to clone E2A into the BAC2 PI-PspI site, clone 1 of the BAC2 clones was digested with PI-PspI and dephosphorylated with FastAP as described previously. A ligation reaction was then set up containing 2 µl digested BAC2 clone 1, 6 µl purified E2A I-SceI+PI-PspI digest, 1 µl ligation buffer and 1 µl T4 DNA ligase. The reaction was incubated at 16° C. overnight in a thermal cycler.

A volume of 0.6 µl of this reaction was used to transform electrocompetent BAC replicator cells, colonies grown in a culture and DNA extracted as above. 1 µg of each plasmid was digested with EcoRI+XbaI. The digests were subjected to gel electrophoresis. The gel confirmed that all clones had the correct 9.3, 7.8 and 1.74 kb fragments when digested with these two enzymes.

The colonies were grown overnight in 80 ml LB broth cultures containing 12.5 µg/ml Chloramphenicol and 1×Arabinose induction solution at 37° C. with gentle agitation overnight. The following day, the plasmid DNA was extracted from the broth cultures using a Qiagen Midiprep kit. These preps were Sanger sequenced. The sequence data confirmed that E2A had been successfully cloned into the BAC downstream of 2×cHS4. This construct was given the shortened name BAC3.

Next, another 2×cHS4 was cloned downstream of E2A. The midiprep of BAC3 clone 1 was digested with PI-PspI and dephosphorylated with FastAP as described previously. A ligation reaction was then set up containing 2 µl digested BAC3 clone 1, 6 µl purified 2×cHS4 I-SceI+PI-PspI digest, 1 µl ligation buffer and 1 µl T4 DNA ligase. The reaction was incubated at 16° C. overnight in a thermal cycler.

A volume of 0.6 µl of this reaction was used to transform electrocompetent BAC replicator cells, then grown overnight on a LB agar plate containing 34 µg/ml Chloramphenicol. The following day 2 colonies had grown on the plate and were picked and subcultured overnight. These subcultured colonies were used to infect 3 ml LB broth cultures containing 12.5 µg/ml Chloramphenicol which were incubated overnight at 30° C. with gentle agitation. The following day, 1×Arabinose induction solution solution was added and the cultures grown for a further 3 hours. The plasmid DNA was extracted from the broth cultures using a QiaPrep Spin Miniprep kit. The concentration of DNA in each of the minipreps was calculated using a Nanodrop and 1 µg of each plasmid was digested with SwaI+XhoI. The digests were subjected to gel electrophoresis on a 0.8% agarose gel containing 1×TAE and 1×SYBR Safe at 80 V for 70 minutes. These digests showed that both colonies had the correct 17,083 and 4519 bp fragments when digested with these 2 enzymes. This construct was given the shortened name BAC4.

2.7.3: Cloning of Adenovirus 2 E4.2×cHS4

BAC4 was digested with PI-PspI and dephosphorylated with FastAP as described previously. The plasmid pDonor.E4 was digested with I-SceI at 37° C. for 3 hours in a total reaction volume of 30 µl. Following this, the volume of the reaction was increased to 60 µl by addition of 22.4 µl of sterile H₂O, 6 µl 10×PI-PspI reaction buffer, 0.6 µl 100×BSA solution and 1 µl PI-PspI. The reaction was then incubated at 65° C. for a further 3 hours and then subjected to gel electrophoresis.

The 5.7 kb E4.2×cHS4 fragment was excised from the gel and the DNA purified. A ligation reaction was then set up containing 2 µl digested BAC4, 6 µl purified E4.2×cHS4 I-SceI+PI-PspI digest, 1 µl ligation buffer and 1 µl T4 DNA ligase. The reaction was incubated at 16° C. overnight in a thermal cycler.

A volume of 0.6 µl of this reaction was used to transform electrocompetent BAC replicator cells, grown overnight, subcultured overnight, grown in LB broth overnight at 30° C. and then DNA extracted as with BAC4 above. 1 µg of each plasmid was digested with HpaI. The digests were subjected to gel electrophoresis on a 0.8% agarose This gel showed that all clones had the correct restriction profile of a 20.69 kb and a 6.61 kb fragment when digested with HpaI This construct was given the shortened name BAC5.

2.7.4: Cloning of Adenovirus 2 VA.2×cHS4

BAC5 was digested with PI-PspI and dephosphorylated with FastAP as described previously. The plasmid pDonor.VA was digested with I-SceI+SfiI at 37° C. for 3 hours in a total reaction volume of 30 µl. SfiI was used to cut the backbone of the plasmid as otherwise it would produce a fragment that would be impossible to separate from VA.2× cHS4. Following this, the volume of the reaction was increased to 60 µl by addition of 22.4 µl of sterile H₂O, 6 µl 10×PI-PspI reaction buffer, 0.6 µl 100×BSA solution and 1 µl PI-PspI. The reaction was then incubated at 65° C. for a further 3 hours and then subjected to gel electrophoresis on a 0.8% agarose gel containing 1×TAE and 1×SYBR Safe at 80 V for 70 minutes.

The 3.25 kb VA.2×cHS4 fragment was excised from the gel with a scalpel and the DNA purified using a Qiaquick Gel Extraction kit. A ligation reaction was then set up containing 2 µl digested BAC5, 6 µl purified VA.2×cHS4 I-SceI+PI-PspI digest, 1 µl ligation buffer and 1 µl T4 DNA ligase. The reaction was incubated at 16° C. overnight in a thermal cycler.

A volume of 0.6 µl of this reaction was used to transform electrocompetent BAC replicator cells, grown overnight, subcultured overnight, grown in LB broth overnight at 30° C. and then DNA extracted as above. 1 µg of each plasmid was digested with HpaI+SwaI. The digests were subjected to gel electrophoresis on a 0.8% agarose gel. This gel showed that clones 2-4 had the correct 20.69 kb, 8.46 kb and 1.4 kb fragments. This construct was given the shortened name of BAC6.

2.7.5: Cloning of rep2cap2-intron.2×cHS4 and rep2cap5-intron.2×cHS4

As construct BACs for the stable production of AAV2 (R2C2) and AAV5 (R2C5) were made, there was a divergence in the BACs following this stage.

BAC6 was digested with PI-PspI and dephosphorylated with FastAP as described previously. The plasmids pDonor.R2C2-intron and pDonor.R2C5-intron were digested with I-SceI at 37° C. for 3 hours in a total reaction volume of 30 μl. Following this, the volume of the reactions was increased to 60 μl by addition of 22.4 μl of sterile $H_2O$, 6 μl 10×PI-PspI reaction buffer, 0.6 μl 100×BSA solution and 1 μl PI-PspI. The reactions were then incubated at 65° C. for a further 3 hours and then subjected to gel electrophoresis on a 0.8% agarose gel.

The 9.10 kb and 9.07 kb R2C2-intron.2×cHS4 and R2C5-intron.2×cHS4 fragments were excised from the gel and the DNA purified. Ligation reactions were then set up containing 2 μl digested BAC6, 6 μl purified R2C2-intron.2×cHS4 or R2C5-intron.2×cHS4 I-SceI+PI-PspI digest, 1 μl ligation buffer and 1 μl T4 DNA ligase. The reactions were incubated at 16° C. overnight in a thermal cycler.

A volume of 0.6 μl of these reactions were used to transform electrocompetent BAC replicator cells, grown overnight, subcultured overnight, grown in LB broth overnight at 30° C. and then DNA extracted as above. 1 μg of each plasmid was digested with ClaI+SwaI. The digests were subjected to gel electrophoresis on a 0.8% agarose gel. The gel showed that the digests had the correct 20.59 kb, 10.15 kb, 4.84 kb and 3.08 kb fragments. This construct was given the shortened name of BAC7a.

The R2C5-intron BAC ligation failed to transform the BAC replicator electrocompetent cells, and so the ligation was used to transform chemically competent Stb13 cells and subsequently processed as above with electrocompetent BAC replicator cells. 1 μg of each plasmid was digested with ClaI+SwaI. The digests were subjected to gel electrophoresis on a 0.8% agarose gel. The digests showed the correct restriction profile for insertion R2C5-intron.2×cHS4 into BAC6 (21.59, 10.15, 4.82 and 3.08 kb fragments). This construct was given the shortened name BAC7b.

2.7.6: Cloning of the rep2 and E1A-Targeting shRNA

The rep2 shRNA 11 was cloned into the BAC. BAC7a and BAC7b were digested with PI-PspI and dephosphorylated with FastAP as described previously. The plasmid pDonor.Ptet-T6-rep2 shRNA 11 was digested with I-SceI at 37° C. for 3 hours in a total reaction volume of 30 μl. Following this, the volume of the reaction was increased to 60 μl by addition of 22.4 μl of sterile $H_2O$, 6 μl 10×PI-PspI reaction buffer, 0.6 μl 100×BSA solution and 1 μl PI-PspI. The reaction was then incubated at 65° C. for a further 3 hours and then subjected to gel electrophoresis on a 0.8% agarose gel.

The smaller 3.15 kb fragment was excised from the gel and the DNA purified using a Qiaquick Gel Extraction kit. Ligation reactions were then set up containing 2 μl digested BAC7a or BAC7b, 6 μl purified Ptet-T6-rep2 shRNA 11.2×cHS4 I-SceI+PI-PspI digest, 1 μl ligation buffer and 1 μl T4 DNA ligase. The reactions were incubated at 16° C. overnight in a thermal cycler.

A volume of 0.6 μl of these reactions were used to transform electrocompetent BAC replicator cells that were then grown overnight on LB agar plates containing 34 μg/ml Chloramphenicol. Colonies from the Ptet-T6-rep2 shRNA 11.2×cHS4 into BAC7a ligation plate and Ptet-T6-rep2 shRNA 11.2×cHS4 into BAC7b ligation plate were picked and subcultured overnight and then subsequently processed as before. 1 μg of each plasmid was digested with NdeI+SwaI. The digests were subjected to gel electrophoresis on a 0.8% agarose gel.

The gel showed that the correct restriction profiles for Ptet-T6-rep2 shRNA 11.2×cHS4 cloned into BAC7a and Ptet-T6-rep2 shRNA 11.2×cHS4 cloned into BAC7b. These constructs were given the name BAC8a and BAC8b, respectively. BAC8a was Sanger sequenced. The result showed that GSKCOtTA-IR-Zeo, E2A, E4, VA, R2C2-intron and Ptet-T6-rep2 shRNA 11 were all present and correct in this construct.

Next the E1A shRNA 5 was cloned into the BAC. BAC8a was digested with PI-PspI and dephosphorylated with FastAP as described previously. An I-SceI+PI-PspI digested Ptet-T6-E1A shRNA 5.2×cHS4 fragment was used in a ligation with this BAC digest. The ligation contained 4 μl of digested BAC, 4 μl of digested Ptet-T6-E1A shRNA 5.2×cHS4, 1 μl 10×ligase buffer and 1 μl T4 DNA ligase. The reaction was incubated at 16° C. overnight in a thermal cycler.

A volume of 0.6 μl of this reaction was used to transform electrocompetent BAC replicator cells that were then grown overnight on LB agar plates containing 34 μg/ml Chloramphenicol. The following day, no colonies had grown on the plate. The ligation was used to transform a vial of Stb13 E. coli and processed as above. 1 μg of each plasmid was digested with EcoRI. The digests were subjected to gel electrophoresis on a 0.8% agarose gel. This gel showed the correct restriction profile for insertion of Ptet-T6-E1A shRNA 5.2×cHS4 into BAC8a, containing an additional 3.0 kb fragment compared to an EcoRI digest of BAC8a. The construct was given the name BAC9a.

2.7.7 Cloning of the GFP Transfer Vector into BAC

Before cloning the GFP transfer vector (pDonor.AAV2.C.GFP.P2a.fLuc.W6) into BAC, the transfer vector was modified to incorporate the E. coli ssb gene (GenBank (J01704)) with its native promoter.

The EGFP transfer vector plasmid, pG.AAV2.C.GFP.P2a.fLuc.W6, has a unique EcoRI restriction site outside of the transfer vector sequence flanked by the ITRs. The plasmid was digested with EcoRI. The digest was incubated at 37° C. for 2 hours and then subjected to gel electrophoresis on a 0.8% agarose gels. The linearized plasmid was excised from the gel and the DNA purified. The purified fragment was dephosphorylated with FastAP. This was then used in a ligation with an EcoRI digested ssb+ native promoter fragment. The ligation reaction contained 2 μl digested transfer vector, 6 μl digested ssb+native promoter fragment, 1 μl 10×ligase buffer and 1 μl T4 DNA ligase. The ligation was incubated overnight at 16° C. in a thermal cycler. This construct was named pDonor.AAV2.C.GFP.P2a.fLuc.W6.ssb.

To clone the GFP transfer vector into a BAC containing the rep/cap gene and adenovirus helper genes, BAC8a and BAC9a were digested with PI-PspI and dephosphorylated with FastAP as described previously. The transfer vector plasmid pDonor.AAV2.C.GFP.P2a.fLuc.W6.ssb was digested with I-SceI at 37° C. for 3 hours in a total reaction volume of 30 μl. Following this, the volume of the reaction was increased to 60 μl by addition of 22.4 μl of sterile $H_2O$, 6 μl 10×PI-PspI reaction buffer, 0.6 μl 100×BSA solution and 1 μl PI-PspI. The reactions were then incubated at 65° C. for a further 3 hours and then subjected to gel electrophoresis on a 0.8% agarose gel.

Figure 5:
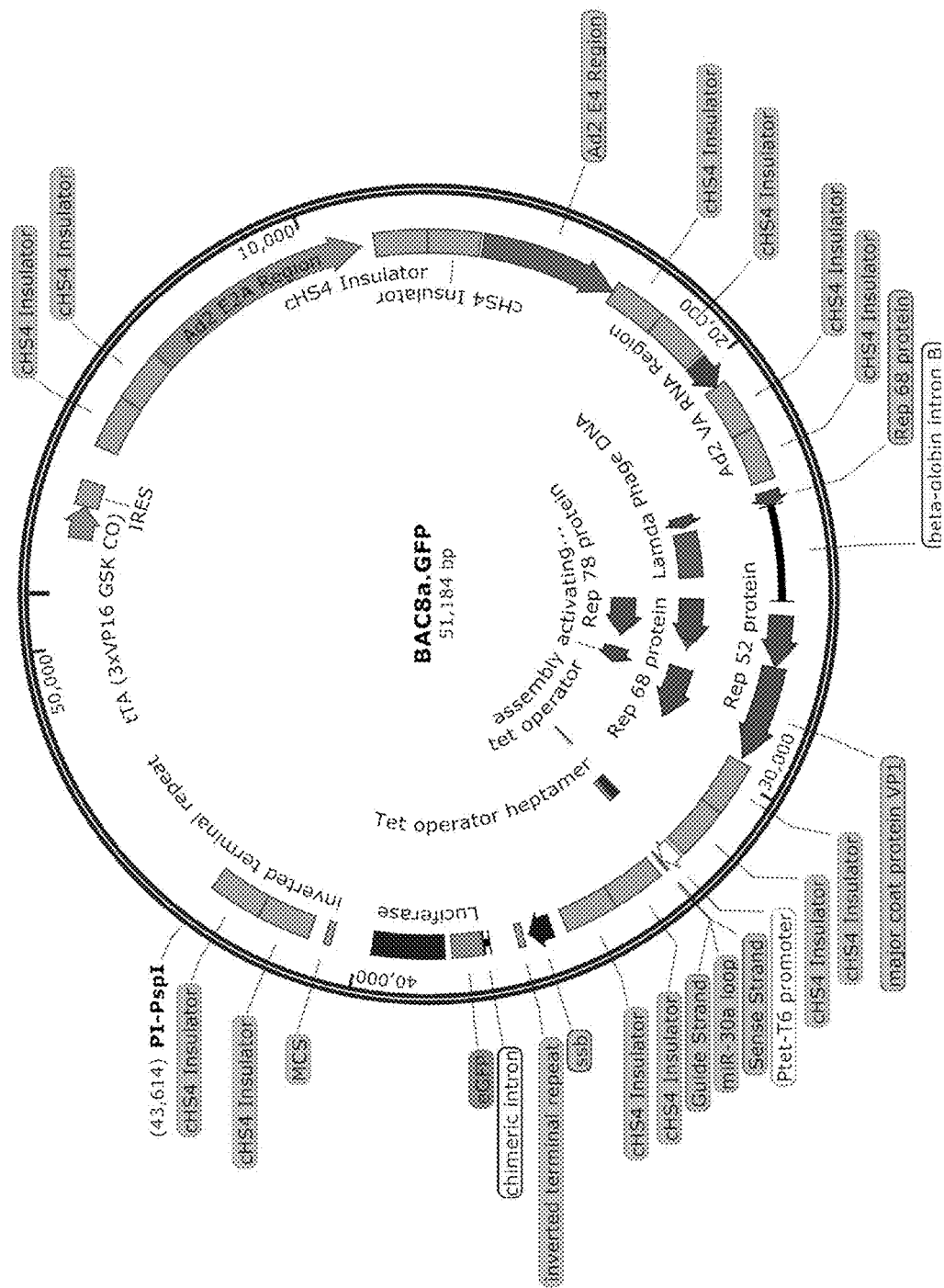
FIG. 5: A plasmid map of BAC8a-GFP.
Figure 6:
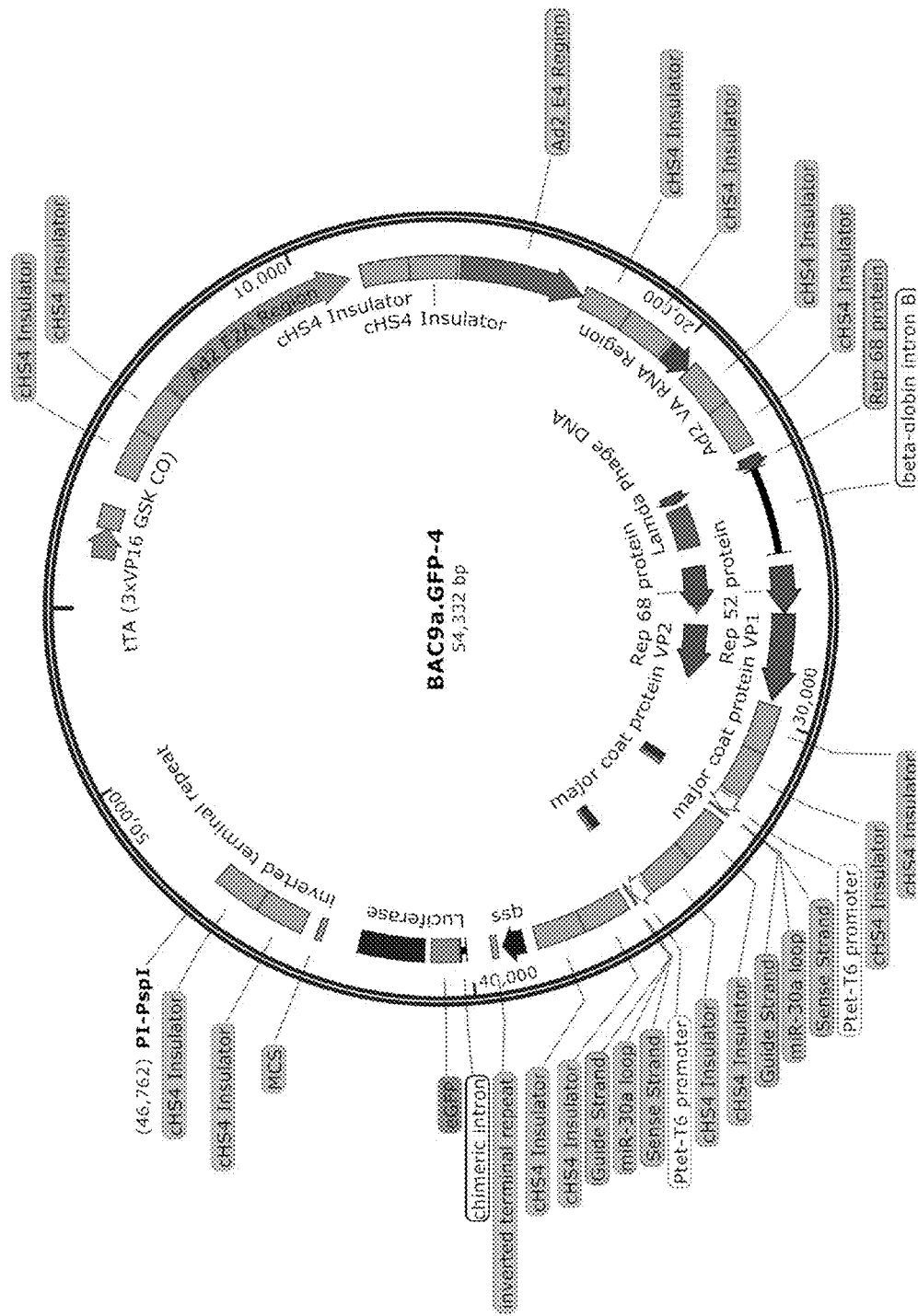
FIG. 6: A plasmid map of BAC9a-GFP.

For each reaction, the smaller fragment was excised from the gel and the DNA purified. Ligation reactions were then set up containing 2 μl digested BAC8a or BAC9a, 6 μl purified AAV2.C.GFP.P2a.fLuc.W6.ssb I-SceI+PI-PspI digest, 1 μl ligation buffer and 1 μl T4 DNA ligase. The reactions were incubated at 16° C. overnight in a thermal cycler. The constructs containing the GFP transfer vector were given the name BAC8a-GFP or BAC9a-GFP, respectively. The plasmid maps of BAC8a-GFP and BAC9a-GFP are shown in FIGS. 5 and 6, respectively.

Example 3: Generation of AAV Stable Producer Cell Line (Suspension Cells)

A stable cell line was established by transfecting AdVec 293 suspension cells with BAC9a-GFP. As a transient transfection control, the AdVec 293 cells were also co-transfected with a rep/cap plasmid, a helper plasmid (carrying helper genes from adenovirus) and pG.AAV.CMV.GFP.P2A.fluc.W6 (transfer vector with ITR flanking GFP transgene) at a 1:1:1 ratio based on molar ratios.

3.1 AdVec 293 RS-D01 Suspension Cells

AdVec suspension cells were maintained in BalanCD media (with 2% GlutaMAX and 1% Pluronic F-68) at $0.4 \times 10^6$ cell/ml and split every 2-3 days. Cells are incubated 37° C., 5% $CO_2$, 110 rpm. Small scale cultures were maintained at higher rotation (140 rpm) to aid aeration.

3.2 Transfection of AdVec 293 RS-D01 Suspension Cells

Prior to transfection, cells were centrifuged at 500 rpm for 10 min at 4° C., the supernatant removed and the cell pellet resuspended in fresh pre-warmed BalanCD media, counted and seeded at $1 \times 10^6$ cells/ml in 125 ml Erlenmeyer flask with vented cap.

For each ml of cells to be transfected, 1 µg plasmid and 1.3 µl PEIpro were used.

For control rAAV transfections using GSK helper and rep/cap plasmids with pG.AAV.CMV.GFP.P2A.fluc.W6, plasmids were transfected at 1:1:1 ratio based on molar ratios.

3.2.1 Preparation of Transfection Mix

1) Label two bijoux
   a) DNA & OptiMEM
   b) B—PEIpro & OptiMEM
2) Make up transfection mix:—
   a) Add plasmid DNA to pre-warmed OptiMEM in bijou A
   b) Add PEIpro to pre-warmed OptiMEM in bijou B
   c) Incubate at room temperature for 5 min
   d) Add DNA/OptiMEM to PEIpro/OptiMEM
   e) Incubate at room temperature for 30 min
   f) Add transfection mix dropwise to cell suspensions.
   g) Incubate transfections in shaking incubator for 72 h at 37° C., 5% $CO_2$, 140 rpm.

Control rAAV transfections were harvested 72 h post-transfection by centrifugation at 2000×g for 5 min. Supernatant was removed and cells lysed in AAV lysis buffer.

3.2.2 Determination of Transfection Efficiency by Flow Cytometry and Microscopy 72 h post-transfection 100 µl culture was added to 96 well black flat-bottomed plate.

The cells were imaged using Olympia microscope and Pixar InStudio software.

After imaging, 100 µl 4% PFA solution was added per well. Cells were analysed for GFP expression on MACS Quant 10 using FlowJo software.

FIG. 7(A) shows microscope images of AdVec RS-D01 cells 72 h post-transfection. FIG. 7(B) shows analysis of GFP positive cells by MACS Quant analyser and FlowJo Software after transfection.

Figure 7:
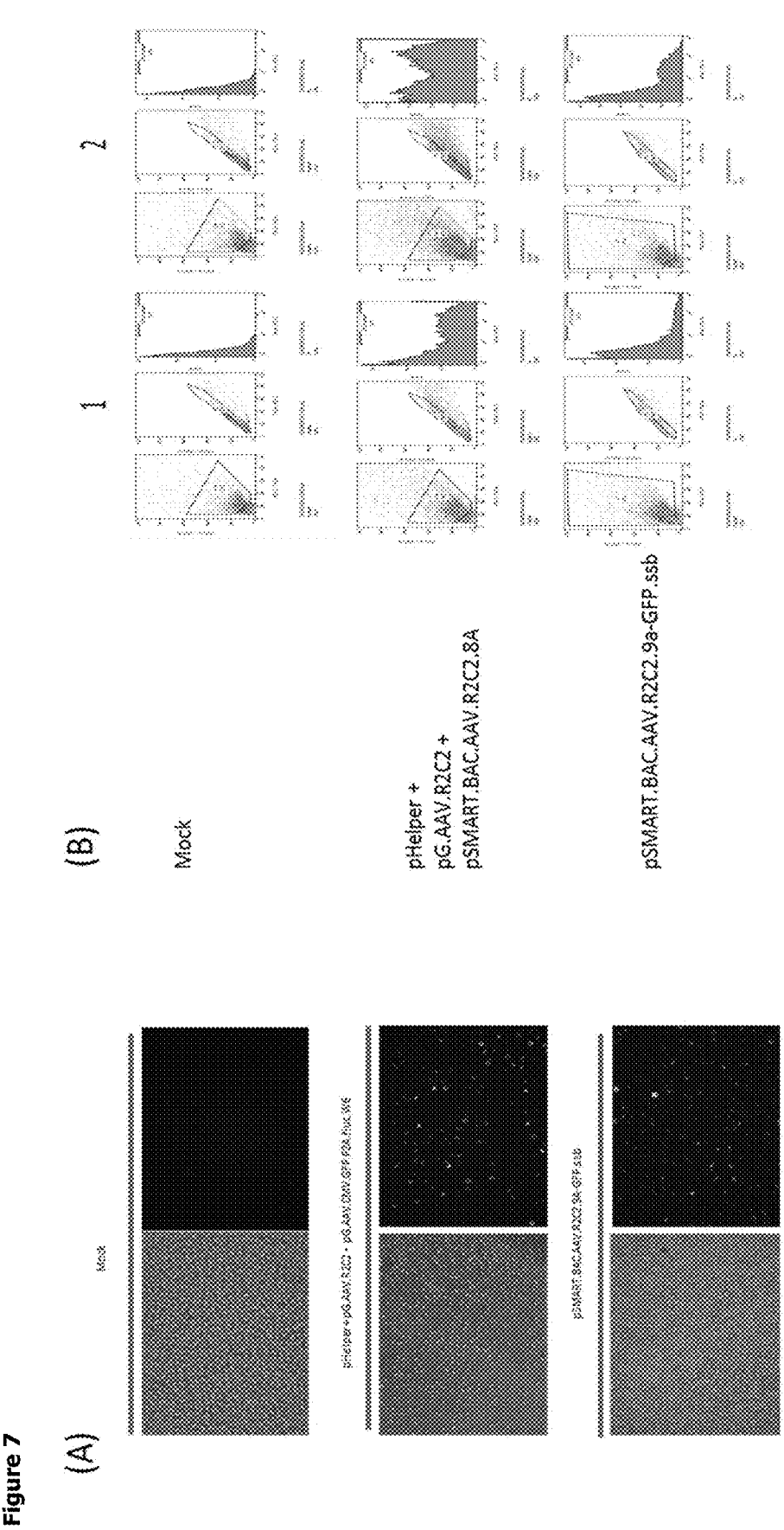
FIG. 7: Microscope images of AdVec RS-D01 cells 72 h post-transfection and analysis of GFP positive cells.

Images and flow cytometry data of FIG. 7 shows that BAC9A-GFP is expressing after transfection into AdVec RS-D01 suspension cells. Transfection efficiency is lower than triple plasmid system but this is expected as BAC9A-GFP is a bigger construct.

3.2.3 Determination of Cell Number and Cell Viability

100 µl of transfection culture was added to 900 µl BalanCD in a ViCell cup and analysed using ViCell Xr.

3.3 Small Scale Induction of rAAV from Transfected Cells Using Doxycycline 72 h post-transfection 1 ml culture was added to 2 wells of 24 deep-well suspension culture plate. In one well, 1 ml BalanCD media was added (uninduced). In the other, 1 ml BalanCD media with 4 µg/ml Doxycycline (2 µg/ml final concentration, Induced). Cells were incubated at 37° C., 5% $CO_2$, 140 rpm for 48 h.

48 h post-induction, cells were harvested by centrifugation at 2000×g for 5 min. Supernatant was removed and cells lysed in AAV lysis buffer (50 mM Tris, 150 mM NaCl, 2 mM $MgCl_2$, pH 8.5) 100 µl per ml of cells, at room temperature for 5 min, vortexed then frozen at −80° C. Cell lysis underwent three rounds of freeze, thaw at −80° C. and 37° C. The lysate was treated with Benzonase™ (50 U/ml) at 37° C. for 30 min then clarified by centrifugation at 4000×g for 20 min. Lysate was removed to a fresh pre-chilled tube and aliquoted ~2×5 µl for DNA extraction for qPCR analysis, 4×10 µl for transductions and 50 µl.

3.4 qPCR Determination of Produced rAAV from Cell Lysate

DNAseI-resistant AAV genome were isolated from intact particles using the Roche High Pure Viral Nucleic Acid Kit and quantified by ITR2 qPCR.

3.4.1 DNA Isolation Using Roche High Pure Viral Nucleic Acid Kit

5 µl virus lysate was defrost on ice and 195 µl 1×D-PBS was added per sample. Viral DNA was extracted using Roche High Pure Viral Nucleic Acid Kit, following the manufacturer's protocol.

3.4.2 ITR2 qPCR qPCR titration method is based on quantification of AAV ITR sequences as described in Aurnhammer et al. (Aurnhammer et al., (2012) Human gene therapy methods 23, 18-28).

Sample Dilution

Purified AAV genomes from 6.4.1 were diluted in 96 well plates using DEPC treated water.

Sample Dilution Scheme for ITR2 qPCR

| Sample dilution | Water | Sample | Final Dilution |
| --- | --- | --- | --- |
| S1-0 | 95 uL | 5 uL processed sample undiluted | 1:20 |
| S1-1 | 45 uL | 5 uL S1-0 | 1:200 |

Standards

Linearised transfer vectors plasmid (pG.AAV.CMV.GFP.P2A furin.fLuc.W6) served as reference standard. Initial standard aliquot D0 contains $1.30 \times 10^9$ plasmid copies per µl. Serial dilutions of ITR standard D0 were prepared as below.

Standard Dilution Curve for Quantification of AAV Genome Copy Numbers

| gc per µL | Dilution | Standard sample (µL) | DNAse-free water (µL) |
| --- | --- | --- | --- |
| D1 = $1.30 \times 10^8$ | 1:10 | 30 µL D0 | 270 µL |
| D2 = $1.30 \times 10^7$ | 1:10 | 100 µL D1 | 900 µL |
| D3 = $1.30 \times 10^6$ | 1:10 | 100 µL D2 | 900 µL |
| D4 = $1.30 \times 10^5$ | 1:10 | 100 µL D3 | 900 µL |
| D5 = $1.30 \times 10^4$ | 1:10 | 100 µL D4 | 900 µL |
| D6 = $1.30 \times 10^3$ | 1:10 | 100 µL D5 | 900 µL |
| D7 = $1.30 \times 10^2$ | 1:10 | 100 µL D6 | 900 µL |

Genomic titres were calculated according to the equation below.

$$AAV \text{ genome}/uL = \frac{2 \times gc \text{ per well} \times \text{dilution factor} \times \text{elution volume}}{\text{Lysate volume } ul}$$

A correction factor of 2 has to be applied since the plasmid DNA is double stranded while the AAV genomes are single stranded.

ITR qPCR Mastermix was prepared according to the formulation below.

Preparation of ITR qPCR Mastermix

| Reagents | Final concentration | Volume per well (μL) | Volume for 96 wells (μL) |
|---|---|---|---|
| ITR.P (10 μM) | 0.2 | 0.8 | 76.8 |
| ITR2.P (10 μM) | 0.2 | 0.4 | 38.4 |
| ITR2.R (10 μM) | 0.68 | 1.36 | 130.56 |
| TaqMan Fast Advanced Master Mix (2x) | 1x | 10 | 960 |
| Template | Variable | — | — |
| Total volume/well | 1x | | 12 |

12 μl of the Mastermix were added per well and 8 μl of each the sample dilutions Sx-0 to −1 were added. Additionally, 8 μl of the standard curve D1 to D7 were added to the plate. Standard curve was analysed in duplicates.

The final PCR plates were analysed using StepOnePlus real-time PCR machine. Cycling conditions are described below.

ITR qPCR Cycling Conditions

| Stage | Duration (sec) |
|---|---|
| Denaturation (1 cycle) | |
| 95° C. | 20 s |
| Amplification (40 cycles) | |
| 95° C. | 1 s |
| 60° C. | 20 s |

Figure 8:
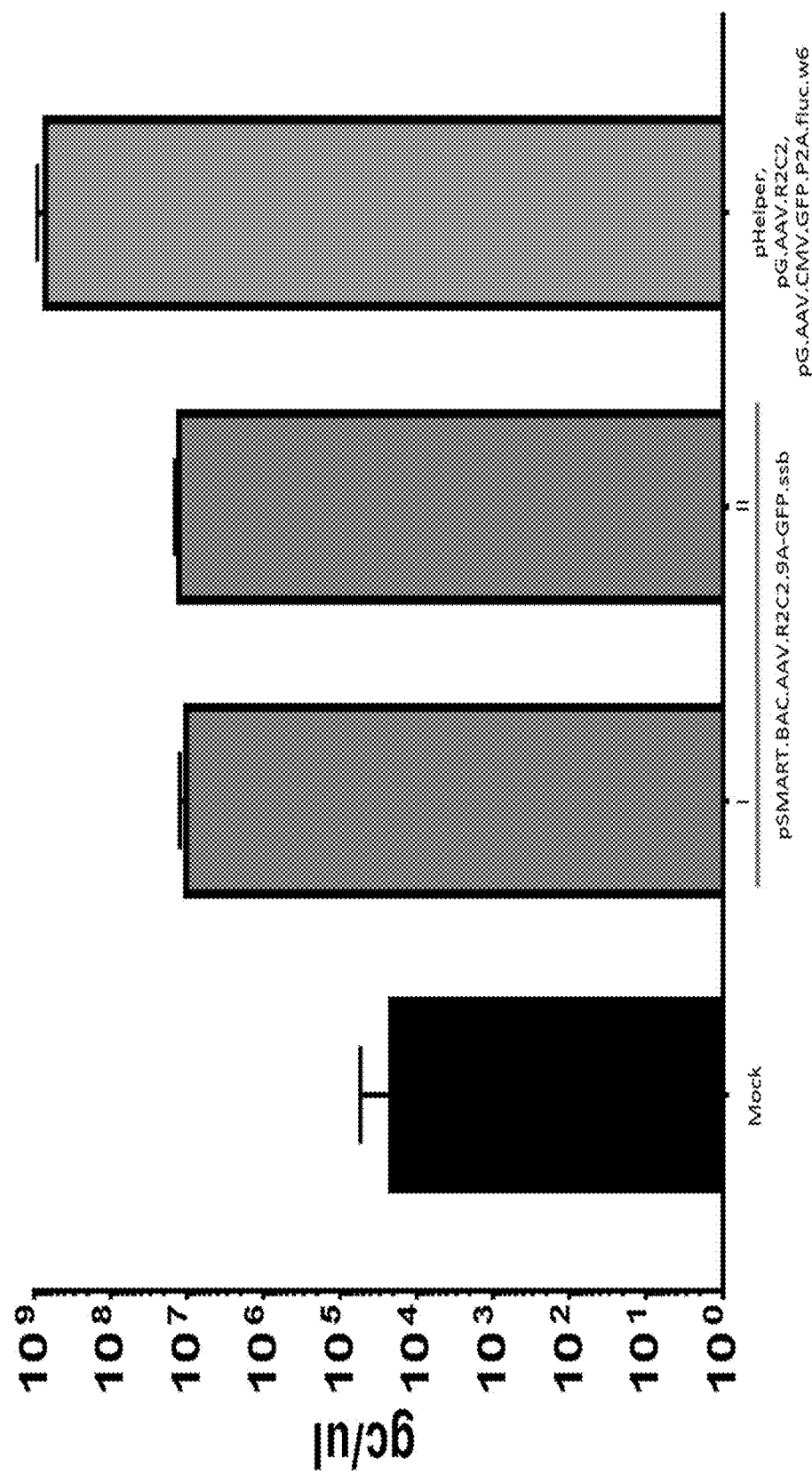
FIG. 8: Analysis of produced vector by qPCR on DNA extracted from lysed AdVec RS-D01 cells transfected with either BAC9A-GFP or the triple plasmid system control

FIG. 8 shows analysis of produced vector by qPCR on DNA extracted from lysed AdVec RS-D01 cells transfected with either BAC9A-GFP (pSMART.BAC.AAV.R2C2.9A-GFP.ssb) or the triple plasmid system control using pG.AAV.CMV.GFP.P2A.fluc.W6 as the transfer vector. Transfected cells were harvested, lysed and Benzonase™ treated. DNA was extracted and used for qPCR using ITR primers.

3.4.3 Transduction of LentiX 293T Cells with rAAV Lysate

LentiX 293T cells were maintained in LentiX media at 37° C., 5% $CO_2$ and split every 3-4 days.

24 h prior to transduction, cells were seeded at 8000 cells/well into a 96 well black flat-bottomed plate in LentiX media and incubated overnight.

On the day of transduction, 10 μl rAAV lysate was diluted in 90 μl LentiX media in 96 well flat-bottomed plate. Control lysate—rAAV2 at $1.5 \times 10^{13}$ vg/ml was diluted 1:10 (−1) then again (−2) and again (−3).

Seeding media on cells was removed and diluted lysate added to the cells and incubated 72 h at 37° C., 5% $CO_2$. 72 h post transduction cells were imaged for GFP expression using InStudio software and Olympia microscope. Transduction media was removed and 100 D-PBS with 0.5% EDTA was added per well and used to wash cells from well. 100 μl 4% PFA was added per well and cells analysed for GFP expression using MACS Quant 10 and FlowJo software.

FIG. 9(A) shows microscope images of transduced LentiX 293T cells, 72 h post-transduction. FIG. 9(B) shows analysis of GFP positive cells by MACS Quant analyser and FlowJo Software after transduction.

Figure 9:
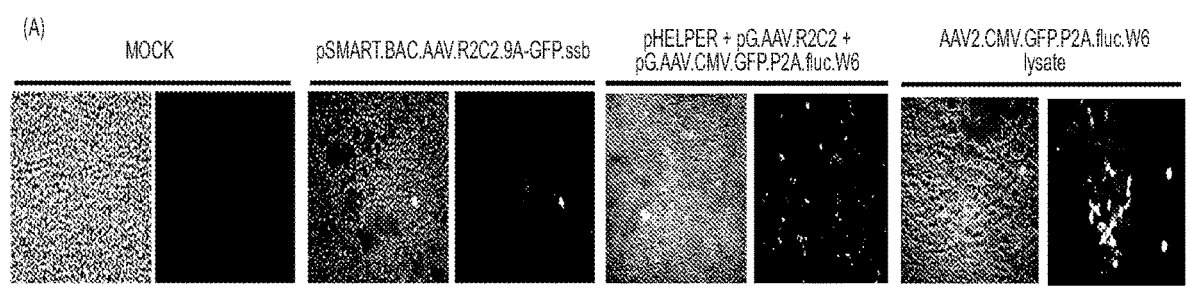
FIG. 9: Microscope images of transduced LentiX 293T cells, 72 h post-transduction and analysis of GFP positive cells.
Figure 9:
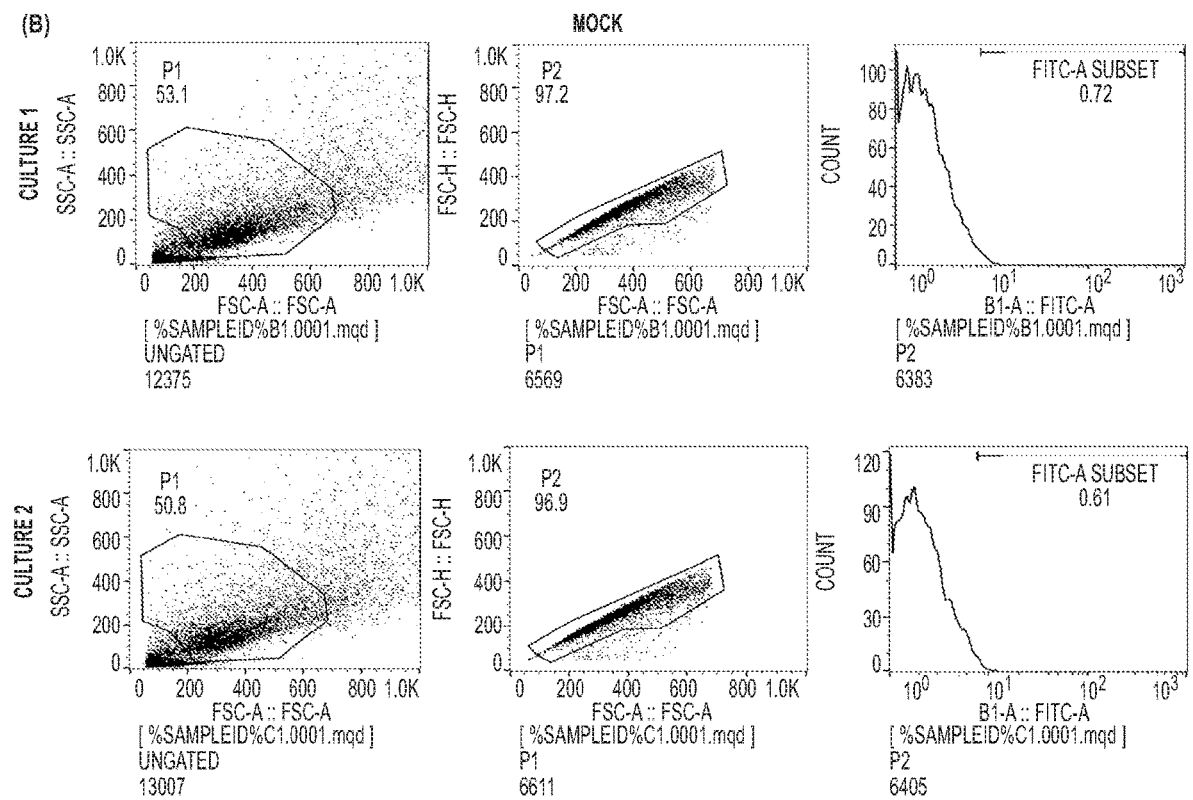
Figure 9:
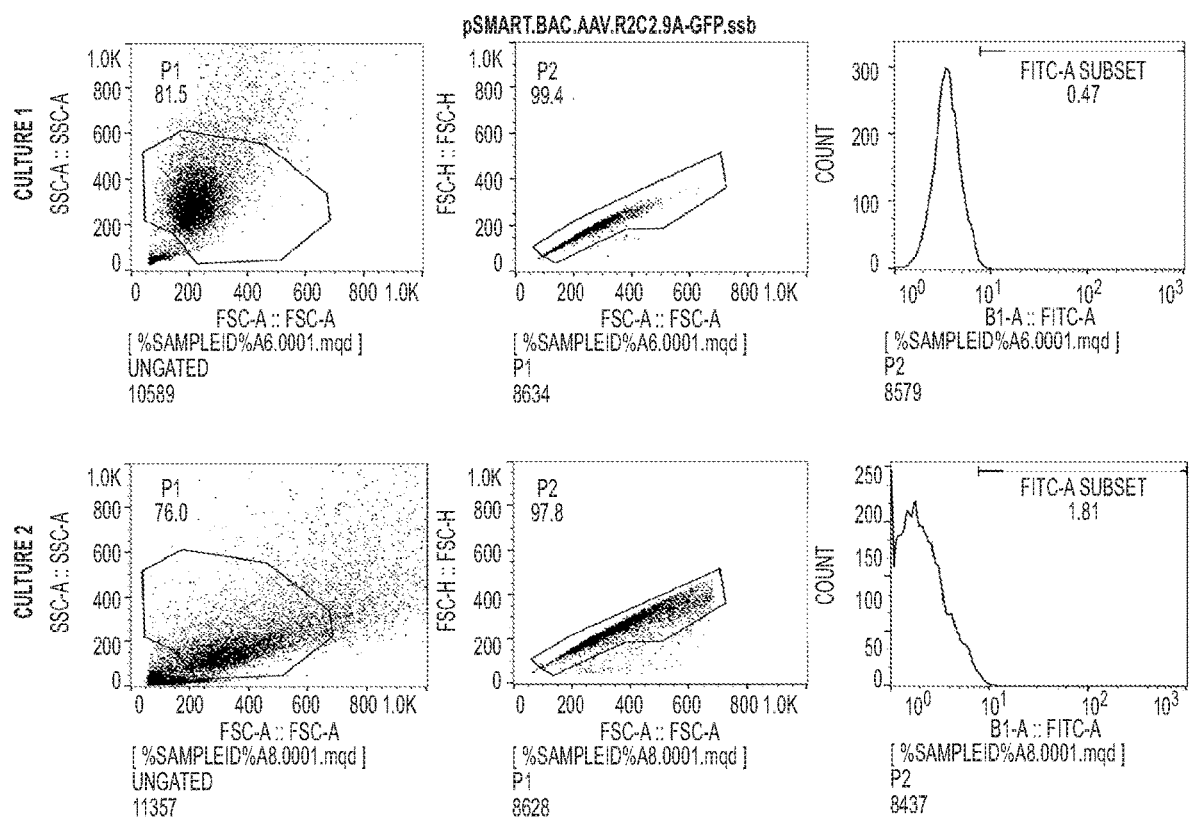
Figure 9:
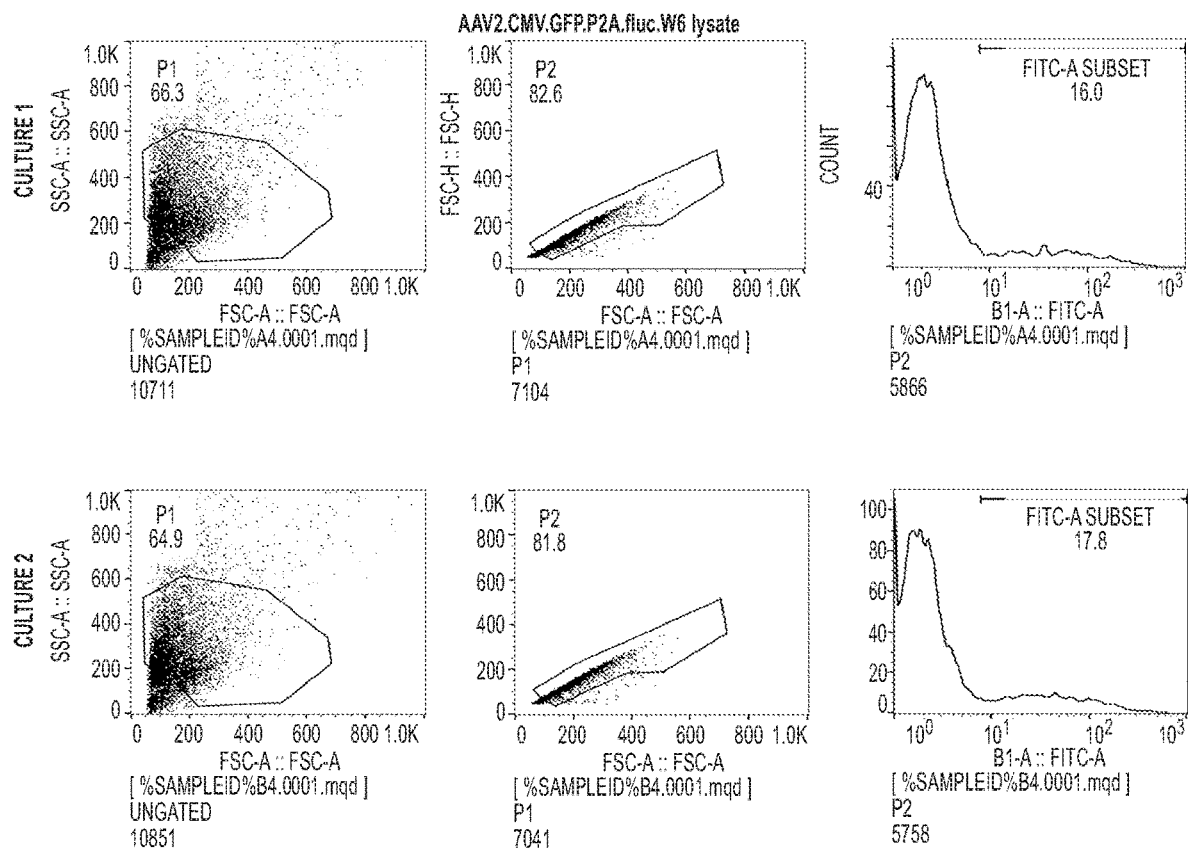

Lysates from transfected AdVec RS-D01 suspension cells were applied to LentiX 293T cells. AdVec RS-D01 cells transfected with either BAC9A-GFP (pSMART.BAC.AAV.R2C2.9A-GFP.ssb) or triple plasmid system control using pG.AAV.CMV.GFP.P2A.fluc.W6. Transfected cells were harvested, lysed and Benzonase™ treated.

qPCR of transfected cell lysate shows that vector has been produced with transient transfection using BAC9A-GFP and triple plasmid system transfection (FIG. 8). When these lysates were used to transduce LentiX 293T cells, after 72 h GFP positive cells were seen for both systems (FIG. 9). The number of GFP positive cells analysed by flow cytometry is lower than seen with AAV2.CMV.GFP.P2A.fluc.W6 control lysate but is encouraging and shows that the vector produced from the BAC9A-GFP is functional.

3.5 Selection of Cells with Stably Integrated pSMART.BAC.AAV Plasmid Using Zeocin 3.5.1 High Dose Selection 72 h post-transfection, AdVec RS-D01 cell cultures were centrifuged at 500 rpm for 10 min at 4° C., media removed and cell pellet resuspended in suspension cell media with 500 μg/ml Zeocin. Cultures were incubated at high dose selection for 6 days, changing the selection media every 2 days.

When media was changed, cell count and viability was assessed using method above and cells assessed for GFP expression by imaging and/or flow cytometry as described above (3.2.2).

3.5.2 Low Dose Selection

After 6 days at higher dose of Zeocin, media was changed to suspension cell media with 300 μg/ml Zeocin and media was changed every 2 days. From this point, cultures were continually maintained in 300 μg/ml Zeocin containing media.

Figure 10:
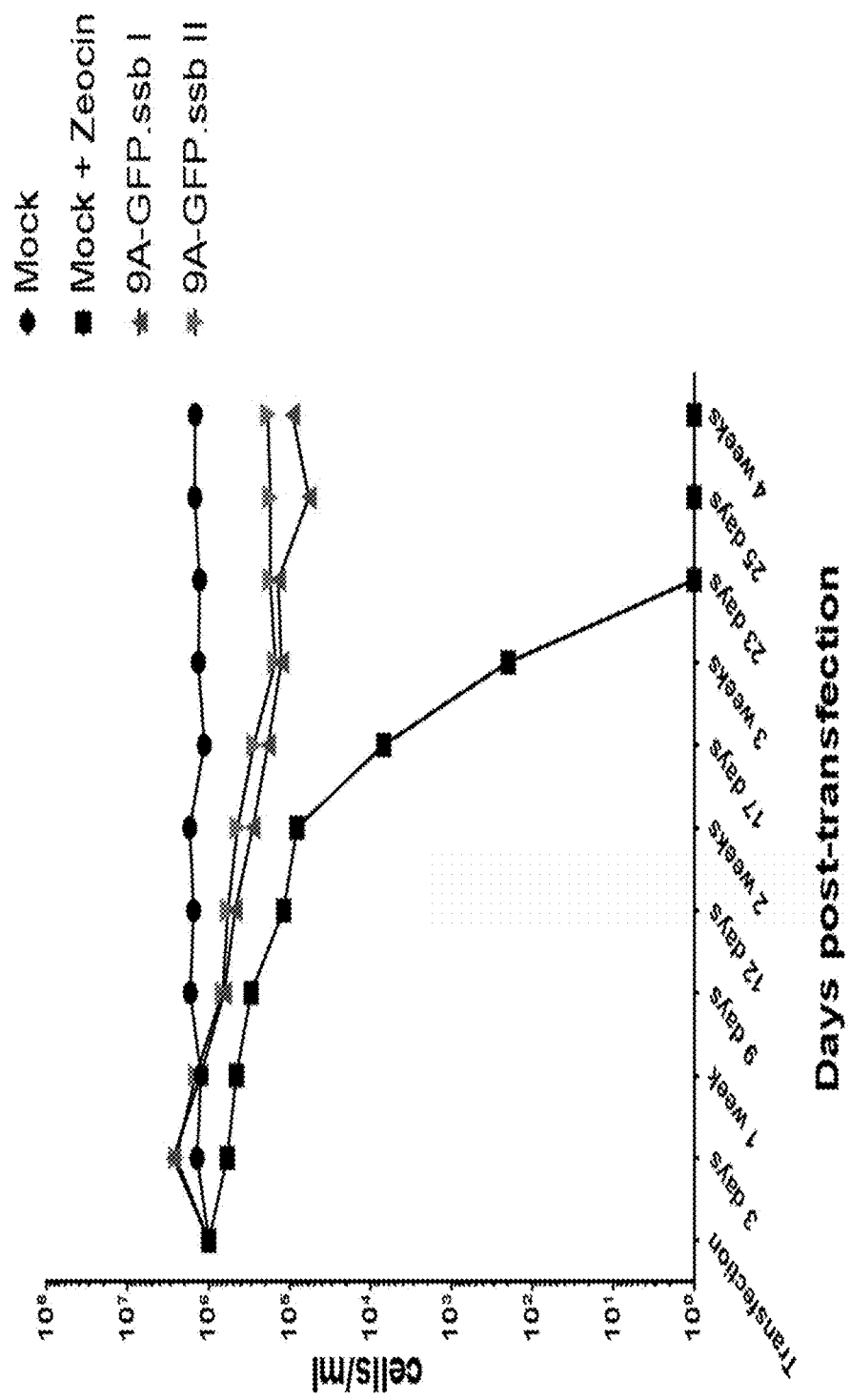
FIG. 10: Analysis of cell number/ml after transfection of BAC9A-GFP.

FIG. 10 is an analysis of cell number/ml after transfection of BAC9A-GFP. Analysis of transfected cultures under selection using the ViCell Xr to determine the number of viable cells at each timepoint shows that selection using Zeocin is working. Mock cells under Zeocin selection reduce in number and have completely died after 3 weeks while mock under no selection are still viable. The BAC9A-GFP (SMART.BAC.AAV.R2C2.9A-GFP.ssb) cell cultures gradually reduce in number but after 3 weeks maintain a stable population showing that within these cells the BAC9A-GFP has integrated.

Figure 11:
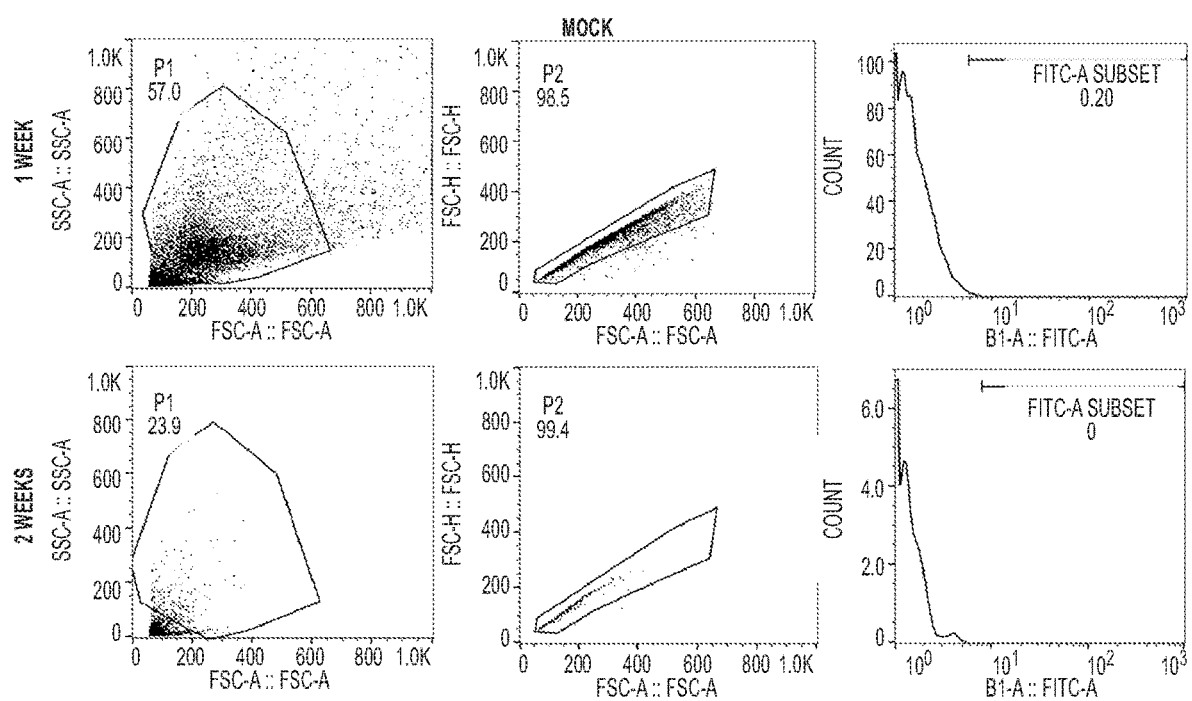
FIG. 11: Analysis of GFP positive cells by flow cytometry for AdVec RS-D01 suspension cells under Zeocin selection after transfection with BAC9A-GFP.
Figure 11:
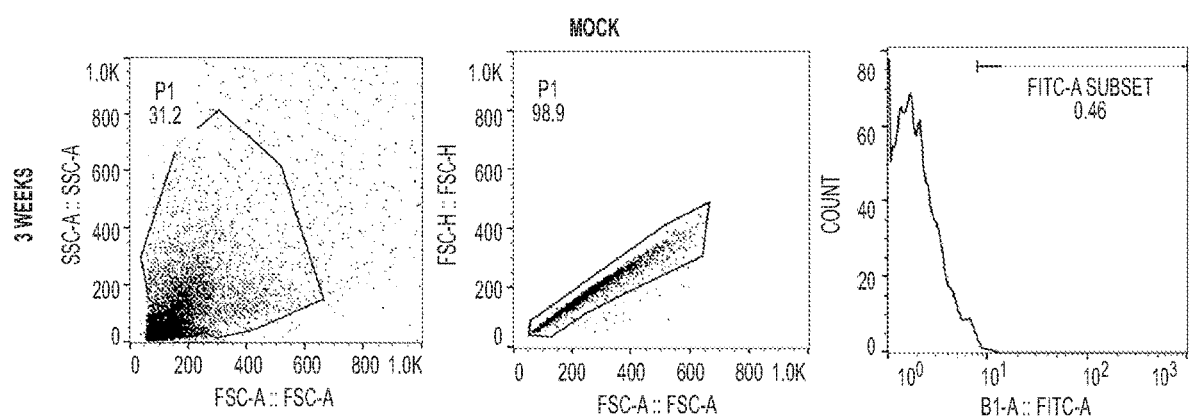
Figure 11:
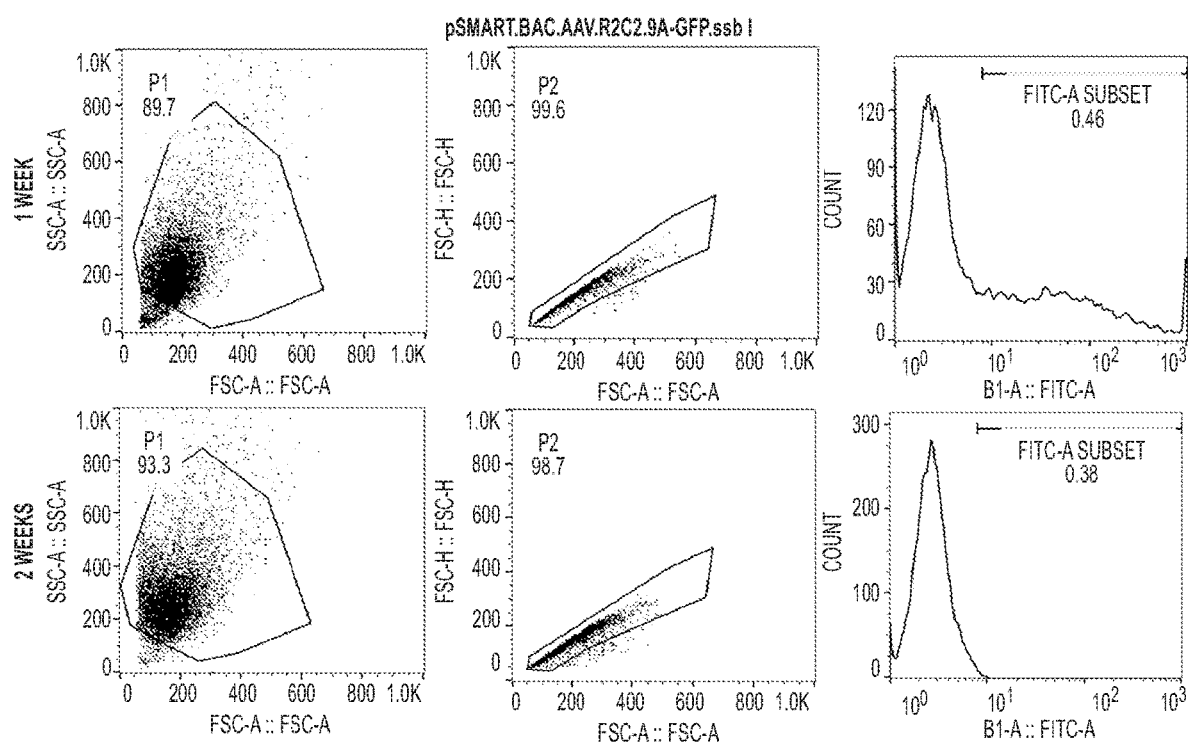
Figure 11:
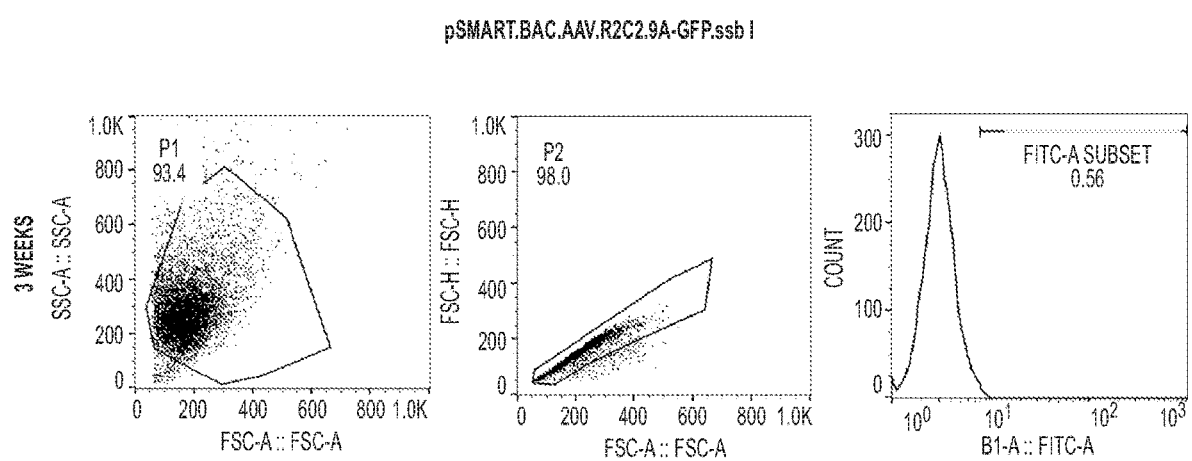
Figure 11:
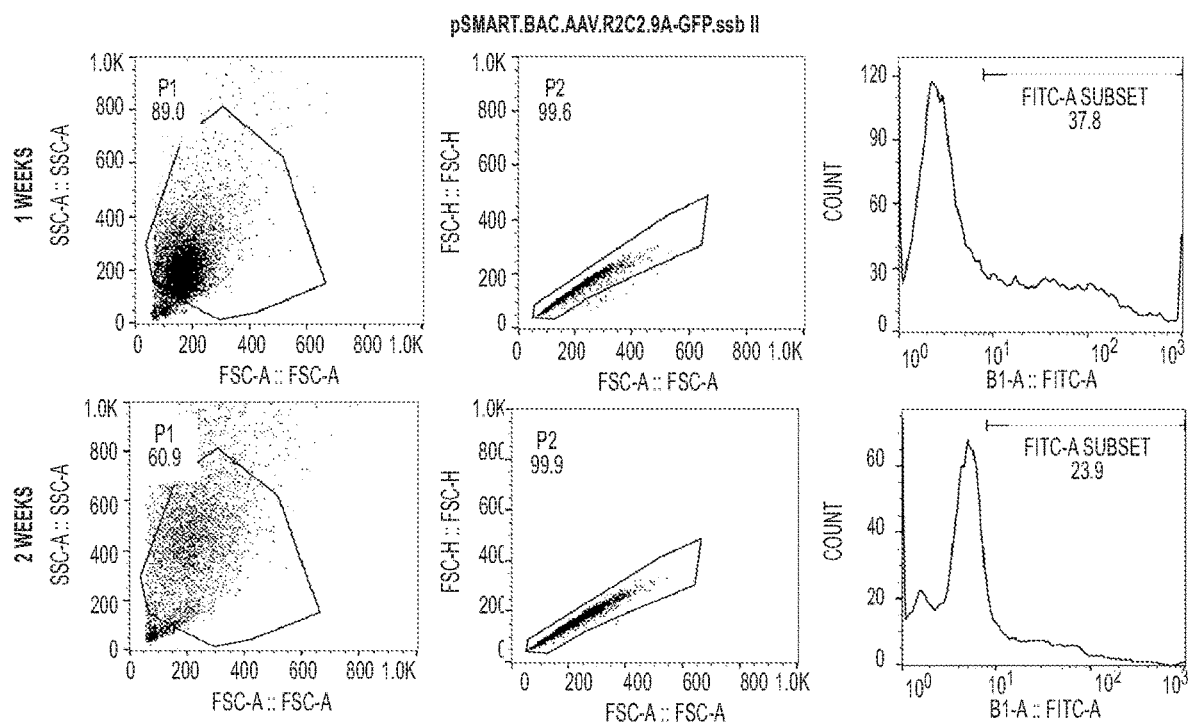
Figure 11:
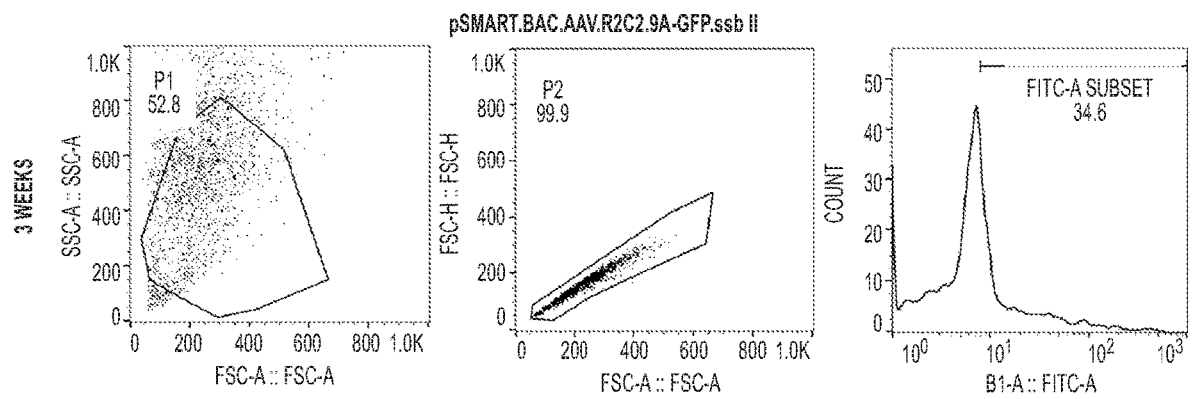

FIG. 11 is an analysis of GFP positive cells by flow cytometry for AdVec RS-D01 suspension cells under Zeocin selection after transfection with pSMART.BAC.AAV.R2C2.9A-GFP.ssb. Cells were analysed at weekly timepoints.

Figure 12:
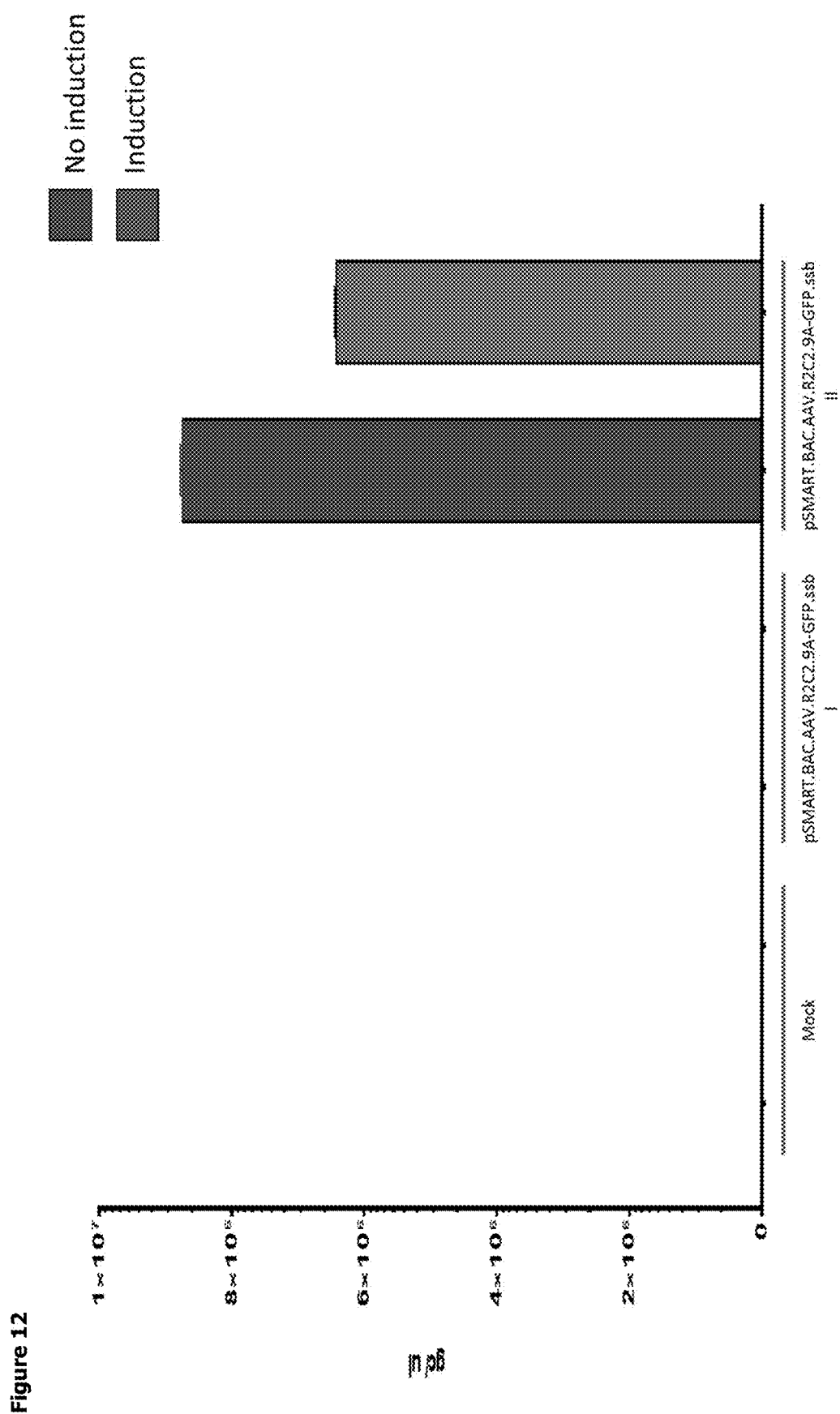
FIG. 12: qPCR analysis of vector produced from polyclonal Zeocin selected pools.

Analysis in FIG. 11 of the transfected cell pools weekly by flow cytometry shows that after 1 week in high concentration Zeocin, both cultures have over 35% of cells which are GFP positive. After 2 weeks, culture 1 has lost most of the GFP positive cells suggesting that while the BAC had been transfected in, it had not integrated in a high proportion of cells whilst in culture 2, the BAC had integrated in and the percentage of GFP positive cells increased from week 2 to week three as the population remaining after selection begins to reflect the integrated cell line. Selection is still ongoing with culture 2. The loss of the GFP positive cells from culture 1, may explain the lack of vector that was seen with this culture (FIG. 12).

3.5.3 Induction of rAAV from Polyclonal Population of Selected Cells Using Doxycycline 1 ml cell line culture was added to 2 wells of 24 deep-well suspension culture plate.

In one well, 1 ml BalanCD media was added (uninduced). In the other, 1 ml BalanCD media with 4 µg/ml Doxycycline (2 µg/ml final concentration, Induced). Cells were incubated at 37° C., 5% $CO_2$, 140 rpm for 48 h.

48 h post-induction, cells were harvested by centrifugation at 2000×g for 5 min. Supernatant was removed and cells lysed in AAV lysis buffer (50 mM Tris, 150 mM NaCl, 2 mM $MgCl_2$) 50 µl per ml of cells, at room temperature for 5 min, vortexed then frozen at −80° C. Cell lysis underwent three rounds of freeze, thaw at −80° C. and 37° C. The lysate was treated with Benzonase™ (50 U/ml) at 37° C. for 30 min then clarified by centrifugation at 4000×g for 20 min. Lysate was removed to a fresh pre-chilled tube and aliquoted—2×5 µl for DNA extraction for qPCR analysis, 4×10 µl for transductions.

FIG. 12 shows a qPCR analysis of vector produced from polyclonal selected pools. AdVec RS-D01 cells transfected with BAC9A-GFP were selected for stably transfected cells using Zeocin for 1 month. These cells were induced with 2 µg/ml Doxycycline for 48 h. Cells were harvested, lysed and Benzonase™ treated. DNA was extracted and used for qPCR using ITR primers using the same protocol as 3.4.

Analysis of vector production from stable pool cultures shows that viral vector particle is still being made in one of the pools (culture 2) but not in culture 1. This shows that the BAC9A-GFP (SMART.BAC.AAV.R2C2.9A-GFP.ssb) system is functioning and can be used to produce stable cell lines which produce AAV vector.

Whilst the addition of Doxycycline to the growth media does not seem to have increased the titre of the vectors produced from the BAC9A-GFP cell lines, the induction was only for 48 h which may be too short a time to see an effect from the decrease in shRNA production and increase in Rep expression. Alternatively, the system may be leaky and Rep is being produced even in the absence of the Rep shRNA being suppressed by Doxycycline.

Figure 13:
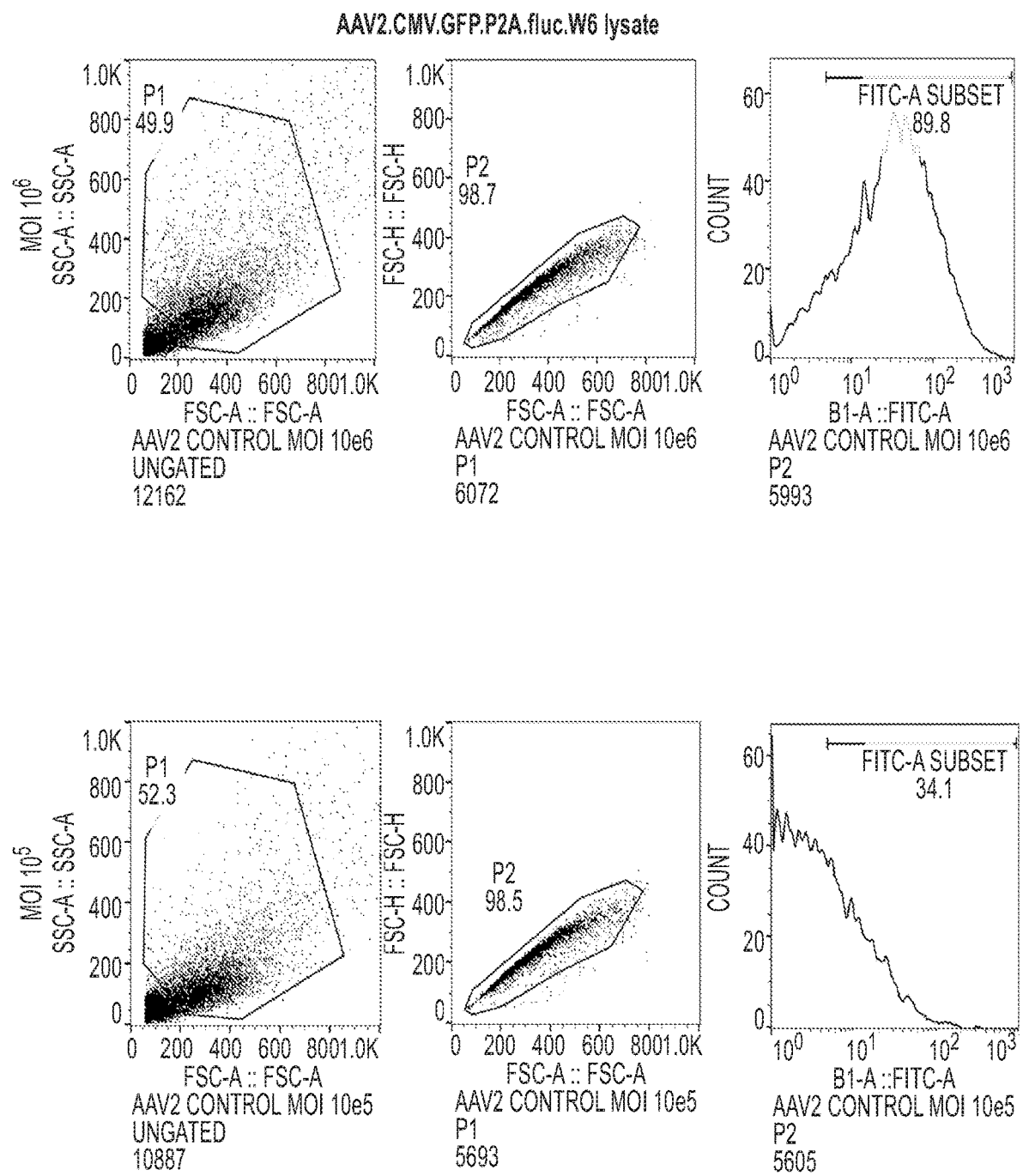
FIG. 13: Flow cytometry analysis of GFP positive cells of LentiX293T cells transfected with BAC9A-GFP and Zeocin selected.
Figure 13:
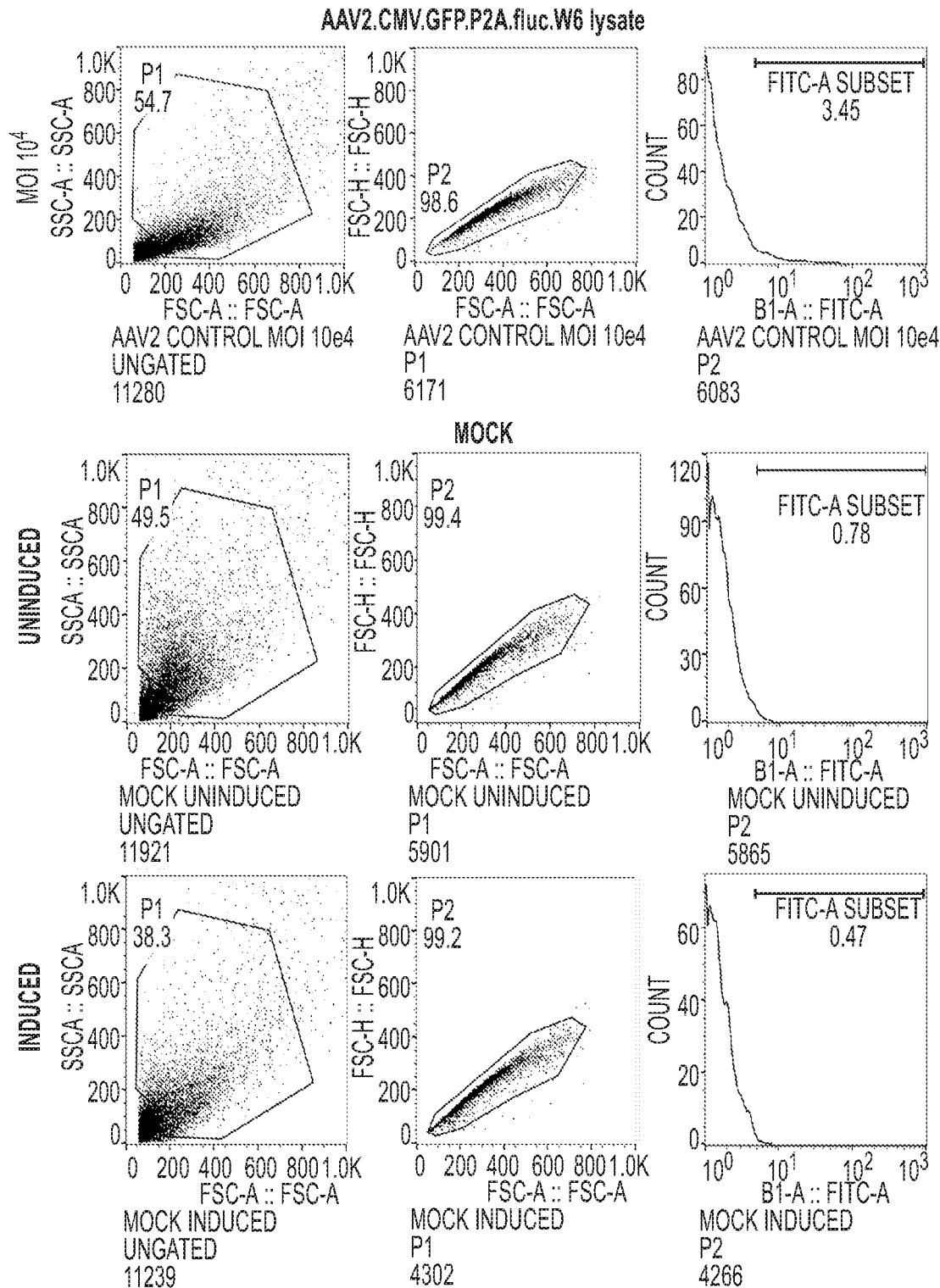
Figure 13:
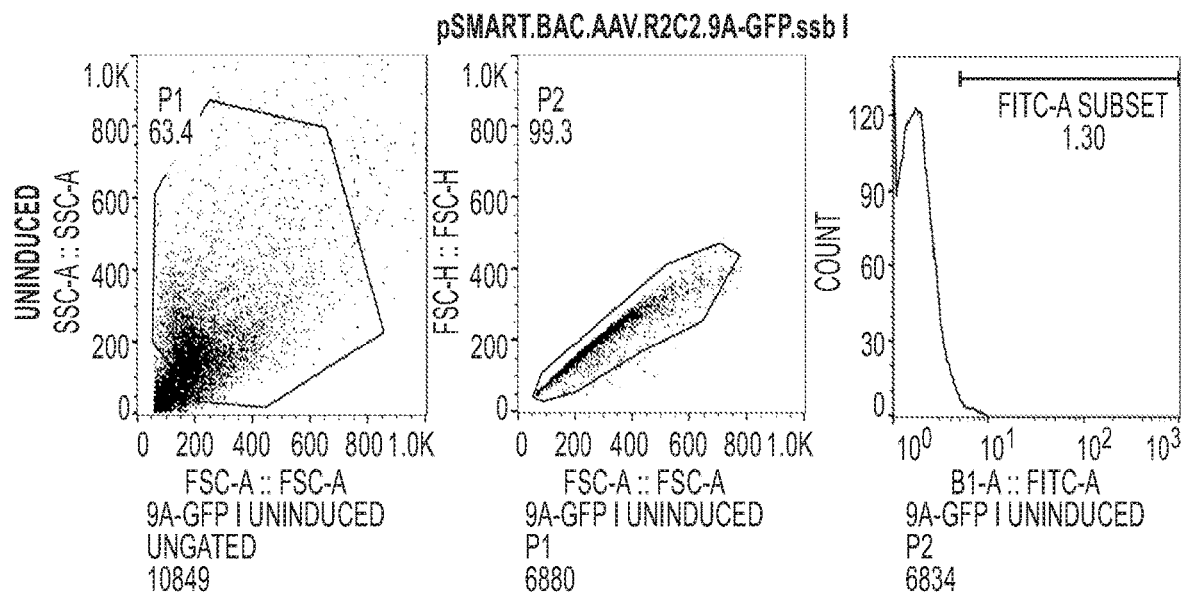
Figure 13:
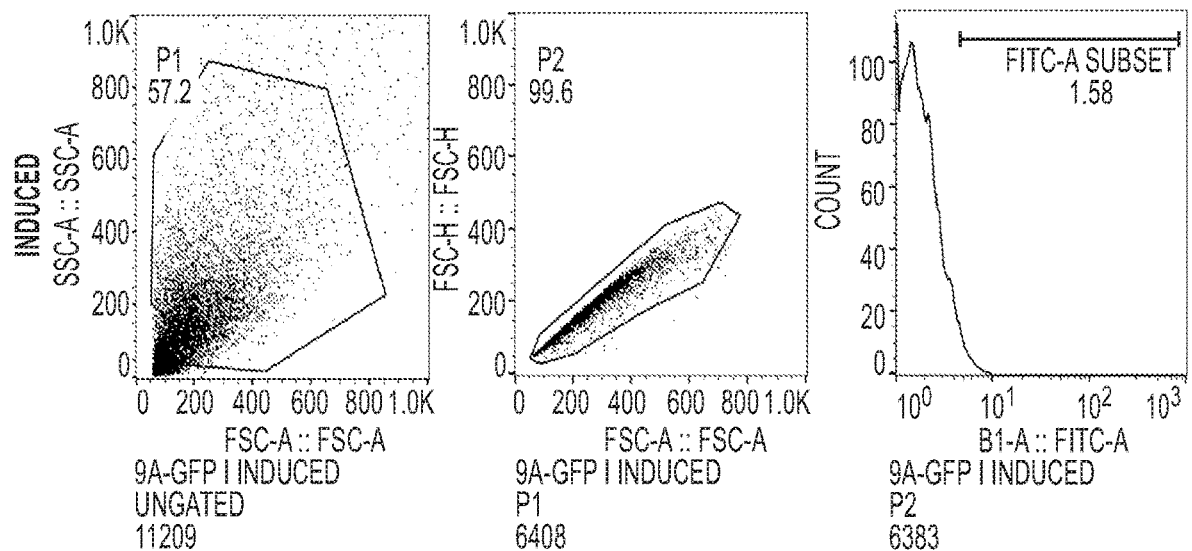
Figure 13:
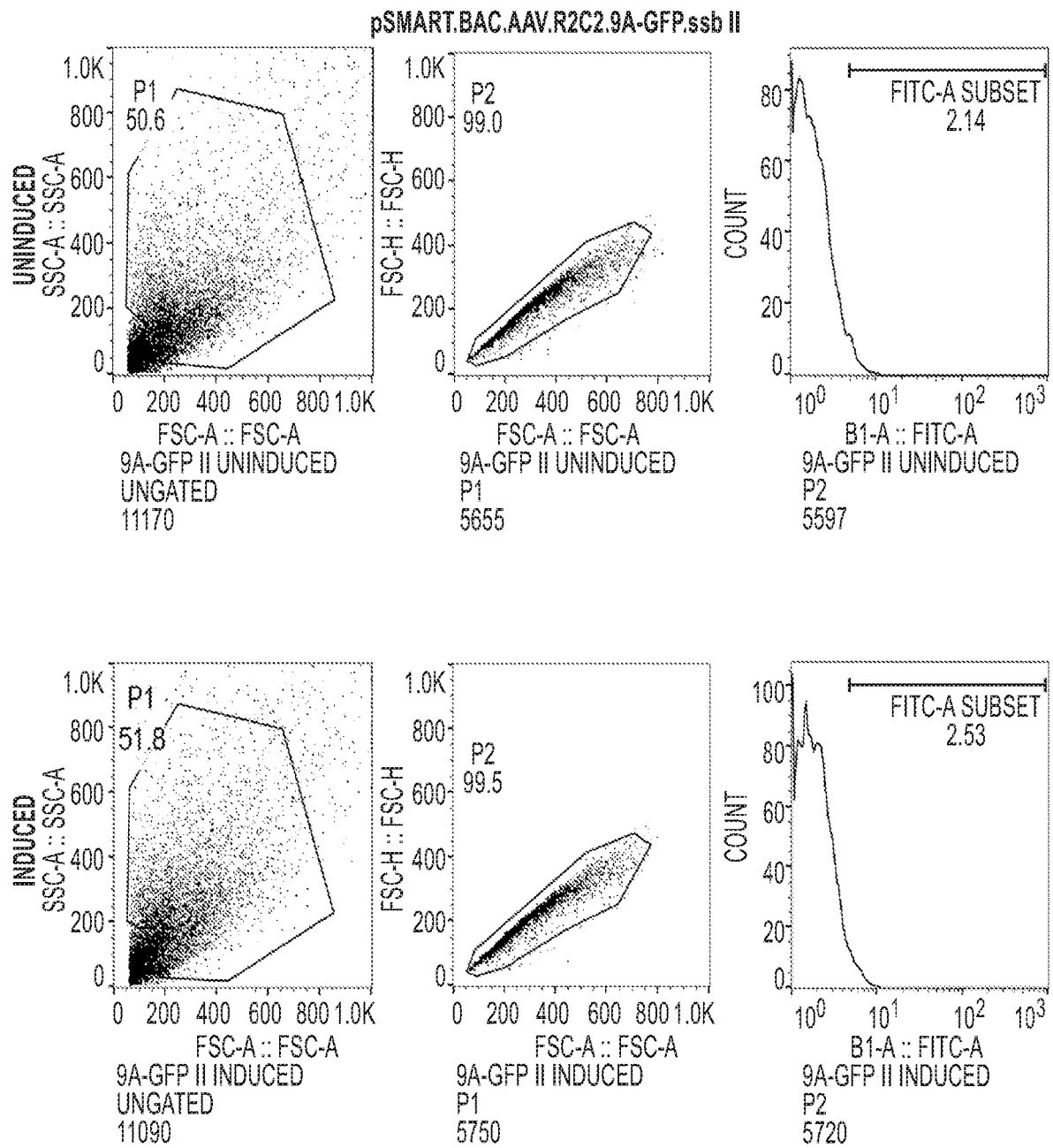

FIG. 13 shows transduction of LentiX 293T cells with lysate from AdVec RS-D01 cells under selection for 1 month. AdVec RS-D01 cells were transfected with BAC9A-GFP then selected using Zeocin for 1 month. These cell pools were then induced using 2 µg/ml Doxycycline for 48 h. Cells were harvested, lysed and Benzonase™ treated. Lysate was applied to LentiX 293T cells and assessed 72 h post-transduction for GFP positive cells by and flow cytometry.

Transduction of LentiX 293T cells with lysate from BAC9A-GFP pools shows that while the amount of vector produced may be low, it is biologically functional. The low genome copies per µl seen in the qPCR data is reflected in the percentage of GFP positive cells analysed by flow cytometry but it shows that some vector is being made even at this early stage.

Example 4: Generation of AAV Stable Producer Cell Line (Adherent Cells)

Stable cell lines were generated by transfecting adherent HEK293 cells with BAC8A-GFP and BAC9A-GFP constructs.

Figure 14:
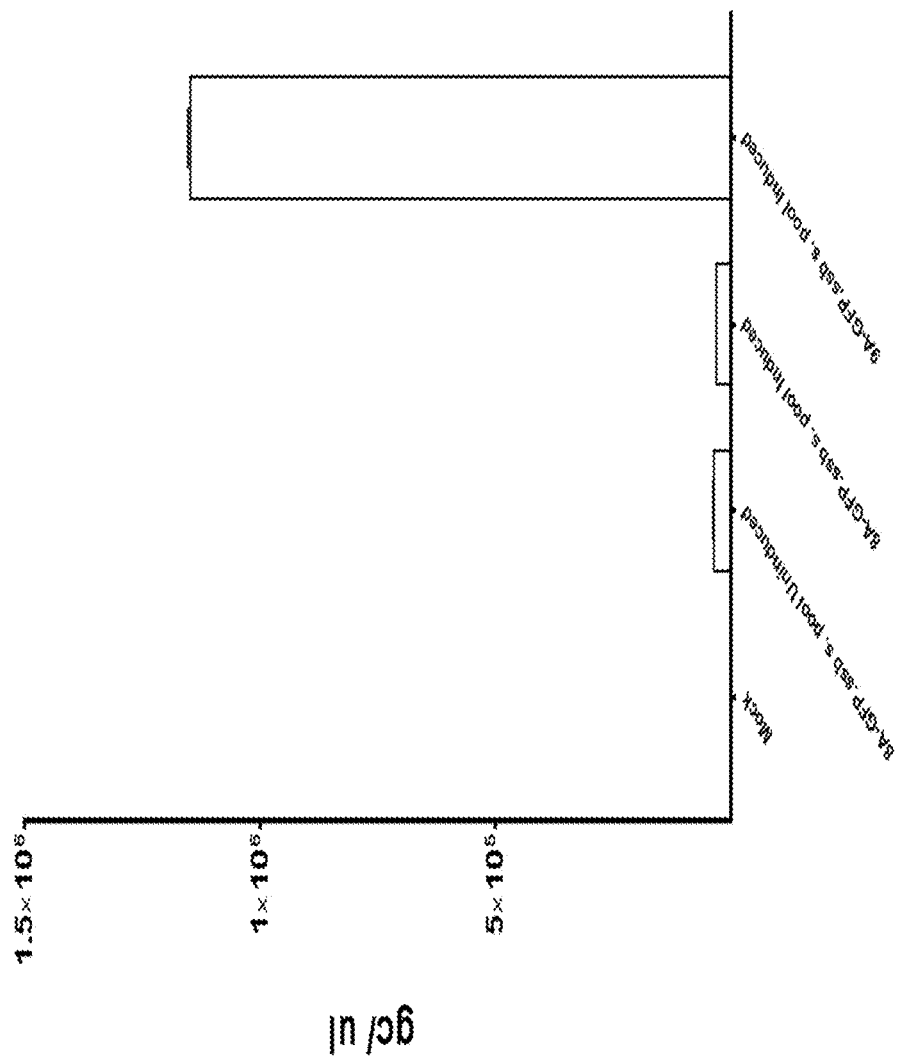
FIG. 14: qPCR analysis of vector production from adherent AdVec cell stable pools.

FIG. 14 shows a qPCR analysis of vector production from adherent AdVec cell stable pools. Cells were transfected with either BAC8A-GFP (pSMART.BAC.AAV.R2C2.8A-GFP.ssb) or BAC9A-GFP (pSMART.BAC.AAV.R2C2.9A-GFP.ssb). The BAC8A-GFP and BAC9A-GFP transfected cells were put under Zeocin selection for 2 and 4 weeks, respectively.

This shows that both the BAC8A-GFP and BAC9A-GFP systems are functioning and can be used to produce stable cell lines which produce AAV vector particles.

Reagents and Chemicals

| Product Name | Supplier | Catalogue No. |
|---|---|---|
| AAV2 ELISA | Progen | PRATV |
| Endofree distilled water (cell culture grade) | Sigma | W3500 |
| BalanCD | IrvinScientific | 91165 |
| DMEM (1x) | Gibco | 41966-029 |
| 10% Pluronic F-68 | Gibco | 24040-032 |
| GlutaMAX-I (x100) | Gibco | 35050-038 |
| FCS | Gibco | |
| MEM NEAA | Gibco | 11140-035 |
| Penicillin Streptomycin | Gibco | 15140-122 |
| Trypsin | Gibco | 25300-054 |
| 1 mg/ml Zeocin | Invitrogen | 10072492 |
| Doxycycline hyclate | Sigma | D9891 |
| PEIpro | Polyplus | 115-010 |
| Benzonase ™ | Sigma | 9025-65-4 |
| High Pure Viral Nucleic Acid Kit | Roche | 11858874001 |
| Nuclease-Free Water (not DEPC-Treated) | ThermoFisher Scientific | AM9930 |
| OptiMEM | ThermoFisher Scientific | 31985070 |
| TaqMan Fast Advanced Master Mix | ThermoFisher Scientific | 4444556 |
| 4% PFA in PBS, with Mg and EGTA | Alfa Aesar | 15454859 |

Media and Solutions

| Name | Components |
|---|---|
| Suspension cell media | 1L BalanCD, 2% GlutaMAX, 1% Pluronic F-68 |
| LentiX media | 1 x DMEM, 10% HI FCS, 1% MEM NEAA, 1% Pen, Strep |
| AAV lysis buffer | 50 mM Tris, 150 mM NaCl, 2 mM $MgCl_2$, pH 8.5 |

Instruments and Software

| Name | Manufacturer |
|---|---|
| StepOne Software v2.3 | Applied Biosystems |
| Vi-Cell ™ XR - Cell Viability Analyser | ViCell |
| StepOnePlus | Applied Biosystems |
| MACS Quant 10 | Miltenyi |
| Olympia Microscope InStudio software | |
| FlowLogic 700.1A | Invai Technologies Pty. Ltd. |
| FlowJo 10.2 | FlowJo |

It will be understood that the embodiments described herein may be applied to all aspects of the invention. Furthermore, all publications, including but not limited to patents and patent applications, cited in this specification are herein incorporated by reference as though fully set forth.

The invention claimed is:

1. An isolated adeno-associated virus (AAV) producer cell comprising nucleic acid sequences encoding:
   AAV rep/cap gene;
   helper virus genes; and
   a DNA genome of an AAV vector particle,
wherein said nucleic acid sequences are all integrated together at a single locus within the AAV producer cell genome; and wherein the cell further comprises a nucleic acid sequence encoding a short hairpin RNA (shRNA) targeting an AAV rep mRNA molecule encoded by the AAV rep gene and an inducible promoter operably linked to the nucleic acid sequence encoding the shRNA.

2. The AAV producer cell of claim 1, wherein the AAV nucleic acid sequences are derived from AAV1, AAV2, AAV3, AAV4, AAV5, AAV6, AAV7, AAV8, AAV9, AAV10, AAV11, AAV12, AAV13 or combinations thereof.

3. The AAV producer cell of claim 2, wherein the AAV nucleic acid sequences are derived from AAV2, AAV5 and/or AAV9.

4. The AAV producer cell of claim 1, wherein the helper virus genes are derived from adenovirus.

5. The AAV producer cell of claim 4, wherein the helper virus genes comprise all or part of E4, E2a and VA genes derived from adenovirus.

6. The AAV producer cell of claim 1, which additionally comprises a transcription regulation element.

7. The AAV producer cell of claim 6, wherein the transcription regulation element is a CMV promoter.

8. The AAV producer cell of claim 6, wherein the transcription regulation element additionally comprises at least one Tet operon.

9. The AAV producer cell of claim 1, which additionally comprises a tetracycline resistance operon repressor protein (TetR).

10. The AAV producer cell of claim 1, which additionally comprises an insulator.

11. The AAV producer cell of claim 10, wherein an insulator is present between each of the nucleic acid sequences.

12. The AAV producer cell of claim 1, which additionally comprises a selectable marker.

13. The AAV producer cell of claim 12, wherein the selectable marker is an amplifiable selection marker.

14. The AAV producer cell of claim 1, which additionally comprises one or more transgenes.

15. The AAV producer cell of claim 1, wherein the DNA genome of the AAV vector particle comprises one or more transgenes encoded between two AAV ITRs.

16. The AAV producer cell of claim 1, wherein the cell is a mammalian cell.

17. The AAV producer cell of claim 1, wherein the cell further comprises nucleic acid sequences encoding:
   an adenovirus E1A gene;
   an shRNA targeting an adenovirus E1A mRNA molecule encoded by the adenovirus E1A gene; and
   an inducible promoter operably linked to the nucleic acid sequence encoding the shRNA targeting the adenovirus E1A mRNA molecule.

18. The AAV producer cell of claim 1, wherein the cell further comprises a nucleic acid sequence of the shRNA targeting the AAV rep mRNA molecule or an E1A mRNA molecule, wherein the nucleic acid sequence is micro-RNA adapted for transcription by RNA polymerase II.

19. The AAV producer cell of claim 1, wherein the inducible promoter is a Tet-responsive promoter, optionally wherein the Tet-responsive promoter is a Ptet-T6 promoter.

20. A nucleic acid vector comprising a non-mammalian origin of replication and the ability to hold at least 25 kilobases (kb) of DNA, characterized in that said nucleic acid vector comprises nucleic acid sequences encoding:
   Adeno-associated virus (AAV) rep/cap gene, and
   helper virus genes,
wherein the nucleic acid sequences encoding the AAV rep/cap gene and each of the helper virus genes are arranged as individual expression cassettes within the nucleic acid vector; and wherein the nucleic acid vector further comprises a nucleic acid sequence encoding a short hairpin RNA (shRNA) targeting an AAV rep mRNA molecule encoded by the AAV rep gene and an inducible promoter operably linked to the nucleic acid sequence encoding the shRNA.

21. The nucleic acid vector of claim 20, which additionally comprises a nucleic acid sequence which encodes the DNA genome of the AAV vector particle.

22. The nucleic acid vector of claim 20, wherein the vector is selected from: a bacterial artificial chromosome, a yeast artificial chromosome, a P1-derived artificial chromosome, a fosmid or a cosmid.

23. The nucleic acid vector of claim 22, wherein the vector is a bacterial artificial chromosome.

24. The nucleic acid vector of claim 20, wherein the nucleic acid vector further comprises nucleic acid sequences encoding:
   an adenovirus E1A gene;
   an shRNA targeting an adenovirus E1A mRNA molecule encoded by the adenovirus E1A gene; and
   an inducible promoter operably linked to the nucleic acid sequence encoding the shRNA targeting the adenovirus E1A mRNA molecule.

25. The nucleic acid vector of claim 20, wherein the nucleic acid vector further comprises a nucleic acid sequence of the shRNA targeting the AAV rep mRNA molecule or the E1A mRNA molecule, wherein the nucleic acid sequence is micro-RNA adapted for transcription by RNA polymerase II.

26. The nucleic acid vector of claim 20, wherein the inducible promoter is a Tet-responsive promoter, optionally wherein the Tet-responsive promoter is a Ptet-T6 promoter.

27. A method of producing a stable AAV packaging cell line, comprising:
   (a) introducing the nucleic acid vector of claim 20 into a culture of mammalian host cells; and
   (b) selecting within the culture for a mammalian host cell which has the nucleic acid sequences encoded on the vector integrated into an endogenous chromosome of the mammalian host cell.

28. The method of claim 27, wherein the mammalian cell is a HEK 293 cell.

29. An isolated AAV packaging cell obtained by the method of claim 27.

30. A method of producing a replication defective AAV vector particle, comprising:
  (a) introducing the nucleic acid vector of claim 20 into a culture of mammalian host cells;
  (b) selecting within the culture for a mammalian host cell which has the nucleic acid sequences encoded on the vector integrated into an endogenous chromosome of the mammalian host cell; and
  (c) further culturing the selected mammalian host cell under conditions in which the replication defective AAV vector particle is produced.

31. The method of claim 30, additionally comprising isolating the replication defective AAV vector particle.

32. A replication defective AAV vector particle obtained by the method of claim 30.

* * * * *

SEQUENCE LISTING

<160> NUMBER OF SEQ ID NOS: 33

<210> SEQ ID NO 1
<211> LENGTH: 19
<212> TYPE: DNA
<213> ORGANISM: Artificial sequence
<220> FEATURE:
<223> OTHER INFORMATION: 5' primer with homology to Rep2

<400> SEQUENCE: 1
tggacgtttc ctgagtcag                                                    19

<210> SEQ ID NO 2
<211> LENGTH: 21
<212> TYPE: DNA
<213> ORGANISM: Artificial sequence
<220> FEATURE:
<223> OTHER INFORMATION: 3' primer with homology to Rep2

<400> SEQUENCE: 2
attcgcgaaa aactgattca g                                                 21

<210> SEQ ID NO 3
<211> LENGTH: 21
<212> TYPE: DNA
<213> ORGANISM: Artificial sequence
<220> FEATURE:
<223> OTHER INFORMATION: AAV cap2/5 shRNA

<400> SEQUENCE: 3
tgttgatgag tctttgccag t                                                 21

<210> SEQ ID NO 4
<211> LENGTH: 21
<212> TYPE: DNA
<213> ORGANISM: Artificial sequence
<220> FEATURE:
<223> OTHER INFORMATION: AAV rep2 shRNA 5

<400> SEQUENCE: 4
tctttcccgc attgtccaag g                                                 21

<210> SEQ ID NO 5
<211> LENGTH: 21
<212> TYPE: DNA
<213> ORGANISM: Artificial sequence
<220> FEATURE:
<223> OTHER INFORMATION: AAV rep2 shRNA 7

<400> SEQUENCE: 5
tttataaatc cgattgctgg a                                                 21

<210> SEQ ID NO 6
<211> LENGTH: 21
<212> TYPE: DNA
<213> ORGANISM: Artificial sequence
<220> FEATURE:
<223> OTHER INFORMATION: AAV rep2 shRNA 9

<400> SEQUENCE: 6
aaggtcgttg agttcccgtc a                                                 21

<210> SEQ ID NO 7
<211> LENGTH: 21
<212> TYPE: DNA
<213> ORGANISM: Artificial sequence
<220> FEATURE:
<223> OTHER INFORMATION: AAV rep2 shRNA 11

<400> SEQUENCE: 7
tttgacgtag aattcatgct c                                          21

<210> SEQ ID NO 8
<211> LENGTH: 21
<212> TYPE: DNA
<213> ORGANISM: Artificial sequence
<220> FEATURE:
<223> OTHER INFORMATION: AAV rep2 shRNA 13

<400> SEQUENCE: 8
tcaaatttga acatccggtc t                                          21

<210> SEQ ID NO 9
<211> LENGTH: 21
<212> TYPE: DNA
<213> ORGANISM: Artificial sequence
<220> FEATURE:
<223> OTHER INFORMATION: AAV rep2 shRNA 14

<400> SEQUENCE: 9
ttgaagggaa agttctcatt g                                          21

<210> SEQ ID NO 10
<211> LENGTH: 19
<212> TYPE: DNA
<213> ORGANISM: Artificial sequence
<220> FEATURE:
<223> OTHER INFORMATION: miR-30a loop sequence

<400> SEQUENCE: 10
tagtgaagcc acagatgta                                             19

<210> SEQ ID NO 11
<211> LENGTH: 27
<212> TYPE: DNA
<213> ORGANISM: Artificial sequence
<220> FEATURE:
<223> OTHER INFORMATION: upstream micro-RNA sequence

<400> SEQUENCE: 11
aaggtatatt gctgttgaca gtgagcg                                    27

<210> SEQ ID NO 12
<211> LENGTH: 18
<212> TYPE: DNA
<213> ORGANISM: Artificial sequence
<220> FEATURE:
<223> OTHER INFORMATION: downstream micro-RNA sequence

<400> SEQUENCE: 12
tgcctactgc ctcggact                                              18

<210> SEQ ID NO 13
<211> LENGTH: 21
<212> TYPE: DNA
<213> ORGANISM: Artificial sequence
<220> FEATURE:
<223> OTHER INFORMATION: E1A shRNA 1

<400> SEQUENCE: 13
tggcaggtaa gatcgatcac c                                          21

```
<210> SEQ ID NO 14
<211> LENGTH: 21
<212> TYPE: DNA
<213> ORGANISM: Artificial sequence
<220> FEATURE:
<223> OTHER INFORMATION: E1A shRNA 2

<400> SEQUENCE: 14
ttactgtaga caaacatgcc a                                                   21

<210> SEQ ID NO 15
<211> LENGTH: 21
<212> TYPE: DNA
<213> ORGANISM: Artificial sequence
<220> FEATURE:
<223> OTHER INFORMATION: E1A shRNA 3

<400> SEQUENCE: 15
tctaaatcat acagttcgtg a                                                   21

<210> SEQ ID NO 16
<211> LENGTH: 21
<212> TYPE: DNA
<213> ORGANISM: Artificial sequence
<220> FEATURE:
<223> OTHER INFORMATION: E1A shRNA 4

<400> SEQUENCE: 16
tccgtactac tattgcattc t                                                   21

<210> SEQ ID NO 17
<211> LENGTH: 21
<212> TYPE: DNA
<213> ORGANISM: Artificial sequence
<220> FEATURE:
<223> OTHER INFORMATION: E1A shRNA 5

<400> SEQUENCE: 17
tctaacacaa actcctcacc c                                                   21

<210> SEQ ID NO 18
<211> LENGTH: 40
<212> TYPE: DNA
<213> ORGANISM: Artificial sequence
<220> FEATURE:
<223> OTHER INFORMATION: 2xcHS4 donor I-SceI F

<400> SEQUENCE: 18
attaccctgt tatccctatt atacgaagtt atattacgcg                               40

<210> SEQ ID NO 19
<211> LENGTH: 52
<212> TYPE: DNA
<213> ORGANISM: Artificial sequence
<220> FEATURE:
<223> OTHER INFORMATION: 2xcHS4 donor PI-PspI R

<400> SEQUENCE: 19
acccataata cccataatag ctgtttgcca taactagtca ataatcaatg tc                 52

<210> SEQ ID NO 20
<211> LENGTH: 27
<212> TYPE: DNA
<213> ORGANISM: Artificial sequence
<220> FEATURE:
<223> OTHER INFORMATION: E4 MluI F
```

```
<400> SEQUENCE: 20
gtcgcacgcg ttttagggcg gagtaac                                      27

<210> SEQ ID NO 21
<211> LENGTH: 25
<212> TYPE: DNA
<213> ORGANISM: Artificial sequence
<220> FEATURE:
<223> OTHER INFORMATION: E4 XbaI R

<400> SEQUENCE: 21
aacattctag aactagtgaa tccac                                        25

<210> SEQ ID NO 22
<211> LENGTH: 29
<212> TYPE: DNA
<213> ORGANISM: Artificial sequence
<220> FEATURE:
<223> OTHER INFORMATION: VA MluI F

<400> SEQUENCE: 22
atgagacgcg tgatatccgt agatgtacc                                    29

<210> SEQ ID NO 23
<211> LENGTH: 29
<212> TYPE: DNA
<213> ORGANISM: Artificial sequence
<220> FEATURE:
<223> OTHER INFORMATION: VA AvrII R

<400> SEQUENCE: 23
gattccctag gccgcggatg ttgcccctc                                    29

<210> SEQ ID NO 24
<211> LENGTH: 36
<212> TYPE: DNA
<213> ORGANISM: Artificial sequence
<220> FEATURE:
<223> OTHER INFORMATION: rep2 MluI F

<400> SEQUENCE: 24
cctcgcgaat gcaacgcgtg gaggggtgga gtcgtg                            36

<210> SEQ ID NO 25
<211> LENGTH: 33
<212> TYPE: DNA
<213> ORGANISM: Artificial sequence
<220> FEATURE:
<223> OTHER INFORMATION: cap XbaI R

<400> SEQUENCE: 25
gattatctag acatgctact tatctacgta gcc                               33

<210> SEQ ID NO 26
<211> LENGTH: 21
<212> TYPE: DNA
<213> ORGANISM: Artificial sequence
<220> FEATURE:
<223> OTHER INFORMATION: pSMARTBAC Gib F A

<400> SEQUENCE: 26
gtggatcggt gggcagttta c                                            21

<210> SEQ ID NO 27
```

```
<211> LENGTH: 41
<212> TYPE: DNA
<213> ORGANISM: Artificial sequence
<220> FEATURE:
<223> OTHER INFORMATION: pSMARTBAC-tTA Gib R A

<400> SEQUENCE: 27
actagtcaat aatcaatgtc tctatagtgt cacctaaata c                              41

<210> SEQ ID NO 28
<211> LENGTH: 50
<212> TYPE: DNA
<213> ORGANISM: Artificial sequence
<220> FEATURE:
<223> OTHER INFORMATION: pSMARTBAC-tTA Gib F B

<400> SEQUENCE: 28
tggcaaacag ctattatggg tattatgggt actgaccctA tagtgagtcg                    50

<210> SEQ ID NO 29
<211> LENGTH: 21
<212> TYPE: DNA
<213> ORGANISM: Artificial sequence
<220> FEATURE:
<223> OTHER INFORMATION: pSMARTBAC Gib R B

<400> SEQUENCE: 29
ggctctgcac cgtattgaaa c                                                   21

<210> SEQ ID NO 30
<211> LENGTH: 40
<212> TYPE: DNA
<213> ORGANISM: Artificial sequence
<220> FEATURE:
<223> OTHER INFORMATION: tTA-pSMARTBAC Gib F C

<400> SEQUENCE: 30
tatttaggtg acactataga gacattgatt attgactagt                               40

<210> SEQ ID NO 31
<211> LENGTH: 52
<212> TYPE: DNA
<213> ORGANISM: Artificial sequence
<220> FEATURE:
<223> OTHER INFORMATION: tTA-pSMARTBAC Gib R C

<400> SEQUENCE: 31
acccataata cccataatag ctgtttgcca agatacat tgatgagttt gg                   52

<210> SEQ ID NO 32
<211> LENGTH: 40
<212> TYPE: DNA
<213> ORGANISM: Artificial sequence
<220> FEATURE:
<223> OTHER INFORMATION: E2A I-SceI F

<400> SEQUENCE: 32
attaccctgt tatccctagc ccgggcgacc gcaccctgtg                               40

<210> SEQ ID NO 33
<211> LENGTH: 56
<212> TYPE: DNA
<213> ORGANISM: Artificial sequence
<220> FEATURE:
<223> OTHER INFORMATION: E2A PI-PspI R
```

```
<400> SEQUENCE: 33
acccataata cccataatag ctgtttgcca gtacccaact ccatgcttaa cagtcc        56
```